United States Patent
Nowill

(10) Patent No.: US 10,213,504 B2
(45) Date of Patent: Feb. 26, 2019

(54) IMMUNOGENIC COMPOSITION FOR MODULATING THE IMMUNE SYSTEM AND METHODS TO TREAT BACTERIAL INFECTIONS IN A SUBJECT

(71) Applicant: Alexandre Eduardo Nowill, Sao Paulo (BR)

(72) Inventor: Alexandre Eduardo Nowill, Sao Paulo (BR)

(*) Notice: Subject to any disclaimer, the term of this patent is extended or adjusted under 35 U.S.C. 154(b) by 0 days.

(21) Appl. No.: 15/431,329

(22) Filed: Feb. 13, 2017

(65) Prior Publication Data

US 2017/0151319 A1    Jun. 1, 2017

Related U.S. Application Data

(63) Continuation-in-part of application No. 14/006,077, filed as application No. PCT/BR2012/000072 on Mar. 19, 2012, now Pat. No. 9,566,330.

(30) Foreign Application Priority Data

Mar. 18, 2011   (BR) .................................. 1100857-1

(51) Int. Cl.

| | | |
|---|---|---|
| A61K 39/00 | (2006.01) | |
| A61K 9/00 | (2006.01) | |
| A61K 39/04 | (2006.01) | |
| A61K 39/085 | (2006.01) | |
| A61K 39/09 | (2006.01) | |
| A61K 39/112 | (2006.01) | |
| A61K 39/12 | (2006.01) | |
| A61K 39/108 | (2006.01) | |
| A61K 39/095 | (2006.01) | |
| A61K 39/165 | (2006.01) | |
| A61K 39/02 | (2006.01) | |
| A61K 39/13 | (2006.01) | |
| A61K 39/25 | (2006.01) | |
| A61K 39/285 | (2006.01) | |
| A61K 39/245 | (2006.01) | |
| A61K 39/05 | (2006.01) | |
| A61K 39/29 | (2006.01) | |
| A61K 39/102 | (2006.01) | |
| A61K 47/10 | (2017.01) | |
| A61K 9/08 | (2006.01) | |
| A61K 31/05 | (2006.01) | |

(52) U.S. Cl.
CPC ............ *A61K 39/04* (2013.01); *A61K 9/0019* (2013.01); *A61K 9/08* (2013.01); *A61K 31/05* (2013.01); *A61K 39/0002* (2013.01); *A61K 39/025* (2013.01); *A61K 39/0258* (2013.01); *A61K 39/0275* (2013.01); *A61K 39/05* (2013.01); *A61K 39/085* (2013.01); *A61K 39/092* (2013.01); *A61K 39/095* (2013.01); *A61K 39/099* (2013.01); *A61K 39/102* (2013.01); *A61K 39/105* (2013.01); *A61K 39/12* (2013.01); *A61K 39/13* (2013.01); *A61K 39/165* (2013.01); *A61K 39/245* (2013.01); *A61K 39/25* (2013.01); *A61K 39/285* (2013.01); *A61K 39/292* (2013.01); *A61K 47/10* (2013.01); *A61K 2039/521* (2013.01); *A61K 2039/5254* (2013.01); *A61K 2039/70* (2013.01); *C12N 2710/16634* (2013.01); *C12N 2710/16734* (2013.01); *C12N 2710/24134* (2013.01); *C12N 2730/10134* (2013.01); *C12N 2760/18434* (2013.01); *C12N 2770/24134* (2013.01); *C12N 2770/32334* (2013.01); *C12N 2770/36234* (2013.01); *Y02A 50/474* (2018.01); *Y02A 50/482* (2018.01); *Y02A 50/491* (2018.01)

(58) Field of Classification Search
None
See application file for complete search history.

(56) References Cited

U.S. PATENT DOCUMENTS 5,595,756 A    1/1997  Bally et al.
9,566,330 B2   2/2017  Nowill

OTHER PUBLICATIONS

Auerbach et al., Angiogenesis Assays: Problems and Pitfalls, Cancer and Metastasis Reviews, 2000, vol. 19, pp. 167-172.
Collado-Romero et al., Quantitative Analysis of the Immune Response upon *Salmonella typhimurium* Infection along the Intestinal Gut, Vet. Res., 2010, vol. 41(23), pp. 1-12.
Gura, T., Systems for Identifying New Drugs are Often Faulty, Science, 1997, vol. 278(5340), pp. 1041-1042.
Hobohm et al., Pathogen-Associated Molecular Pattern in Cancer Immunotherapy, Critical Reviews in Immunology, 2008, vol. 28(2), pp. 95-107.
Jain, R., Barriers to Drug Delivery in Solid Tumors, Scientific American, 1994, pp. 58-65.
Martini et al., Strains and Species of Lactic Acid Bacteria in Fermented Milks (Yogurts): Effect on In Vivo Lactose Digestion 1-4, Am. Journal of Clinical Nutrtion, 1991, vol. 54, pp. 1041-1046.
McCarthy, E., The Toxins of William B. Coley and the Treatment of Bone and Soft-Tissue Sarcomas, Iowa Orthopaedic J., 2006, vol. 26, pp. 154-158.
Sporn et al., Chemoprevention of Cancer, Carcinogenesis, 2000, vol. 21(3), pp. 525-530.

*Primary Examiner* — Brian Gangle
(74) *Attorney, Agent, or Firm* — Linda B. Huber; Nixon Peabody LLP

(57) ABSTRACT

The present invention refers to pharmaceutical products comprising immunogenic compositions for modulating the immune system, which comprise a therapeutically effective amount of a Immunological Response Shifter (IRS) comprising two or more immunoactive antigenic agents presenting pathogen-associated molecular patterns (PAMPS) and/or danger associated molecular patterns (DAMPS) and/or Stress Response Signals (SRS), in association with an antibiotic and one or more physiologically acceptable carriers, excipients, diluents or solvents. IN other embodiments, the present invention refers to methods to treat severe bacterial infections, sepsis and modulating the immune system.

10 Claims, 3 Drawing Sheets

IMMUNOGENIC COMPOSITION FOR MODULATING THE IMMUNE SYSTEM AND METHODS TO TREAT BACTERIAL INFECTIONS IN A SUBJECT

CROSS-REFERENCE TO RELATED APPLICATIONS

This application is a continuation-in-part of U.S. patent application Ser. No. 14/006,077 filed Oct. 23, 2013, which is the National Phase of International Application No. PCT/BR2012/000072, filed Mar. 19, 2012, which designated the United States, which also includes a claim of priority under 35 U.S.C. § 119(a) and § 365(b) to Brazilian patent application No. PI 1100857-1 filed Mar. 18, 2011, the entirety of all applications is hereby incorporated by reference.

FIELD OF THE INVENTION

The present invention relates to immunogenic compositions for modulating the immune system comprising a therapeutically effective amount of a Immunological Response Shifter (IRS) comprising two or more immunoactive antigenic agents presenting pathogen-associated molecular patterns (PAMPS) and/or danger associated molecular patterns (DAMPS) and/or Stress Response Signals (SRS) (1) and one or more physiologically acceptable carriers, excipients, diluents or solvents.

The compositions of the present invention comprise immunoactive antigenic agents presenting pathogen-associated molecular patterns (PAMPS) and/or danger associated molecular patterns (DAMPS) and/or stress response signals (SRS) (1) selected from the group consisting of: (A) antigenic agents with molecular patterns associated with bacteria; (B) antigenic agents with molecular patterns associated with viruses; (C) antigenic agents with molecular patterns associated with fungi and yeasts; (D) antigenic agents with molecular patterns associated with protozoa; (E) antigenic agents with molecular patterns associated with multicellular parasites/or (F) antigenic agents with molecular patterns associated with prions.

BACKGROUND OF THE INVENTION

From the pioneering discovery of antibiotics in the end of first half of the 20th century, new antibiotics, semi-synthetic antibiotics and new chemotherapeutics with antimicrobial activity, have been developed on a large scale against most intracellular and extracellular bacteria. These developments have changed the history of medicine, allowing it to reach a wide spectrum of healing, for the vast majority of bacterial infectious diseases, which racked humanity.
The Discovery of Antibiotics and Other Drugs Thus, the discovery of antibiotics was a major milestone, a watershed, because infection could be addressed and healed, in a specific way, with a clear relationship of cause and effect, and measurable when established. This discovery greatly expanded the ability of healing in medicine, with enormous positive impact on human health and lifespans. The discovery of antibiotics in the evolution and treatment of disease profoundly influenced the research and thinking of researchers from the success achieved by this experimental model (Reeves G, Todd I. Lecture notes on immunology. 2nd ed: Blackwell Scientific Publications, 1991; Neto V A, Nicodemo A C, Lopes H V. Antibióticos na pratica medic& 6th ed: Sarvier, 2007; Murray P R, Rosenthal K S, Pfaller M A. Microbiologia Medica. 5th ed: Mosby, 2006; Trabulsi L R, Alterthum F. Microbiologia. 5th ed: Atheneu Editora, 2008).

Antibiotics were succeeded by the development and use of antifungal, antiparasitic and antiviral drugs. The "anti" drug model became a gold standard experimental model due to huge success against anti-etiologic agents, and was extended to diseases with unknown etiology against their physio pathologic process and to very similar autologous neoplastic cells, with less specificity, less selectivity and less effectivity as:
Anti-allergic;
Anti-inflammatory;
Anti-immune (Immunosuppressive);
Anti-neoplastic (cytotoxic); and
Anti-hormone.

Thus, the new "anti" drugs brought an enormous capacity for medical intervention, with numerous benefits, with definitive and partial cures, with the prolongation of life in incurable diseases, but also with huge morbidity due to side effects related to their lack of specificity to the pathophysiology of the diseases.
The Innate Immunity The innate immunity, in addition to preventing the entry of microorganisms and preventing their establishment, has another recently discovered vital function: discrimination between "self" and "not self" by the pattern recognition capability linked to the alarm and the command to start or inhibit an integrated immune response against an invading microorganism or to arrest, repair or inhibit a condition of destruction or self-aggression to the body, for example, in trauma, autoimmune diseases and allergic diseases, among others.

This dual capability was previously erroneously attributed exclusively to adaptive immunity. The innate immunity, through its own germinal receptors, recognizes invading pathogenic microorganisms, autologous or even allogeneic neoplastic cells, or allogeneic or heterologous transplants as "not self", identifying them as not belonging to the organism. From that moment, it triggers an alarm and a joint innate and adaptive immune response to eliminate them or suppress a response deleterious to the human or animal organism (Goldsby R A, Kindt T J, Osborne B. Imunologia de kuby. 6 ed: ARTMED; 2008, 704 p; Janeway C, Travers P, Walport M, Slhlomchik M J. Immunobiology five. 5 ed: Garland Pub.; 2001. 732 p.; Voltarelli J C. Imunologia clinica na pratica medica: atheneu editora; 2009; Janeway C A, Jr., Medzhitov R. Innate immune recognition. Annual review of immunology. 2002; 20:197-216. Epub 2002/02/28; Matzinger P. The danger model: a renewed sense of self. Science. 2002; 296 (5566):301-5. Epub 2002/04/16; Steinman R M, Banchereau J. Taking dendritic cells into medicine. Nature. 2007; 449 (7161): 419-26. Epub 2007/09/28.; Beutler B A. TLRs and innate immunity. Blood. 2009; 113 (7): 1399-407. Epub 2008/09/02; Moresco E M, LaVine D, Beutler B. Toll-like receptors. Current biology: CB. 2011; 21 (13): R488-93. Epub 2011/07/12) (1).

The recognition pattern of "not self", of an invasive germ is performed by sentinel cells, represented by epithelial cells, mucosal cells, and the stromal cells, such as pericytes, dendritic cells, macrophages and fibroblasts, among others. These cells, strategically distributed throughout the body, have PRRs (Pattern Recognition Receptors) and DRRs (Danger Recognition Receptors) and SRR (stress response receptors) which are receptors respectively able to recognize a) standard identification molecules, characteristic of a wide range of microorganisms, b) certain patterns for chemical and physical of said inert substances and changes to metabolic stress, such as release of free radicals and tissue chemical changes, caused by ionizing radiation or by chemical substances, among others and c) stress receptor signals that identify viruses, starvation, ER stress and oxidative stress (Pulendran, B Annual Review Immunology 2015).

The PRR does not discriminate one specific individual microorganism, but the presence of microorganisms other than the human body. Each PRR receiver may bind to several different pathogens, recognizing as PAMPs (Pathogen Associated Molecular Patterns) carbohydrates, lipids, peptides and nucleic acids from bacteria, viruses, fungi or parasites that are not found in the human or animal body.

The DRRs discriminate that there is tissue damage, a dangerous situation caused by not live or inert agents. The DRRs identify DAMPs (Danger Associated Molecular Patterns) associated with tissue damage by toxic substances, radiation, or trauma, which cause metabolic stress, release of free radicals and chemical changes in tissue, recognized by these receptors.

The SRRs (stress response receptors) identify the signal of the metabolic stress caused by environment aggressions as viral infections or viral effective vaccines, amino acid starvation, ER(endoplasmic reticulum) stress, oxidative stress, through evolutionary conserved stress-sensing mechanism, that compose de Integrated Stress Response ISR as recently discovered (Janeway C, Travers P, alport M, Slhlomchik M J. Immunobiology five. 5th ed: Garland Pub.; 2001. 732 p.; Matzinger P. The danger model: a renewed sense of self. Science. 2002; 296 (5566): 301-5. Epub 2002/04/16; Beutler B A. TLRs and innate immunity. Blood. 2009; 113 (7): 1399-407. Epub 2008/09/02; Moresco E M, LaVine D, Beutler B. Toll-like receptors. Current biology: CB. 2011; 21 (13):R488-93. Epub 2011/07/12) (1).

Thus, sentinel cells via their PRRs and their DRRs, and SRRs have a role in the breakdown of which belongs ("self") and which is does not belong (not "self") and triggering inflammation and immune response, via recognition of PAMPs of invading pathogens and DAMPs caused by neoplastic cells, inert substances and toxic substances or modifications due to trauma, or stress response signals in infections in ISR leading to a situation of real danger to the human and animal organism.

Immediately, these activated sentinel cells give alarm signals, triggering the innate immune response through the NF-kB (Nuclear Factor-kB) signal translation system, leading to the secretion of pro-inflammatory cytokines and the IRF signal translation system, that produces Type I alpha and beta interferons. These cytokines, together, acting on cells and vessels, cause a local inflammatory process, initially to contain the invading agent, autologous (tumour cell), heterologous (microorganisms, prions, grafts and transplants) or allogeneic (grafts and transplants), or to repair danger situations. This contention happens through antibodies, pre-existing, opsonizing acute phase proteins and through leukocytes and macrophages, which engulf and start to destroy the extracellular and intracellular microorganisms respectively, or eliminating other etiologic agents of any kind.

Interaction and Integration of Innate Immunity with Adaptive Immunity

Simultaneously at the site of invasion, aggression and inflammation, the innate immunity sentinel cells with the APC role (Antigen Presenting Cells), such as dendritic cells and macrophages, phagocytosis and pinocytosis microorganisms or tumour cells, or transplanted cells, among other aggressors and process their antigens. These APC cells pulsed by the antigens migrate to regional lymph nodes and activate them. The APC cells in reactive lymph nodes, activated and mature present the antigens to lymphocytes, release cytokines and thereby induce, coordinate, polarize, amplify and maintain an adaptive immune response specific to the invading germs, or neoplastic cells, or to transplanted cells, or other offending agent, allowing them to be fought and eliminated, where feasible and the consequent cure of the infection or inflammation and repair and regeneration or wound healing (1) (3).

Thus, these immune mechanisms fight diseases through innate and adaptive primary or secondary responses in an integrated and synergistic way, performed by sentinels cells, APC function sentinels, and innate immunity effectors, cellular and molecular in conjunction with the cellular and molecular effectors of adaptive immunity that are respectively lymphocytes, cytokines and antibodies.

Thus, the interaction of the two immunities, innate and adaptive, in the context of an infection or immune response against an aggressor of any kind helps to fight the disease in an integrated and synergistic way. The integration of the two initially occurs by the action of the innate immunity cells with APC function, such as dendritic cells and macrophages, but mainly by the activity of dendritic cells, as they are the ones that are able to initiate an adaptive immune response against a primary infectious or parasitic agent, effectively protecting the body(2, 3). In secondary response memory, cells govern the silent immunological process that induce full protection (1, 2, 3, 14, 26, 38, 54, 56, 57, 58, 65)

Macrophages also function as APC cells, but are more specialized and involved as part of the effector loop in phagocytosis and in the elimination of microorganisms. B lymphocytes, when mature, are also APC cells and its most well-known action is the presentation of antigens to the T lymphocytes, within the framework of cooperation of both lymphocytes to produce antibodies against T-dependent antigen, and the secondary antibody response in lymph nodes and bonne marrow. Macrophages, like other myeloid cells, are also involved in suppressing immune response in mostly in chronic infections or in acute infections. In these case of chronic infections or tumours, its performance is unfavourable to the defense of the organism because it suppresses the immune response and create a chronic infection or tumour facilitation.

When co-stimulatory molecules are not expressed on the APC cell surface, by the absence of the alarm signal characterized by the lack of activation of PRRs, DAMPs and SRR by PAMPs, DAMPs and SRSs, only the first signal occurs, given by the TCR. After the TCR binds with the antigen, in the absence of the second signal, the T lymphocyte becomes tolerant to the specific antigen shown and aborts the immune response.

On the other hand, the CD 40L molecule of activated T lymphocytes, when it binds to the CD40 molecule on the APC cells, significantly increases the expression of CD80 and CD86 molecules, increasing the current response, which thus occurs only when the adaptive T response is already engaged in defending the body. The third signal given by cytokines such as IL-1, is given usually by the APC cells after the binding of co-stimulatory molecules and the emission of the second signal. The IL-1 released by the APC cells acts on lymphocyte cells and leads to the complete expression of the receptor for IL2 and to the production of IL2 and others polarization cytokines by virgin or memory lymphocytes engaged in response initiating clonal selection and expansion(primary) or memory clonal proliferation (secondary).

Therefore, the activation of innate immunity by pathogens or by aggression is the key to unleashing the second and third signals and the occurrence of a potentially effective immunity, through the full activation of T lymphocytes engaged in the response. Without the occurrence of the second and third signal, the response is aborted and generates a tolerance specific to the antigen presented.

At the same time that the neutrophils, monocytes and macrophages initiate combat to bacteria and to other infectious agents by the linkage of PAMPs with PRRs SRSs on antigen presenting cells (APC), they activate dendritic cells and macrophages, local and newly arrived or best activated by memory cells. These cells phagocytosis and pinocytosis bacteria and bacterial antigens, processing them and starting the maturation process. The activated and maturing dendritic cells now migrate to regional lymph nodes to present antigens and initiate immune response against the invading agent.

PAMPs alone can remodel lymph node feed arteriole and induce lymph node hypertrophy that is essential for an effective primary adaptive response occurs (4, 5). In secondary responses activated and pulsed by DCs cells in inflammatory territory, effector memory CD4-CD40-L+ cell migrate in a CD62P-dependent fashion into the reactive lymph nodes via HEVs and license dendritic cells for T cell priming against weak antigen, tolerate antigens and auto antigen starting an auto immune disease or improving an immune response in an ongoing infection or neoplastic disease(4). Also in inflammatory territories effector memory CD8 T cells secrete CCL3, that in turn activate MPCs to produce TNF alfa that induce PMNNs and Others MPCs to produce ROIs and clear intracellular bacteria. Unrelated intracellular pathogen sensitive to ROIs can also be clear by bystander activation in overlapping diseases or overlapping immune responses (6, 7).

The mature antigen-pulsed APC cells, especially dendritic cells, in lymph nodes, collaborate with the T and B lymphocytes and initiate the adaptive primary or secondary response (1). Dendritic cells are the most potent cells for the presentation of antigens and the only APC cells able to activate a virgin CD4 T lymphocyte and to start a new immune response (2,3).

After a period of approximately seven days in the lymph node, the collaboration between blank CD4 lymphocytes CD4-Th0), which become T CD4 Th2 or Tfh, with B lymphocytes and antigen presenting dendritic cells, initiates the differentiation of specific sensitized B lymphocytes. These B cells, now activated, recognize bacterial antigens by surface immunoglobulins, collaborate with T helper cells, cells after contact with these antigens, proliferate, mature, and differentiate into plasma cells that now release specific antibodies against this bacterium in a first moment outside of follicular node in the B cell area, in activated lymph nodes and after differentiation goes inside and induce germinal centre formation and secondary B cells responses with collaboration with CD4Tfh and others CD4T helpers cells. In secondary B cells responses, long lived plasma cells secrete Tcell dependent antibodies in bonne marrow, after initial production in lymph nodes (1,6) (8, 9). Infections of all types, bacterial, viral, fungal and parasitic may, in general, in the acute phase, evolve to a full cure with regeneration and healing, or for a cure with sequelae. They can also develop into an incurable chronicity, with or without control of the disease, to chronicity with healing, with or without sequelae, or to death.

Polarization of the Immune Response

The classic immune profiles known and induced by dendritic cells by direct and indirect contact with the different cytokines and generated by T CD4 cells are of four types(10-12):

a) cellular Th1 profile, which generates cellular immunity mediated by cells; (13) b) humoral Th2 profile, which generates humoral immunity mediated by antibodies(13);

c) tissue or inflammatory Th17 profile, which generates inflammatory tissue immunity, also mediated by cells and cytokines, which induce an important inflammation for the elimination of certain pathogens, and(13, 14)

d) Treg/Tr1 profile, which suppresses the immune response and controls, by inhibiting the other three profiles described above, ensuring the return of the body equilibrium state. (13, 15) e) New profiles have been stablished, as the Tfh (follicular Helper) of the humoral response (16), the Th9 profile for certain parasites like Helminths (17), Th22 that produce IL22 involved in Skin protection (17) or other profiles that may be discovered or no fully established(18).

Thus, the various profiles ensure the defense of the organism and the elimination of causative heterologous (infectious) agents invading and colonizing autologous (neoplasia). The last classic profile ensures the termination of the immune response, the balance, the regeneration, the safe return to normalcy and it prevents self-injury and allergy and is therefore vital to the health and preservation of the human species and animal, as much as the other profiles.

The phenomenon of polarization of the immune response is defined as the predominance of a certain immunological profile such as Th1 or Th2 at the expense of other profiles that become secondary or null. This phenomenon happens according to the type of attack suffered by the body. That is, according to the type of infection, pathology, and infection stage or pathology stage, the different type of immune response will be predominant, and it may be a cellular, humoral, tissue inflammatory, or immune-regulatory response, while other types of immune responses are inhibited, resulting in the phenomenon of polarization. (12)

By definition, there is a dominant profile in polarization, but other non-dominant profiles are also needed, and expressed in a complementary manner that will help eliminating the disease. For example, tuberculosis is the appearance of Th17 cells in the lung which allows Th1 cells to settle and may lead to cure this infection in the lung parenchyma (Stockinger, B. and Veldhoen, M. Differentiation and function of Th17 T cells. Current Opinion in Immunology, 19 (3), pp. 281-286. 2007). In viral infections, the CTL cells of Th1 profile destroy cells infected by viruses, to eliminate the virus. However, antibodies are required to prevent the virus from infecting other healthy cells and thus preventing the spread of infection. The coordinated assembly of the two profiles is essential for the healing of certain viral infections. Certain intestinal infections by extracellular Gram-negative bacilli require, for its cure, in the final stage, besides the Tfh and Th2 profile, the generation of a supplementary Th17 profile capable of generating a strong inflammation, necessary to eliminate this type of bacteria. (12)

In conclusion, due to the fact that the dendritic cells are the only professional APC cells capable to initiate a primary adaptive immune response and are the most potent in triggering a secondary specific immune response, in any profile, they are then commanding the interaction and integration of innate immunity with adaptive immunity to produce an effective immune response capable of curing a disease. Dendritic cells in collaboration with other APC and sentinel cells in contact with different aggressors in different functional states, in the inflammation sites, in the lymph nodes, in the spleen, in the mucous membranes, are able to lead, coordinate, polarize, and amplify the adaptive immune response governing them, primary and secondary, e.g., specific for the peptides of invading pathogens, which in this case is the most appropriate for the removal of the ongoing infection(1,2,3).

Therefore, dendritic cells and other APC cells are key cells of the innate immune response, since they evaluate the nature of the autologous and heterologous causative agent, i.e., the type of pathogen or colonizing cells and aided by the sentinel cells, they measure and evaluate the size of the heterologous or autologous aggression, its extension, its intensity and aggressiveness, besides commanding the adaptive response with the profile and the intensity required for the elimination of the pathogen. In other words, innate immunity contextualize the aggression in a primary response and recontextualize in a secondary effective one by the action of T B and some NK memory cells (19) (20) (8, 9, 20-31)

After differentiation, a re-differentiation can occur, induced by the microenvironment and/or the type of antigen or its presentation, in which a Th1 or Th2 profile can be exchanged for an inflammatory profile or an immunosuppressant profile or vice versa. This extreme plasticity of the immune system to differentiate or re-differentiate in either direction indicates a strategic window for manipulation of the immune system, during infection, when the direction taken by the polarization is not the best one for curing the infection process or neoplasia (32).

As an illustrative example, we have what happens in a severe infection or septicaemia, that induce sepsis with massive inflammation caused by cytokine, induced by the large number of microorganisms which touch the sentinel cells throughout the body, induces also a Th17 a profile, which in turn increases the inflammation more and therefore becomes detrimental, leading to tissue destruction, rather than inducing healing and paradoxically inducing late immunosuppression by the Treg/Tr1 profile and exhaustion state. In these cases the Th17 profile, by tissue destruction and the amplification of inflammation, is implicated in the generation of clinical complications such as severe ARDS (acute respiratory distress syndrome in adults), lung shock, renal failure, or shock, that compromises healing (4, 33, 34).

The re-differentiation of polarization for the Th1 or Th2 profiles, with the inhibition of massive inflammation, is the logical and strategic path for a designed or prepared immunotherapy to try to resolve this dramatic and deadly type of situation, during a severe infection or sepsis, which has a significant mortality and morbidity and for which antibiotics and other antimicrobials, in current patterns such as single mode, have disappointing anti-infective results. The same example applies to serious intra cellular bacterial, fungal, viral and parasitic infections, with extensive tissue destruction and massive inflammation, usually of poor prognosis.

The Use of Adjuvants to Stimulate Immune Response

The human and animal organisms do not usually produce antibodies against soluble proteins, necessitating the use of so-called nonspecific or unrelated adjuvants to obtain the desired immune response. These adjuvants used since the dawn of immunology, in immunizations and in vaccine applications, were and are made up of parts of microorganisms, mineral oils and other substances that activate the innate immunity, which then gives the alarm and control necessary for the development of desired immune response to the protein or to the vaccine in question (GOLDSBY RA, KINDT TJ, OSBORNE BA. IMUNOLOGIA D E KUBY. 6 ed: ARTMED; 2008. 704 p); (Janeway C, Travers P, alport M, Slhlomchik M J. Immunobiology five. 5 ed: Garland Pub.; 2001. 732 p.); (VOLTARELLI JC. IMUNOLOGIA CLINICA NA PRATICA MEDICA: ATHENEU EDITORA; 2009); (Janeway C A, Jr., Medzhitov R. Innate immune recognition. Annual review of immunology. 2002; 20:197-216. Epub 2002/02/28.); (Matzinger P. The danger model: a renewed sense of self. Science. 2002; 296 (5566): 301-5. Epub 2002/04/16.): (Steinman R M, Banchereau J. Taking dendritic cells into medicine. Nature. 2007; 449 (7161): 19-26. Epub 2007/09/28.); (Beutler B A. TLRs and innate immunity. Blood. 2009; 113 (7): 1399-407. Epub 2008/09/02.); (Moresco E M, LaVine D, Beutler B. Toll-like receptors. Current biology: CB. 2011; 21 (13): R488-93. Epub 2011/07/12).

It should be noted that the use of adjuvants for immunization, despite being one of the oldest features, and still current, highly used and essential for vaccinations and for studies of immunology, was considered only as a useful nonspecific effect. It was not envisioned, for more than a century, its role in the innate immunity in the discrimination of what is "Self" and not "Self" and its unique and fundamental capacity to the survival of the human species and animals: to give the alarm signal and the command to start or not start, or inhibit, an integrated, protective or healing, innate and adaptive, immune response (GOLDSBY RA, KINDT TJ, OSBORNE BA. IMUNOLOGIA D E KUBY. 6 ed: ARTMED; 2008. 704 p); (Janeway C, Travers P, Walport M, Slhlomchik M J. Immunobiology five. 5 ed: Garland Pub.; 2001. 732 p.); (VOLTARELLI JC. IMUNOLOGIA CLINICA NA PRATICA MEDICA: ATHENEU EDITORA; 2009); (Janeway C A, Jr., Medzhitov R. Innate immune recognition. Annual review of immunology. 2002; 20:197-216. Epub 2002/02/28.); (Matzinger P. The danger model: a renewed sense of self. Science. 2002; 296 (5566): 301-5. Epub 2002/04/16.): (Steinman R M, Banchereau J. Taking dendritic cells into medicine. Nature. 2007; 449 (7161): 419-26. Epub 2007/09/28.); (Beutler B A. TLRs and innate immunity. Blood. 2009; 113 (7): 1399-407. Epub 2008/09/02.); (Moresco E M, LaVine D, Beutler B. Toll-like receptors. Current biology: CB. 2011; 21 (13): R488-93. Epub 2011/07/12).

Treatment of Severe Infections, Sepsis, and Septic Shock

The current paradigm in infectious diseases is that antimicrobials are toxic selective drugs that destroy or block pathogens, like bacteria, fungus, virus and parasites, with little damage to the host and are responsible for the clearance of these agents. For this reason, they are traditionally employed in monotherapeutic approaches. (Reeves G, Todd I. Lecture notes on immunology. 2nd ed: Blackwell Scientific Publications, 1991; Neto V A, Nicodemo A C, Lopes H V. Antibióticos na pratica medic& 6th ed: Sarvier, 2007; Murray P R, Rosenthal K S, Pfaller M A. Microbiologia Medica. 5th ed: Mosby, 2006; Trabulsi L R, Alterthum F. Microbiologia. 5th ed: Atheneu Editora, 2008).

The treatment of severe infections, sepsis, and septic shock, combine more than one antibiotic, avoiding microbial resistance in combination with support measures to prevent or limit SIRS, ARSD or MODS or helped by preventive vaccines. Therefore, the current research is mostly focused on new antimicrobial drugs, drugs that prevent microbial resistance, and new medicines or biological agents to inhibit or control pro-inflammatory and immunosuppressive microenvironments, and vaccines.(34-41)

Paradoxically, the detailed analysis of the experimental model, that gave rise to the current paradigm in infectious diseases reveals an unexpected and not foreseen different conclusion: In that model, there are 3 players in the Petri dish: the pathogen, the antimicrobial drug and an inert culture medium that don't interfere in the interaction of the first 2 components. In that case, if the drug is effective we can say that the antibiotic made the elimination or clearance of the pathogen in vitro.

However, in the in vivo correlated situation, there are also 3 components: the antibiotic drug, the pathogen and the human or animal bodies, that are not an inert medium, and have an immune system with the same task of the antibiotic, that is, they also block and combat the pathogen. We cannot translate the conclusion of a system in vitro with 3 components and 2 variables to a system in vivo with 3 components and 3 variables. They are not scientifically comparable and the conclusion in vitro cannot be translated to the in vivo system to explain cure.

For that reason, in the case of the antibiotic that can eliminate the isolated bacteria in vitro, it is not possible to say that the same antibiotic is responsible for the clearance of this pathogen or responsible for the cure of the infection in vivo when its occurs. The only conclusion that can be made in that case is: the success of the antimicrobial treatment in the clearance of the pathogen and in the cure of infection in vivo depends on the joint action of the antimicrobial drug and the immune system.

In strong support of this view, the immune system is deficient in the extreme of ages, dysfunctional in elders and immature in the first years of age. In this periods of life, infections are usually more severe and frequent, and there are also a higher rate of morbidity and mortality, even when antibiotics are used in correct indication, dosing and timing.

Also in the case of severe secondary immune deficiencies, like terminal AIDS, terminal oncologic patients, other terminal immune compromised patients and in terminal severe primary immune deficiencies of any kind, cure with antimicrobial drugs are not possible. In the immune compromised host, the antibiotics are used in higher doses compared to the immune competent patient for the very same clinical or veterinary condition. In the undeveloped world, where most of human population lives, malnutrition compromises the fitness and functionality of the immune system.

The lack of sewerage and drinkable water supply submits these populations to constant aggressions by innumerable pathogens, compromising the efficiency of the defense system and provoking disease. This constant aggression and frequent illness create an unhealthy positive feedback loop, compromising continuously the immune system and health. Finally, the lack of protection from environment aggression also weakens the body and immune system. These three conditions combined in a synergic way also create an unhealthy positive feedback loop, that severely compromises the immunological system, and decreases the efficiency of antimicrobial drugs, shortening the lifespan of these populations. There is no available data supporting of the isolated action of antimicrobial medicines in vivo without the collaboration of the immune system, since humans and animals cannot live without a functional immune system and once invaded the immune system react by innate and adaptive responses that only finish after the clearance of the pathogen and the end of tissue repair and the return to homeostasis (7,8).

In agreement with this interpretation, there is no clear evidence in the literature of clearance of pathogen in vivo by the sole action of antibiotics or antimicrobial drugs. In conclusion, without a functional immune system, it is impossible to cure severe infections with antimicrobial drugs in the monotherapeutic approach. In contrast, the cure of some infections is possible without antimicrobial drugs. Altogether, these evidences pointed to a definitive and significant role exerted by the immune system in the cure reached by antimicrobial drugs in vivo in infections (Reeves G, Todd I. Lecture notes on immunology. 2nd ed: Blackwell Scientific Publications, 1991; Neto V A, Nicodemo A C, Lopes H V. Antibióticos na prática medic& 6th ed: Sarvier, 2007; Murray P R, Rosenthal K S, Pfaller M A. Microbiologia Medica. 5th ed: Mosby, 2006; Trabulsi L R, Alterthum F. Microbiologia. 5th ed: Atheneu Editora, 2008).

A new explanation should be formulated in order to better understand the cure induced by the antimicrobial drugs in vivo, independently of the, well known mechanism of action in vitro against microbes. The inventors propose a new concept, in which the antimicrobial drugs can be considered as equilibrium shifters (ES) in a host×pathogen competition, that favours the host immune system in a multivariable context. The variables are: concomitant diseases, traumas, age, sex, race, psychological health, innate and adaptive immunity, metabolism, nutrition, physiological flora microbiota, environmental aggression by drugs, and exposure to radiation, gases, pathogens and medical treatments.

What possibly occurs is that the antimicrobial drugs by their action against bacteria facilitate the work of the immune system in pathogen clearance, reverting the host× pathogen equilibrium competition and promoting the cure. The antimicrobial drugs would function as equilibrium shifters of the host×pathogen competition by significantly: weakening the pathogens action and reducing their numbers in vivo and by that way facilitating the role of the immune system in microbe clearance. Alternative outcomes are death or chronic infection, regardless of the use of antimicrobial drugs.

The application of this new concept in the context of the discovery of new treatments for severe or potential incurable infections/inflammatory syndromes, such as sepsis or septic shock deserves some considerations. As equilibrium shifters in the host versus pathogen balance, antimicrobial drugs have a compulsory partner in vivo, the immune system. By accepting the concept that antimicrobial drugs are not the main players in achieving cure but act as important and frequently necessary helper factors that contribute to shift the balance in favour of the host, in infection/inflammation disease, a primordial question emerges: how to change and improve an established initial exaggerated, ineffective, improper ore deleterious IR conducting the immune system to generate the best immunological response (IR) available, innate and adaptive capable to combat and make the clearance of the pathogen and at the same time having an physiological benefic anti-inflammatory action during the course of the treated disease.

OBJECTIVES OF THE INVENTION

In general, one of the objectives of the invention is providing products comprising immunogenic compositions, in certain embodiments such compositions are combined with one or more antibiotics, as well as methods and uses thereof for treating and/or preventing infectious diseases and preparing medicaments therefor.

It is a specific object of the present invention to provide immunogenic compositions for modulating the immune system comprising a therapeutically effective amount of two or more Immunological Response Shifter (IRS) comprising an immune active antigenic agents that present pathogen-associated molecular patterns (PAMPS) and/or danger associated molecular patterns (DAMPS), and stress response signals(1) and one or more physiologically acceptable carriers, excipients, diluents or solvents.

In particular, it is an objective of the present invention providing immunogenic compositions for modulating the immune system which comprise Immunological Response Shifters (IRS) that have immune-active pathogen-associated molecular patterns (PAMPS) and/or danger associated molecular patterns (DAMPS) and/or stress response signals (SRS) selected from the group consisting of: A) antigenic agents with molecular patterns associated with bacteria; (B) antigenic agents with molecular patterns associated with viruses; (C) antigenic agents with molecular patterns associated with fungi and yeasts; (D) antigenic agents with molecular patterns associated with protozoa; (E) antigenic agents with molecular patterns associated with multicellular parasites/or (F) antigenic agents with molecular patterns associated with prions.

The present invention also aims to provide uses of the above-mentioned immunogenic compositions for preparing pharmaceutical products and methods for modulating the immune system, particularly for real-time replacement of an innefective immune response with an effective immune response.

Therefore, the present invention aims to provide products and methods for treating infectious diseases, including severe infection, sepsis and multirresistant bacteria, and modulating the immune system. The effectiveness of the invention is due to a real time replacement of an ineffective immune response with an effective immune response. Such replacement made by proactively creating a new image of the aggressor pathogen to the host immune system, in order to reset, lead back, control and improve the same.

Real-time replacing the ineffective immune response for a new effective one capable to change the host×pathogen equilibrium competition in favour to the host propitiating a chance of cure is the challenging task. This problem touches the Pasteur paradigm that says that it is possible to immunize the host to confer protection against the aggressor upon a second encounter, without significant clinical signs of the disease.

The basis of these phenomenon is the established immunological memory phenotype in T and B lymphocytes and, also to a lesser extent in NK cells (7-21)), as recently demonstrated. Altogether, these cells may induce inflammatory innate and adaptive responses in the second contact with the antigen. That is the basis of preventive vaccines, which are the most effective medicines ever created so far. Paradoxically, the state of the art lacks therapeutic vaccines for infectious diseases.

Revisiting the paradigm of Pasteur, we can take as a model two of the most effective preventive virus vaccines ever developed against invariable pathogens: smallpox and yellow fever (YF-17D). The first eradicated smallpox until now and the second led to the development of protective immunity that could last more than 35 years, after a single dose. A series of detailed modern scientific studies with YF-17D Yellow Fever vaccine in system biology and system vaccinology, demonstrated that virus, make contact with a wide range of sentinel and professional APC innate cells, activating the same. Activating also multiple DC subsets by the stimulation of multiple PRRs, DRRs, stress response receptors by multiple PAMPs and DAMPs, stress signals in each DC cell type and subset and in multiple subsets and DC cells types and others APC cells and NK cells.

These multiple sentinel cell activation that leads to an also complex and multiple synergic DCs activation in multiple inflammatory and lymphoid territories lead to a systemic CD4 TH1, CD4 TH2, CTL CD8 and B cell and antibodies polyclonal effective responses that abrogate the viremia and make the inactivation and clearance of the virus and infected cells letting them without the capacity to recycle and to perpetuate themselves in environment (42).

Some malfunction of the immune system due to rare genetic defects can give rise to an also rare vaccine disease that is in general very severe or even fatal, proving further evidence that the elimination of the vaccine virus as a matter of competition between host immune system and virus in a beneficial induced disease and not as a single vaccine immunization(43). The activation context in a systemic subclinical disease is huge and complete different than a single repeated immunization with antigen vaccine these is one of the reason of the high effectivity of these two vaccines(1) (44-50)

In conclusion, an aggressive wildtype virus would affect the host-pathogen balance in a different way than a vaccine virus, leading to a severe disease in one case and a subclinical disease in the other(1) (44-50). It is well known that an overlapping acute infection over a chronic one, such as cancer or chronic infection, can induce the cure of the underlying disease (42, 51). A strong activation can prevail over an ineffective one, improving the last one an altering the host×pathogen equilibrium competition and the outcome (42,51). It is also well known that the activation induced by the overlapping of an effective unrelated specific immune response is the best way known to rescue a state of tolerance, immunosuppression or anergy to a state of normal response (52).

In the same way, experiments with mutagenesis transforming low into high immunogenic tumours induce tumour rejection that cannot be generated with the wild tumour and, also induce CTLs against subdominant epitopes(53, 54). PAMPs alone can remodel lymph node feed arteriole and induce lymph node hypertrophy that is essential for an effective primary adaptive response. An unrelated activated or pulsed effector memory T specific CD4+CD40L+ migrate in a CD62P-dependent fashion into the reactive lymph nodes via HEVs and license dendritic cells for T cell priming against weak antigen, tolerate antigens and auto antigen starting an auto immune disease or improving an immune response in an ongoing infection or neoplastic disease (4, 52, 55). Effector Memory CD8 T cells release CCL3, that in turn activate MPCs to produce TNF alfa that induce PMNNs and Others MPCs to produce ROIs and clear bacteria. Unrelated pathogen sensitive to ROIs can also be clear by bystander activation(6, 56-59). Recently, it was also recognized that the status of the microbiome of the intestinal flora intervenes and can determine the effectiveness of a given vaccination.

These situations, studied in parallel, of disease and vaccine disease, isolated disease and overlapping diseases, blocked specific immune response overlapped by effective specific immune response, natural no immunogenic tumours versus mutagenic immunogenic tumours, vaccine immunization and ongoing immune response to the flora microbiome and T CD4 Effector Memory cells and CD8 T effector memory induced potent activation of innate cells, PAMPs effect on feeding lymph nodes arteriole and lymph nodes hypertrophy and the others studies described above, reveal very important points of the immune response in Pasteur paradigm that should be considered for the proposal of a new hypotheses of work destined to improve treatment of infections/inflammations, neoplastic, allergic and others diseases in the context of the design of new therapeutic approach. Such Important Points of Observations are:

1—The immune system is reactive and not proactive and it has a unique huge response potential but only use the stimulated patch by which they see the aggressor in the context of the host×parasite competition balance. In consequence, the outcome of a given new immune response is always circumstantially a fortuitous reply determined by the host×parasite competition balance and even if is efficient they are not the best possible response. In conclusion, a primary immune response is always a fortuitous reply possible to be improved 2—The best possible response, or protection, occurs only in secondary response due to effective memory formation after the cure of a severe disease ore effective vaccination. Thus, memory cells are key in generating protective immunity.

3—The innate response is not specific by its own nature and can hold multiple specific adaptive responses at the same time and in the same territories with synergic or antagonist effects. Because human and animal organisms can hold multiple aggressions at the same time and even in the same territory, the sinks of the innate immunity receptors recognition system recognize an expandable and changeable universe of PAMPs, DAMPs, and Stress Signals in contrast to a defined recognition of the identity of an aggressor pathogen by adaptive immunity.

4—Based on the characteristic cited above and on the study of the mechanism of protection induced by YF-17D vaccine the rational logistic to activate the innate immunity effectively, paradoxically should have to be based on the multiplicity and diversity of activation of different sinks PRRs, DRRs and Stress Signals in different cellular compartments and in multiple cells sentries and APCs cell types with multiple cytokines and chemokines secretion in multiples territories lymphoid and no lymphoid to reach the best available adaptive immune response independently of the antigenic receptors universe to be activated in the adaptive specific response.

5—The major role of the primary response is to circumscribe the pathogen in a pro-inflammatory environment until an effective adaptive response takes place. The primary adaptive response in acute infection is also pro-inflammatory. Both can be very harmful if the contact surface is big and usually induce a symptomatic illness and can also induce a deleterious lethal systemic inflammation 6—The secondary innate and adaptive effective responses are provided by T, B memory cells and in some circumstances by NK memory cells that give a faster, correctly polarized, more accurate, quiet, low inflammatory and protective immune response, when available. These modified secondary adaptive immune responses for its anti-inflammatory nature had to the cells memory can effectively deal with systemic wide range of pathogen surface contact without being harmful for the human and animal organism.

7—In overlapping situations cited above the innate territory activated of both diseases ore immune responses corporate for the same cells sentries, APCs, with the release of common cytokines, common chemokines and will be in the same activated lymph nodes, and inflammatory territories all the scene ore battle context will be the same for the two responses. When secondary and primary adaptive response occur simultaneous the secondary adaptive immune response is the dominant immune response by the action of memory cells that reset the signal transmission in innate and adaptive cells and induce the primary responses to shift to a low inflammatory pattern in a target memory modified territory.

8—Also, these effects can be obtained by the injections of a mix of PAMPs and secondary antigens to cognate memory cells that induce a secondary immune response and activate optimally PMCs and PMNNs to clearance bacteria sensitive to, ROIs and other mechanism and activate optimally lymph nodes and improve ongoing immune response or can induce a poor or tolerated or no immunogenic one.

In conclusion, the immune system is reactive and not proactive and the quality and effectiveness of the natural immune response depends mainly of two factors:

First factor is the existence or not of an immunological effective specific memory that it determines a secondary or a primary immune response. In the case of a secondary response the best possible response is available and the outcome is a quiet protection. In the case of a primary response the new immune response is always circumstantially a fortuitous reply and the outcome depends on the second factor and can be improved.

The second factor is the host×parasite competition balance (40, 49, 53, 54, 60-78).

Therefore, the immune system cannot improve by itself an already ongoing primary immune response and the answer for the question of how to change and improve an established initial primary improper immune response is apparently complex but strategically simple because there are only two factors determining the outcome of an immune response. In a primary immunological reply, there are only one remainder factor that is the context of the host×pathogen competition balance to be modified to possible improve the ongoing inefficient immune response. The antimicrobial drugs acts by weakening, the pathogens action and reducing their numbers in vivo, and would function as ES of the host×pathogen competition like describe and proposal above. By this action the antimicrobial drug alter positively the host pathogen equilibrium balance and the outcome but don't alter the nature of the ongoing primary response. Following this rational analysis, it would be enough to changing the nature of the ongoing primary improper natural immune response to a secondary effective standard to be favourable to the organism. A task, that obviously, the immune system cannot accomplish without help, because it estimates an ordinated delay with a differentiation step. How to transform in real time, immediately a primary fortuitous reply in a secondary best possible response? The answer is by the best possible secondary activation.

In order to accomplish this task, the strict reactive characteristic of the immune system in a primary response that depend mainly on the pathogen immunogenicity and action and on the fitness of the immune system, open the door for a proactive medical immune intervention that can use all the remainder vast immune potential of available reply to change the host×parasite competition balance in favour of the host with a new secondary standard of this initial IR. This strategical and planned immunological action must be able to reset, lead back, control, modify and improve in real time the immune system action to induce a favourable secondary specific effective IR for positively alter the context of host×parasite competition and the outcome.

The only possible answer would be changing the perception or how the immune system sees and characterizes the aggressor agent by including a great amount and diversity of new secondary memory antigens determinants constructing a new perceived identity for the aggressor pathogen.

This new perceived identity may be built in all disease's lymphoid sites or not, or even inflammatory territories, in controlled periods, that naturally will change completely the activation by a secondary huge one. Now with a new best secondary activation for the ongoing disease the immune system could reprogram the immune response based mostly in secondary well known antigenic determinants with a minority of primary determinants deriving from the aggressive pathogen that will generate a complete new different effective specific and well polarized immune response. The best possible one will be generated with secondary tracts in the secondary resetting, low inflammatory territories.

The sum of the total effective anti-inflammatory secondary response to the new created image of the aggressor pathogen could revert all the induced tolerance, anergy, scape mechanism and could also induce a immune response to all the weak antigens or subdominant epitopes to create the best possible effective response in a totally different poor inflammatory battle field, that create a complete new host× parasite competition balance in favour of the host. To reach this goal is necessary to create a new ES Equilibrium Shifter an IRS (Immunological Response Shifter) whose action and creation should be based on the important and significant observations made from the study of the Pasteur paradigm described in details above.

This new IRS for the proactive action of the proposed and planed immunotherapy must be constituted by a vast and very diverse pathogen secondary antigen universe for which the organism disposes an effective memory repertoire. These antigens must be with priority inert and be applied in all the territory of the illness exceeding its limits.

Such antigens should be able to induce a multiple huge secondary anti—inflammatory activation to overlapping completely the primary pro inflammatory activation induced by the pathogen. These antigens should be applied each 3 to 5 days, to inhibit the immune suppressive cells generation imitating a draw out illness. The propose of this immunotherapy is to create at the biological level un new virtual but real exogenous ore endogenous pathogens full identified by the innate and adaptive immunity in his most part as a secondary and well know aggressor by memory effective cells that will induce the best available immune response replacing the initial one. Changing the inner image of the pathogen picked-up by innate and adaptive memory cells we proactively change the context of the host×pathogen competition now in favour of the host. The reactive immune system activated excellently by the proactive immunotherapy will real time reprogram, reset and leads back the best available secondary anti-inflammatory specific immune response against the etiologic agent reverting his initial advantage in an ongoing illness.

For the proof of concept that a new perceived image of the exogenous or endogenous pathogen by an innovative IRS may real time govern, reset and lead back an already established pathological response we use some compassionated cases of reversed lethal irreversible sepsis mostly with multi-resistant microorganisms out of the scope of the best available antibiotics used in combined fashion.

The following positive significant results of this clinical cases shown in the Examples prove and suggest that it is possible real time governing, resetting, leading back the immune system and create new secondary effective, anti-inflammatory immune responses during the treatment of a disease by replacing the initial exaggerated, ineffective, improper ore deleterious primary immune response one by proactively creating a new image of the aggressor pathogen.

This is the first demonstration that is possible to govern, reset and lead back an ongoing immune response in vivo in favour of the host altering positively the host×pathogen competition balance, as well as the outcome, and also having a significant synergic effect with antimicrobial drugs.

Another object of the invention is the use of immunogenic compositions for preventing and/or treating infectious diseases. Particularly, providing methods of treating bacterial infections and sepsis and uses of the above-mentioned immunogenic compositions for preparing medicaments and kits for treating bacterial infections.

Definitions

In the context of this patent application, abbreviations are used several times, and their definitions, according to their usage in this application, are summarized below:

IRS: Immunological Response Shifter

BCG refers to attenuated *Mycobacterium bovis*, Bacille Calmette-Guerin;

DAMPS refers to danger associated molecular patterns;

DECA refers to the IRS composition 1a described in Example 1 of the present patent application;

GM-CSF refers to "Granulocyte macrophage colony-stimulating factor";

PAMPS refers to pathogen-associated molecular patterns.

PFU: plaque forming units.

PPD refers to purified protein derivative of *M. tuberculosis;*

PPD refers to the fraction of the purified protein extract culture of Koch's bacillus ("Purified Protein Derivative"). The PPD is the major antigen of *Mycobacterium tuberculosis;*

TDCI50 is a unit for quantification of viral particles and is the infectious dose in 50% of cells in a tissue culture;

Koch's Tuberculin refers to inactivated *Mycobacterium bovis* lysate;

Units Lf or "Limes flocculation units" is the international unit for quantifying antigens in toxoid vaccines accepted by the World Health Organization;

VITER: The IRS composition 1b described in Example 1.

ISR: Integrated Stress Response

SRS: Stress response signals

SRR: Stress response receptors

ES: equilibrium shifter

DETAILED DESCRIPTION OF THE EMBODIMENTS

In a first embodiment, the invention refers to a pharmaceutical product comprising one or more antibiotics with one or more immunogenic compositions for modulating the immune system comprising a therapeutically effective amount of three or more (e.g., 3, 4, 5, 6, 7, 8, 9, 10, 11, 12, 13, 14, 15, 16, 17, 18, 19, or 20 or more) synthetic antigenic agents or natural antigenic agents, or fractions and combinations thereof, comprising pathogen-associated molecular patterns (PAMPS) and/or danger associated molecular patterns (DAMPS) selected from at least two groups consisting of: (A) antigenic agents with molecular patterns associated with bacteria, (B) antigenic agents with molecular patterns associated with viruses, (C) antigenic agents with molecular patterns associated with fungi and yeasts, (D) antigenic agents with molecular patterns associated with protozoa, (E) antigenic agents with molecular patterns associated with helminthes, and (F) antigenic agents with molecular patterns associated with prions; and one or more physiologically acceptable carriers, excipients, diluents or solvents.

Such pharmaceutical product may be a composition, a kit, a medical device or any other product which aims to deliver the antibiotics and the one or more immunogenic compositions as described above to a tissue.

The one or more antibiotics comprised in the pharmaceutical product of the invention may be selected from the following classes: Amino Acid Derivatives, Aminoglycosides, Aureolic Acids, Aziridines, Ansamycins, Benzenoids, Carbapenems, Cephalosporins, Coumarin-glycosides, Diphenyl Ether Derivatives, Epipolythiodioxopiperazines, Fatty Acid Derivatives, Glucosamine, Glycopeptides, Imidazoles, Indol Derivatives, Lipopeptides Macrolactams, Macrolides, Nucleosides. Penicillins and Cephalosporins (beta-Lactams), Peptides, Peptidyl Nucleosides, Phenicoles, Polyenes, Polyethers, Pyridines and Pyrimidines, Quinolones and Fluoroquinolones, Statins, Steroids, Sulfonamides, Taxoides and Tetracyclines.

Preferably the immunogenic compositions of the present invention comprise immunoactive antigenic agents presenting pathogen-associated molecular patterns (PAMPS) and/or danger associated molecular patterns (DAMPS) selected from the group consisting of: (A) antigenic agents with molecular patterns associated with bacteria; (B) antigenic agents with molecular patterns associated with viruses; (C) antigenic agents with molecular patterns associated with fungi and yeasts; (D) antigenic agents with molecular patterns associated with protozoa; (E) antigenic agents with molecular patterns associated with multicellular parasites/or (F) antigenic agents with molecular patterns associated with prions.

Still more preferably the immunogenic compositions of this invention include pathogen-associated molecular patterns (PAMPS) and/or danger associated molecular patterns (DAMPS) selected from among at least three categories (A), (B), (C), (D), (E) and (F) described above.

More preferably, the immunogenic compositions of this invention include pathogen-associated molecular patterns (PAMPS) and/or danger associated molecular patterns (DAMPS) selected from among at least four categories (A), (B), (C), (D), (E) and (F) described above.

Antigenic agents of the present invention can be selected from epitopes, genetic materials, lipids, polysaccharides and/or immune active proteins of the present invention can be obtained by purification from isolated fragments of material existing in nature or fractions derived from plant, animal or microbiological extracts, or produced by genetic recombination, preferably derived from viral, fungal, parasitic or bacterial prion strains.

Thus, the antigenic agents of the present invention with molecular patterns associated with bacteria of the present invention may be selected from, but not limited to antigenic agents with molecular patterns associated with bacteria of the genera *Staphylococcus, Streptococcus, Enterococcus, Corynebacterium, Bacillus, Listeria, Clostridium, Mycobacterium, Actinomyces, Nocardia, Escherichia, Proteus, Klebsiella, Serratia, Enterobacter, Salmonella, Shigella, Pseudomonas, Burkholderia, Stenotrophomonas, Acinetobacter, Vibrio, Campylobacter, Helicobacter, Bacteroides, Neisseria, Moraxella, Haemophilus, Bordetella, Brucella, Francisella, Pasteurella, Yersinia, Legionella, Gardnerella, Treponema, Leptospira, Borrelia, Mycoplasma, Rickettsial* and *Chlamydia*.

Antigenic agents with molecular patterns associated with virus of the present invention may be selected from, but not limited to antigenic agents with molecular patterns associated with virus families Adenoviridae, Arenaviridae, Bunyaviridae, Coronaviridae, Filoviridae, Flaviviridae, Hepadnaviridae, Deltavirus, Caliciviridae, Herpesviridae, Orthomyxoviridae, Papovaviridae, Paramyxoviridae, Parvoviridae, Picornaviridae, Poxyviridae, Reoviridae, Retroviridae, Rhabdoviridae and Togaviridae.

Antigenic agents with molecular patterns associated with fungi and yeasts of the present invention may be selected from, but not limited to antigenic agents with molecular patterns associated with fungi and yeasts of the genus *Sporothrix, Aspergillus, Blastomyces, Candida, Coccidioides, Cryptococcus, Histoplasma* and *Pneumocystis*.

Antigenic agents with molecular patterns associated with protozoa of the present invention may be selected from, but not limited to antigenic agents with molecular patterns associated with protozoa of the genera *Cryptosporidium, Ciclospora, Entamoeba, Naegleria, Giardia, Leishmania, Plasmodium, Toxoplasma, Trichomonas, Trypanosoma*, microsporidia and *Isospora*.

Antigenic agents with molecular patterns associated with multicellular parasites of the present invention may be selected from, but not limited to antigenic agents with molecular patterns associated with multicellular parasites trematodes, cestodes and nematodes.

The antigenic agents of the present invention comprise protein, polysaccharide, lipid molecules and/or composite synthetic molecules that mimic protein, polysaccharide and/or lipid molecules.

More specifically, the agents of the invention comprise immune-active antigenic protein molecules which have enzyme activity, for example kinases, phosphatases, streptoquinases, estreptodornases and Deoxyribonucleases (e.g. dornases).

The immunogenic compositions for modulating the immune system of the present invention comprise from 0.001 to 500 micrograms per ml of each immunogenic agent.

Such immunogenic agents can be encapsulated in capsules, micro particles, nanoparticles, coated tablets, liposomes.

Specifically, the immunogenic compositions for modulating the immune system of the present invention comprise from 4 to 20 antigenic agents selected from the group consisting of antigens derived from agents: dornase, leveduriryeast, oidiomycin, PPD, prions, streptoquinase, *Streptococcus* toxoid, diphtheria toxoid, Tetanus toxoid, Koch's tuberculin, inactivated lysate of *Ascaris lumbricoides, Aspergillus* spp., *Aspergillus flavus, Aspergillus fumigatus, Aspergillus terreus, Candida* spp., *Candida albicans, Candida glabrata, Candida parapsilosis, Chlamydia* spp., *Chlamydia pneumoniae, Chlamydia psittaci, Chlamydia trachomatis, Cryptosporidium* spp., *Dermatophytes, Entamoeba hystolitica, Enterobius vermicularis, Enterococcus faecalis, Epidermophyton floccosum, Escherichia coli, Giardia lamblia, Haemophilus influenzae, Microsporum cannis, Mycobacterium* spp., *Mycobacterium bovis, Mycobacterium leprae, Mycobacterium tuberculosis, Neisseria gonorrhoeae*, human papilloma virus, Polio virus, *Proteus* spp., *Proteus mirabilis, Proteus penerii, Proteus vulgaris, Salmonella* spp., *Salmonella bongori, Salmonella enterica, Serratia* spp., *Serratia liquefaciens, Serratia marcencens, Shigella* spp. *Shigella flexneri, Shigella sonnei, Staphylococcus* spp., *Staphylococcus aureus, Staphylococcus epidermidis, Strongyloides stercoralis, Streptococcus* spp., *Streptococcus bovis, Streptococcus viridans, Streptococcus equinus, Streptococcus pneumoniae, Streptococcus pyogenes, Toxoplasma gondii, Trichomonas vaginalis*, trichophytin, *Trichophyton* spp; *Trichophyton rubrum, Trichophyton tonsurans, Trichophyton mentagrophytes*, yellow fever virus, hepatitis B virus, rubella virus, varicella zoster virus, variola virus, mumps virus, measles virus, herpes virus and vaccinia virus or synthetic analogues that present pathogen-associated molecular patterns (PAMPS) and/or danger-associated molecular patterns (DAMPS) associated with these antigenic agents.

In various embodiments, the immunogenic compositions for modulating the immune system of the present invention comprise 4, 5, 6, 7, 8, 9, 10, 11, 12, 13, 14, 15, 16, 17, 18, 19, or 20 antigenic agents selected from the group consisting of antigens derived from agents: dornase, yeast, oidiomycin, PPD, prions, streptoquinase, *Streptococcus* toxoid, diphtheria toxoid, Tetanus toxoid, Koch's tuberculin, inactivated lysate of *Ascaris lumbricoides, Aspergillus* spp., *Aspergillus flavus, Aspergillus fumigatus, Aspergillus terreus, Candida* spp., *Candida albicans, Candida glabrata, Candida parapsilosis, Chlamydia* spp., *Chlamydia pneumoniae, Chlamydia psittaci, Chlamydia trachomatis, Cryptosporidium* spp., *Dermatophytes, Entamoeba hystolitica, Enterobius vermicularis, Enterococcus faecalis, Epidermophyton floccosum, Escherichia coli, Giardia lamblia, Haemophilus influenzae, Microsporum cannis, Mycobacterium* spp., *Mycobacterium bovis, Mycobacterium leprae, Mycobacterium tuberculosis, Neisseria gonorrhoeae*, human papilloma virus, Polio virus, *Proteus* spp., *Proteus mirabilis, Proteus penerii, Proteus vulgaris, Salmonella* spp., *Salmonella bongori, Salmonella enterica, Serratia* spp., *Serratia liquefaciens, Serratia marcencens, Shigella* spp. *Shigella flexneri, Shigella sonnei, Staphylococcus* spp., *Staphylococcus aureus, Staphylococcus epidermidis, Strongyloides stercoralis, Streptococcus* spp., *Streptococcus bovis, Streptococcus viridans, Streptococcus equinus, Streptococcus pneumoniae, Streptococcus pyogenes, Toxoplasma gondii, Trichomonas vaginalis*, trichophytin, *Trichophyton* spp; *Trichophyton rubrum, Trichophyton tonsurans, Trichophyton mentagrophytes*, yellow fever virus, hepatitis B virus, rubella virus, varicella zoster virus, variola virus, mumps virus, measles virus, herpes virus and vaccinia virus or synthetic analogues that present pathogen-associated molecular patterns (PAMPS) and/or danger-associated molecular patterns (DAMPS) associated with these antigenic agents.

A preferred immunogenic composition of the invention comprises inactivated *Mycobacterium bovis* lysate, purified protein derivative of *M. tuberculosis*, inactivated *Staphylococcus aureus* lysate, inactivated *Staphylococcus epidermidis* lysate, inactivated *Steptococcus pyogenes* lysate, inactivated *Streptococcus pneumonia* lysate, inactivated *Enterococcus faecalis* lysate, Streptokinase/dornase, inactivated *Candida albicans* lysate, inactivated *Candida glabrata* lysate, inactivated *Epidermophyton floccosum* lysate, inactivated *Microsporum cannis* lysate, inactivated *Trichophyton mentagrophytes* of the *interdigitale* variety lysate, inactivated enteropathogenic *Escherichia coli* lysate, inactivated *Salmonella bongori* lysate, inactivated *Salmonella enterica* lysate and inactivated *Salmonella subterranea* lysate.

A preferred immunogenic composition of the invention comprising from 0.001 to 1 ng/ml of inactivated *Mycobacterium bovis* lysate, 0.001 to 1 ng/ml of purified protein derivative of *M. tuberculosis*, 0.1 to 100 µg/ml of inactivated *Staphylococcus aureus* lysate, 0.1 to 100 µg/ml of inactivated *Staphylococcus epidermidis* lysate; 0.1 to 100 µg/ml of inactivated *Steptococcus pyogenes* lysate; 0.1 to 100 µg/ml of inactivated *Streptococcus pneumonia* lysate; 0.1 to 100 µg/ml of inactivated *Enterococcus faecalis* lysate, 0.01 to 10 µg/ml of streptokinase, 0.01 to 10 µg/ml of dornase; 0.1 to 100 µg/ml of inactivated *Candida albicans* lysate; 0.1 to 100 µg/ml of inactivated *Candida glabrata* lysate, 0.1 to 100 µg/ml of inactivated *Epidermophyton floccosum* lysate; 0.1 to 100 µg/ml of inactivated *Microsporum cannis* lysate, 0.1 to 100 µg/ml of inactivated *Trichophyton mentagrophytes* of the *interdigitale* variety lysate; 0.1 to 100 µg/ml of inactivated enteropathogenic *Escherichia coli* lysate; 0.1 to 100 µg/ml inactivated *Salmonella bongori* lysate, 0.1 to 100 µg/ml inactivated *Salmonella enterica* lysate and 0.1 to 100 µg/ml of inactivated *Salmonella subterranea* lysate.

The compositions of the present invention can further comprise excipients, such as bactericides, bacteriostats, antioxidants, preservatives, buffers, stabilizers, pH adjusters, osmolarity adjusters, antifoaming agents and surfactants, and residual antigen inactivating or fractionation agents, growth medium components and solvents commonly used in the production of vaccines and immunotherapies.

The compositions of the present invention may be a solid, liquid or gel. As used herein, the use of the term "pharmaceutically acceptable carrier" means a non-toxic solid, inert, semi-solid liquid excipient, diluent, auxiliary formulation of any type, or simply a sterile aqueous solution such as saline. Some examples of materials which can serve as pharmaceutically acceptable carriers are sugars such as lactose, glucose and sucrose, starches such as corn starch and potato starch, cellulose and its derivatives such as sodium carboxymethyl cellulose, a ethyl cellulose and cellulose acetate, cyclodextrin; oils such as peanut oil, cottonseed oil, sunflower oil, sesame oil, olive oil, corn oil and soya bean oil, glycols such as propylene glycol, polyols, such as glycerol, sorbitol, mannitol and polyethylene esters such as ethyl laurate, ethyl oleate, agar, buffering agents such as aluminum hydroxide and magnesium hydroxide, alginic acid, pyrogen-free water, isotonic saline, Ringer's solution, buffer solutions of ethyl alcohol and phosphate as well as other non-toxic compatible substances used in pharmaceutical formulations.

A variety of administration routes in animals or humans for the immunotherapeutic compositions and vaccines described herein are available. The particular selected mode, will depend on the selected antigenic agents, the dosage required for therapeutic efficacy and patient to whom the composition is administered. The methods of the present invention can generally be practiced using any mode of administration biologically acceptable, i.e., any means that produces effective levels of immune response without causing clinically adverse reactions. Such modes of administration include intradermal, oral, rectal, sublingual, topical, nasal, transdermal or parenteral administration. The term "parenteral" includes subcutaneous, intravenous, epidural, irrigation, intramuscular, release pumps or infusion. In particular, in this invention, oral, intradermal, parenteral, subcutaneous, intravenous, intramuscular, and, by the nasal mucosa and/or oral administration are preferred for administration of the compositions claimed herein.

For parenteral administration, the active ingredients may also be dissolved in a pharmaceutical carrier and administered as a solution, emulsion, including micro- and nanoemulsions or suspension. Examples of suitable carriers are water, saline, dextrose solutions, fructose solutions or oils of animal, vegetable or synthetic origin. Other vehicles may also contain other ingredients, for example, preservatives, suspending agents, solubilizing agents, buffers and the like.

In a second embodiment, the invention refers to a method to treat sepsis in a human or an animal who has a bacterial infection comprising administering to the human or animal an effective amount of one or more antibiotics and one or more immunogenic compositions for modulating the immune system comprising a therapeutically effective amount of three or more (e.g., 3, 4, 5, 6, 7, 8, 9, 10, 11, 12, 13, 14, 15, 16, 17, 18, 19, or 20 or more) synthetic antigenic agents or natural antigenic agents, or fractions and combinations thereof, comprising pathogen-associated molecular patterns (PAMPS) and/or danger associated molecular patterns (DAMPS) selected from at least two groups consisting of: (A) antigenic agents with molecular patterns associated with bacteria, (B) antigenic agents with molecular patterns associated with viruses, (C) antigenic agents with molecular patterns associated with fungi and yeasts, (D) antigenic agents with molecular patterns associated with protozoa, (E) antigenic agents with molecular patterns associated with helminthes, and (F) antigenic agents with molecular patterns associated with prions; and one or more physiologically acceptable carriers, excipients, diluents or solvents.

Septicemia is defined as an extremely serious infection in which one or more bacteria or microorganisms, from their entry point, enter the bloodstream and start circulating in large numbers, getting established at distant points, colonizing tissues, organs, and in the most severe cases, can successively reach most of the body surface and causing sepsis as a generalized inflammation that compromise the circulatory system. Generally, when the microorganism load is too large, a large number of bacteria, with their toxic and metabolic products, with countless PAMPS and DAMPS, stress signals touching with all the also countless PRRs and RDPs stress signal receptors of most of the body surface, while generating an extensive, intense and violent general inflammatory process, with the massive release of cytokines (cytokine storm) from the translation of all these signs.

The unfavorable evolution of septicemia leads to sepsis, through the massive release of pro-inflammatory cytokines such as TNFs, IL1, IL18, IL6 and others, causing an inflammatory collapse with hemodynamic characteristic alterations, such as hypotension, rapid pulse, which may culminate in septic severe shock, usually irreversible. Septicemia, sepsis are serious infections/inflammations with high morbidity and mortality. In these severe infections/inflammation syndrome the immune system, in turn, with its compromised operability by weaknesses and blockages induced by bacteria, starts to act so as to eliminate the bacteria at any cost, through the cytokine storm and through the inflammatory Th17 tissue profile, increasing inflammation disproportionately and therefore harming the organism (33).

In this inflammatory tissue profile, the effector loops of innate immunity, controlled by the TCD4 lymphocytes, cause tissue damage and sometimes massive destruction, that compromise organs and tissues and that exacerbate infections, leading, for example, to respiratory failure, lung shock, and in ARDS (adult respiratory distress syndrome), also leading to renal failure and multiple organ failure.

Therefore, in septicemia, in sepsis and in septic shock there are two variables that should strategically be considered and should be the target of an immunotherapy, so it is successful. These two variables are the huge inflammation by the cytokine storm caused by the massive spread of countless bacteria in the whole body and its connection with the PRRs, DPPs, and stress signals in DCs and sentinels cells that induce polarization for the Th17 profile caused by the functional infeasibility of the Th1 and Th2 profiles and described inflammation settings. These variables are the cornerstone of severity, gravity, morbidity and mortality of these diseases.

Taking into account, these two variables, for an immunotherapy to be effective in these infections, it should be applied to cover the entire body surface, including the greatest number of lymphatic territories to geographically overlap with the action of the pathogen or pathogens. It should also be applied to the injured areas and to the perilesional region so that together they can cause widespread recontextualization, that by its action can recover the integrity of the T loop and produce a wide, extensive and intensive, anti-inflammatory effect by effector/memory T cells generated within the application sites. It should, in parallel, through the recontextualization and reprogramming above described with huge anti-inflammatory effect by inhibiting and decreasing cytokine storm, polarize the TCD4 response of the Th17 inflammatory tissue profile for the humoral TH2 and cell TH1 profiles, further decreasing the generalized inflammation by the action of memory cells the only cells in the body capable to abrogate physiologically huge inflammations.

IF used the loop amplification by IL2 should be very low, just enough to specifically amplify the repolarization of the immune response of the inflammatory profile to the immunity profile or to Treg/TRI regulatory profile.

Thus, the recontextualizing and the reprogramming achieved by immunotherapy using the compositions of the present invention to achieve a new perceived identity of the pathogen, by recovering immune cells through the anti-inflammatory action of non-related specific memory T lymphocytes, by the inhibition of the cytokine storm and also by the repolarization of the tissue inflammatory profile TH17 to elective and effective TH1 and TH2 immunity profiles, will together redirect the immune response. This immune response, renewed in real time during the infectious process, in conjunction with a biological balance shifter, in the case of the use of various antimicrobial agents, have a chance to reverse the biological equilibrium at the end of the curve in which is very favorable for the microorganism, to be favorable to the host and now have a chance of solution.

Adequacy of the protocol to the "status" of the immune system in the pathology and in the patient, being treated.

In the case of septicemia and sepsis, by the own pathophysiological mechanisms, there is a breach of the integrity and functionality of the T loop with an inadequate polarization for a suppressing TREG profile in cancer and for an cytokine storm and inflammatory tissue Th17 profile in sepsis with a nearly complete inoperability of the immune system overcome by disease. In these cases, as in the examples cited herein, the recontextualizing induced by the best available secondary achieved activation of the new perceived identity of the pathogen must reach the whole body to reverse all immunosuppression, tolerance and immune ignorance induced by the pathology, as well as to restore all operational and functional capacity of the immune system to have a reprogrammed and renewed effective immune response.

In a third embodiment, the invention refers to a method to treat multi resistant bacteria infection in a human or an animal who has a bacterial infection comprising administering to the human or animal an effective amount of one or more antibiotics and one or more immunogenic compositions for modulating the immune system comprising a therapeutically effective amount of three or more (e.g., 3, 4, 5, 6, 7, 8, 9, 10, 11, 12, 13, 14, 15, 16, 17, 18, 19, or 20 or more) synthetic antigenic agents or natural antigenic agents, or fractions and combinations thereof, comprising pathogen-associated molecular patterns (PAMPS) and/or danger associated molecular patterns (DAMPS) selected from at least two groups consisting of: (A) antigenic agents with molecular patterns associated with bacteria, (B) antigenic agents with molecular patterns associated with viruses, (C) antigenic agents with molecular patterns associated with fungi and yeasts, (D) antigenic agents with molecular patterns associated with protozoa, (E) antigenic agents with molecular patterns associated with helminthes, and (F) antigenic agents with molecular patterns associated with prions; and one or more physiologically acceptable carriers, excipients, diluents or solvents.

In a fourth embodiment, the invention refers to a method to modulate an immune system response in a human or an animal who has a bacterial infection comprising administering to the human or animal an effective amount of one or more immunogenic compositions for modulating the immune system comprising a therapeutically effective amount of three or more (e.g., 3, 4, 5, 6, 7, 8, 9, 10, 11, 12, 13, 14, 15, 16, 17, 18, 19, or 20 or more) synthetic antigenic agents or natural antigenic agents, or fractions and combinations thereof, comprising pathogen-associated molecular patterns (PAMPS) and/or danger associated molecular patterns (DAMPS) selected from at least two groups consisting of: (A) antigenic agents with molecular patterns associated with bacteria, (B) antigenic agents with molecular patterns associated with viruses, (C) antigenic agents with molecular patterns associated with fungi and yeasts, (D) antigenic agents with molecular patterns associated with protozoa, (E) antigenic agents with molecular patterns associated with helminthes, and (F) antigenic agents with molecular patterns associated with prions; and one or more physiologically acceptable carriers, excipients, diluents or solvents.

It is other aspects, the present invention refers to the use of immunogenic compositions in the manufacture of medicaments and kits for preventing and/or treating of infectious diseases. Immunogenic compositions of the invention are also may also be used in the prevention and/or treatment of infectious diseases in association with one or more antibiotics.

Properties of the Immunogenic Compositions of the Present Invention

The immunogenic compositions of the present invention have an unexpected effect on the immune response. As can be seen in the Examples below, the immunogenic compositions of the present invention show an unexpected technical effect of causing an immune response that involves resetting, recontextualizing, leading back, renewing and reprogramming the immune response in real time.

More specifically, the immunotherapeutic compositions of the present invention by creating a new identity of the pathogen perceived by innate and adaptive immunological system are capable of provoking a reset, a recontextualization a lead back of the operational action capacity of the immune system by changing the relationship of forces against the aggressors in its favor, giving the immune system a competitive advantage, which does not occur spontaneously in the evolution of disease. This recontextualization determines a consequent renewal and reprogramming of the established immune response or incipiently established, or erroneously established mistakenly attacking in a dysautonomical way the human or animal body, polarizing the primary pro-inflammatory response that is always a fortuitous reply possible to be improved to a secondary, active anti-inflammatory, more effective and appropriate immune response.

This effect occurs via secondary stimulation, activation and joint action of certain components of the immune system, such as sentinel cells, antigen presenting sentinel cells, and memory lymphocytes. Specifically, the compositions of this invention properly reset the activated sentinel cells, the activated dendritic cells and other activated APC cells, by the action of memory cells, generating a new degree and intensity of CD4 T cell with a secondary activation profile that turn to a secondary effective standard the degree and intensity of the immune profile to properly treat the infection without causing immunological side-effects, such as inflammation.

Accordingly, the immunomodulatory antigenic compositions of the present invention, when in larger or significant amounts completely change the perceived image of the pathogen and trigger a specific secondary active adaptive immune response, desired to treat bacterial, viral or parasitic infections with a low inflammatory profile.

In addition, the treatment with the immunogenic compositions of the present invention is capable of stimulating the regenerative power of the immune system, a natural physiological property of this system providing a subsequent effect to the elimination of infectious disease and other diseases: to recover cells and tissues, by restoring organ function debilitated from trauma and damage which cause the loss of part of the organism. This property was demonstrated in the clinical cases of irreversible sepsis reported in the Examples. The patients had recovery and regeneration of complex trauma wounds with important tissue loss, organ destruction in lungs, kidneys, liver, bones and extremities induced by CIVD, and ischemic events by low blood flow and toxicity.

Thus, the immunogenic compositions of the present invention are able to mobilize the immune system and lead to an increased regenerative power of the body, through mobilization of stem cells or the activation of gene sets which allow the regeneration of cells and tissues and can even reconstruct organs and their functions, and can reconstitute organic systems such as the vascular system, the nervous system and the endocrine system, among others.

As can be seen in the Examples presented below, the immunogenic compositions of the present invention exhibit an unexpected technical effect of recontextualizing, renewing, and reprogramming the immune response in real time and consequently significant cure rates when compared to drugs and methodologies in the art.

In a first embodiment of the invention, immuno-modulator agent(s) is/are used for preparing an immunotherapy pharmaceutical composition capable of inducing a new innate secondary immune response, which triggers a cascade of immune events, including the main event of activation of memory lymphocytes from the agent(s) inoculated by human intervention and the concomitant activation by antigens present in the patient's own body, resulting in a recontextualization, renewal lead back and reprogramming of the ongoing immune response to a particular established disease (or still in the establishment phase), generating an adaptive secondary response specific to this disease effectively, allowing combating the pathogen in an anti-inflammatory way. As such, the administration of the composition containing the agents of the present invention repolarizes or improves the polarization of the immune system in the presence of a disease when the established polarization is inadequate, by the action of the etiologic agent or colonizer. The activities of the agents of the present invention affect the shape, time, accuracy and polarization of the immune response, preferably leading to an secondary innate and adaptive immune response that it is more effective to fight the disease, leading to a better reaction of organism itself.

The present invention provides methods to treat bacterial and other microbial infections with the use of the antigenic combinations described. The present invention also provides for the possibility of adding traditional therapies to the agents of this invention, aiding the process of elimination of the etiological heterologous invading agents and of the colonizing autologous cells, through the real therapeutic potential of antimicrobial drugs, selective for the pathogens and other infectious agents. This is made possible by the principle of displacement of the biological equilibrium in favor of the patient in combination with a correct polarization of the immune response as described herein.

When the immune stimulation follows a situation of immune response, after the termination of the disease mechanism or aggression, the continued activation of the immune system by antigens or immunomodulatory agents of the present invention leads, through the activation of stem cells, to the regeneration of tissues, organs and systems, by mechanisms not yet fully understood, but related to healing or restitution ad integrum mechanisms observed in various medical situations.

The compositions of the present invention allow the recruiting of the maximum number memory cells, new effective virgin cells of the individual, producing more significant effects than an antibody increase as described in the prior art. The use of multiple antigenic agents with distinct enough PAMPS, DAMPS and stress signals to simulate different types of attacks that the organism suffers and to which the organism has already immunologic memory of, be it by environmental exposure or vaccination programs, allows a wider recruitment of memory cells and new effective virgins cells, enabling real-time recontextualization, resetting and leading back of the immune response and thus potentially and radically altering the type of immune response and disease or illness progression that affects the individual in a positive, and in several cases, such amazing way as compared to the prior art. Furthermore, the present invention, unlike the prior art, applies a greater and diverse amount of bacterial components, having representatives of both intracellular and extracellular bacteria in the composition, besides components of viruses, parasites, fungi and yeasts.

The present invention encompasses more areas of the body and tissues that have sentinel and APC cells, and preferably looks for exposure on locations close to the infection sites and other distal applications to the disease sites (as is the case in disorders or diseases that manifest themselves in specific locations of the body) to secondary reset innate system in all the places of the disease. The compositions of the present invention, when applied according to the process of using the present invention in one or, usually, at various strategic of body regions drained by lymphoid territories or primary and/or secondary lymphoid organs, or even intralesional, are perceived by the PRRs (pathogen-associated pattern recognition receptors) off all sentinel cells of the body.

Thus, the present invention employs immunomodulatory agents in amounts, concentrations and specific locations to recontextualize, reset and lead back the immune system, activating and redirecting the mechanisms for tissue repair and regeneration, as occurs during healing and regeneration of tissue, organ or system, leading to a "restitution ad integrum" or reconstitution with scar. This repair is usually triggered at the end of an immune response process, after healing the infection.

Use of the Immunogenic Compositions of the Present Invention.

Considering the properties of the immunogenic compositions of the present invention, it constitutes another aspect of the present invention using the immunogenic compositions in the manufacture of medicaments for the prevention and/or treatment of infectious diseases.

These infectious diseases can be of viral, bacterial, fungal or parasitic origin.

Diseases of viral origin prevented and/or treated by the immunogenic compositions of the present invention can be caused by the following viruses but not limited to:

HIV, hepatitis virus, herpes virus, rhabdovirus, rubella virus, smallpox virus, poxvirus, and Morbillivirus paramyxovirus.

Diseases of bacterial origin prevented and/or treated by the immunogenic compositions of the present invention may be caused by the following bacteria, but not limited to, *Pneumococcus, Staphylococcus, Bacillus, Streptococcus, Meningococcus, Gonococcus, Escherichia, Klebsiella, Proteus, Pseudomonas, Salmonella, Shigella, Haemophilus, Yersinia, Listeria, Corynebacterium, Vibrio, Clostridia, Chlamydia, Mycobacterium, Treponema*, and *Helicobacter*.

Fungal diseases prevented and/or treated by the immunogenic compositions of the present invention may be caused by the following fungi but not limited to: *Candida, Aspergillus, Cryptococcus neoformans*, and/or fungi that cause superficial and deep mycosis. Diseases caused by parasites are caused by the following parasites: *Trypanosoma, Schistosoma, Leishmania*, amoebas and tapeworm.

In one embodiment of the invention, the compositions of the present invention are administered once, in one area of the body or in different sites in order to redirect the immune system with the highest possible efficiency.

The use of the immunogenic compositions of the present invention for modulation of the immune system, involving the exposure of part or all of the system for recognition of antigens in the immune system, such as dendritic cells, macrophages and lymph nodes from different parts of the body, inflammatory territories will depend on the goal imposed by the illness being fought, and occurs preferentially through injections or use of guns, or delivery systems or controlled infusion or pulsed cells with in vitro antigens. The agent may be applied to only one location in the body or in several tens of locations in several forms: subcutaneous, muscular, intravenous, oral, breathable aerosol, cutaneous (dermal patches) in organs, the viscera, or specific tissues, or in different body cavities, which can vary in number from one to one hundred (100) applications in one to fifty (50) sessions.

The antigenic compositions of this invention may also be combined with other drugs that can weaken the reproduction, growth, or any other form of strengthening of the disease's causative agent, causing a shift of the equilibrium in favor of the biological immune defenses of the host, animal or human. Or still in concomitant treatment.

The antigenic compositions of this invention may also be combined with other procedures such as, but not limited to, antibiotics chemotherapy, therapy with antibodies and antisera, using hormones or other physiology modulating agents (cytokines, chemokines, neurohormones, peptides), treatment with antiviral agents, use of herbal medicines, vitamin supplementation, methods of therapeutic or prophylactic vaccination (with or without cells and not limited to the type of vaccine vehicles), gene therapy, surgery or homeopathy, depending on the disease or illness being fought related to an improper or inefficient immune activity.

Recontextualizing, Resetting, Renewing, Leading Back and Reprogramming the Immune Response.

Recontextualizing and resetting the immune system, as explained in the text of this patent application, is achieved by means of stimulation of the immune system by antigens of different pathogens not related to the pathology to be treated, for which the human or animal, preferably, already has an immunological memory for totally changing the inner perceived primary image of the invader pathogen to a new secondary effective proactively induced one.

These varied and multiple antigens, in number greater than five, with multiple PAMPs DAMPs and SRS induce in the sentinel cells and in the APC cells, especially in dendritic cells, an intense secondary activation allowing the mobilization of these memory CD4 and also CD8 memory or eventually NK memory cells and lymphocytes specific for these antigens at the site of application.

These stimuli must be capable of causing an intense, strong and effective secondary specific immune response to these antigens of the new identity at the site of application, in the regional activated lymph nodes, in the lymph nodes at a distance and a systemic mobilization of the immune system so that it can, in parallel, cause an effective secondary response capable of eradicating the specific pathology in progress.

The innate and adaptive secondary immune response caused intentionally by the composition of the present invention should encompass the full extent of the body area affected by the condition being treated and even exceed it if possible to be able to activate the sentinel and APC cells in the number and intensity that would be needed to properly address the aggression caused by the pathogenic disease to be treated, and activating and triggering the best specific adaptive secondary response, effectively and properly sequentially polarized, in order to cure the condition being treated.

Thus, the innate and adaptive response induced by the present invention will geographically overlap the condition being treated and by its intense and extensive secondary activation will correct the inefficient activation, purposely limited by the action of the pathogen that overcomes the body's defenses, by preventing competition, its proper mobilization and development of an effective adaptive response according to its greatest genetic and biological potential. This ideal activation should also reverse the immunosuppression, the tolerance and escape mechanisms established by pathogens because it is known and proven that an unrelated strong and intense immune response, that fully covers the response to be corrected, through the activated cells and cytokines of the immune system, will correct these deficiency situations efficiently.

Effector cells and memories of specific antigens of the present invention, activated and generated at the site of application of the antigens, will, via the bloodstream, enter the already activated lymph nodes by HEVs, which drain the region affected by the disease and will enable, in a strong and intense way induce the activation of all the existing dendritic cells there. Therefore, they will lead to an activation of the entire lymph node, causing it to grow with increased irrigation, increasing its size and making it a reactional lymph node capable of provoking an immune response against weak antigens, which by themselves are not capable of causing an immune response. PAMPs alone can remodel lymph node feed arteriole and induce lymph node hypertrophy that is essential for an effective primary adaptive response and also for secondary immune responses This adjuvant effect, well known and demonstrated experimentally and clinically, of the effector/memory T lymphocytes, will oppose the action of the target causative agent that is blocking the required activation of the lymph node for the development of an immune response that is necessary to treat the disease in question. That, exclusively for the purpose and by the action of the present invention, through its potent antigenic composition, may occur that the sentinel cells and dendritic cells and macrophages of the immune response will be the same for unrelated antigens and to the pathological antigens, but from this action, will be intensely and properly activated. Dendritic cells strongly activated by multiple antigens, have a slow metabolism and ideally present all dominant and subdominant epitopes of the causative agent, by the known "helper" effect, mobilizing all possible and available T lymphocytes able to specifically recognize antigens of the autologous or heterologous pathogen, to be treated and to react against it.

The areas of the inflammatory process and lymphatic territories are exactly the same. The inflamed area, through the anti-inflammatory action of specific memory cells, unrelated, mobilized by the present invention by their antigenic composition, will block the inflammasomes and exert an anti-inflammatory action that will correct the pathological inflammation responsible for the morbidity of the disease and which was caused by its etiological agent. For the memory effect it's important to note that this known action of the memory T cells is the major responsible for the fact that a second contact with any pathological agent, after an already established immunity, is asymptomatic, without causing a disease.

The lymphatic territories are exactly the same, only now intensely activated and with the necessary alarm signal, caused by the present invention, to cause any immune response, even for a weak antigen, similar to what occurs with dendritic cells common to this invention and to the autologous or heterologous etiological agent to be fought. Lymphokines and innate cells that command an effective secondary response will be the same and the T lymphocytes specific against the etiologic agent to be fought, will "hitch a ride" on this ideal microenvironment for holding an effective immune response.

The dendritic cells activated by the present invention, can capture the antigens of the etiological agent to be fought at the site of the pathology and in the related lymphatic territories and be in contact with the pathogen specific TCD4 lymphocytes, in a correctly and ideally enabled lymphatic system. The role of the dendritic cells activated and matured with the TCD4 specific to the etiologic agent, occurs in a microenvironment conducive to conducting an immune response, with all the genetic and biological potential of the host organism's immune system.

These dendritic cells at the site of the pathology and at the lymph nodes will properly gauge the severity, extent, intensity and type of aggression, activating, inducing, coordinating, polarizing, leading and maintaining a new effective adaptive immune response, whose effector loop, with the collaboration of the cells and effector molecules of the intense and properly activated innate immunity may be able to eliminate the causative agent to be fought. So the answer is reprogrammed and lead back as noted above, reversing the biological balance in favor of the host, which until then was under the yoke of the offending autologous or heterologous agent.

Such action may occur with or without the help of biological balance shifters such as antibiotics drugs, capable to block, weaken or neutralize the effects and potential of the etiological agent, allowing the immune system to have a chance to heal the pathology that is the target of the treatment. Once triggered by any etiological agent, the immune system will only stop responding when the etiological agent is eliminated or the organism passes away, this way the invention will help avoid the latter option, or it will improve the patient's condition if there is a chronic disease that cannot be cured.

Thus, the action of the compositions of the present invention intentionally and strategically superimposed over the entire area under the action of the agent to be fought, will recontextualize the immune system by activating the PAMPs and DAMPs in the sentinel cells and common APCs and by the unrelated specific secondary adaptive immune response. This intentionally induced immune response will efficiently activate the whole lymphatic territory and the organic territory affected by the etiological agent. In the recontextualized area and in the bulge, and within the context of a greater immune response, stronger, more intense and more extensive secondary anti-inflammatory nature of the target immune response will be, as described, reprogrammed and efficiently renewed within the scope of a greater chance for the host, now with a chance of reversing the biological balance in its favor.

Rationale of the Therapeutic Protocol

The therapeutic protocol of the present invention designed to be applied in cases of bacterial infection and septicemia must:

- be applied in most strategic lymphatic regions of the body or infection. In the cases described herein, more than 10 lymphatic territories have been hit. It must be applied within the infected and perilesional areas.
- the immunotherapy formulation must contain at least 5 antigens so it contains PAMPs and DAMPs so as to be able to recontextualize the immune system.
- the application area must overlap, cover, and overcome the whole extension of regions dominated by the infection.
- the antigenic stimuli must be repeated every 4 or 5 days in order to avoid the generation of suppressor cells capable of aborting the new desired immune response or to suppress an achieved repolarization.
- the treatment must be maintained in this manner until the end of the infection, or to the healing of the wound, organ or system.
- in practice, 1 to 3 ml of this immunotherapy must be applied to 10 or more lymphatic territories. This invention should be jointly applied in intra and extra lesion areas damaged by infection.

In summary, the immunotherapy is "systemically" distributed in several (at least ten) lymphatic territories, peri- and intra-lesion with a volume able to disrupt and destabilize the lesion from the domination of its micro and macro environment, or cover the area significantly affected by infection and inflammation, as well as to restore the microenvironment that is favorable to the immune response of the organism. It will be applied every 4 to 5 days.

In sepsis, severe sepsis and septic shock, the use of low doses of exogenous interleukin-2 should be avoided. The use of low doses of exogenous interleukin-2 in severe infections uninterruptedly should be carefully evaluated when a amplification of the immune loop is needed.

DESCRIPTION OF THE FIGURES

The following figures are part of this report and are included here to illustrate certain aspects of the invention.

The object of the present invention may be better understood by reference to one or more of these figures in combination with the detailed description of the preferred embodiment presented here.

EXAMPLES

Figure 1:
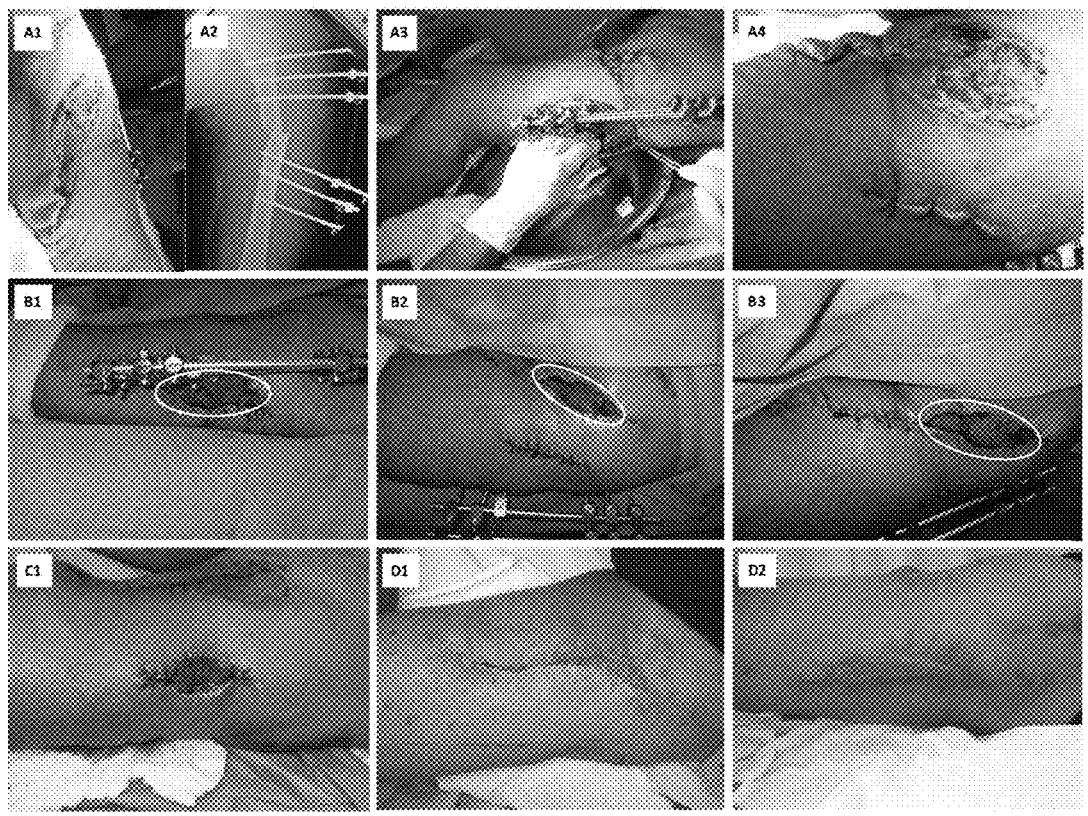
FIG. 1 shows images of Example 2. A1, A3 and A4 show wounds after surgical cleaning on Jan. 29, 2011. It's possible to notice injury of polytrauma associated with sepsis caused by multi-resistant strain and major tissue loss that continued to perform poorly with a winy general appearance without any appearance of healthy granulation tissue. It is possible identifying, in X-Ray on Jan. 29, 2011 (A2) the external fixation of the femur after surgical procedure. On Feb. 2, 2011 (5 days after starting the treatment) the patient presented complete recovery from sepsis and received ICU discharge (B1, B2 and B3). In B1 to B3 it is possible to identify healthy granulation tissue characteristic of the second intention healing process. In C1 (1 Mar. 2011) it's clear the improvement of the leg injuries described in A1-A4, that's the reason why patient was discharged from hospital on 15 Mar. 2011. In D1 (medial site) and D2 (lateral site) is possible to verify the complete recovery from complex wound of polytrauma associated with: severe sepsis caused by multidrug-resistant *Acinetobacter baunnamii* and osteomyelitis. These data strongly suggest a decisive role of the DECA immunotherapy, associated with debridement and antibiotics, to cure the clinical scenario, in a relatively short time, making possible not only the patient survives a natural disaster but also walk again without crutch or cane.

In order to allow a better understanding of the invention and clearly demonstrate the technical progress achieved, the results of the various tests conducted with respect to this invention are shown below as examples.

These Examples are presented for illustrative purposes only and should not be regarded in any way as limiting the scope and range of the invention.

Example 1: Immunogenic Compositions

In order to achieve the recontextualizing, renewal and reprogramming of the immune response in real time according to the innovative concepts described in the present invention, an expert skilled in the art can design different and distinct compositions, combinations or formulations of products, which fall within the scope of the invention.

As described, for such compositions to meet the technical requirements for the advantageous or unpublished results in treat a number of diseases and illnesses, they must have a high diversity of antigens from pathogens, so as to get the maximum synergistic effect in binding the PAMPs and DAMPs to their receptors and allowing the achievement of a high degree of activation of the innate immunity in the sentinel cells (with or without ATC function) thereby allowing the recontextualizing, renewal and reprogramming of the immune response in real time.

Such compositions should preferably use antigenic agents for which most people, because of previous contact, would have memory clones of in their immune system capable of inducing a broad anti-inflammatory action in parallel to recontextualization. For this, antigenic agents should preferably be selected that:

correspond to the most common infections contracted by the individual from childhood to maturity (when the animal or the human being acquires its "repertoire of immunity").

are used in immunization programs such as childhood vaccination programs against endemic and/or epidemic diseases.

those from organisms of potentially pathogenic microflora, especially of the gastrointestinal tract, where the memory lymphocytes play an active dynamic barrier ensuring the survival of the individual.

Ideally each of the antigenic agents should be present in a concentration of 0.001 to 500 micrograms per mL.

In accordance with these concepts, several formulations have been developed, using antigenic agents in their already available, safe, and approved forms for use in human vaccination programs or allergic response tests and immunity assessment tests.

Therefore, we present the following several examples of compositions which fall within the scope of the present invention, without however the intention to limit it, since the present invention and its concepts allow for the design of immunogenic compositions comprising a very large number of combinations of antigenic agents.

Composition 1a (DECA Composition):

| Component | Concentration |
|---|---|
| Koch's Turberculin (inactivated *Mycobacterium bovis* lysate). | 0.004 ng/mL |
| PPD | 0.004 g/mL |
| Inactivated *Staphylococcus* lysate (*Staphylococcus aureus* and *Staphylococcus epidermidis* in equal parts). | 6.94 μg/mL |
| Inactivated *Steptococcus* lysate (*Streptococcus pyogenes*, *Streptococcus pneumoniae* and *Enterococcus faecalis* in equal parts). | 6.94 μg/mL |
| Streptokinase derived from inactivated beta-hemolytic *Streptococcus* lysate purification. | 0.444 μg/mL |
| Dornase derived from inactivated beta-hemolytic *Streptococcus* lysate purification. | 0.111 μg/mL |
| Inactivated *Candida* lysate (*Candida albicans* and *Candida glabrata* in equal parts). | 6.94 μg/mL |
| Inactivated dermatophytes lysate (*Epidermophytonfloccosum*, *Microsporum cannis*, *Trichophyton mentagrophytes* of the interdigitale variety in equal parts). | 6.94 μg/mL |
| Inactivated enteropathogenic *Escherichia coli* lysate (EPEC) | 6.94 μg/mL |
| Inactivated *Salmonella* lysate (*Salmonella bongori*, *Salmonella enterica* and *Salmonella subterranea* in equal parts). | 6.94 μg/mL |
| Sodium Chloride | 7.5 mg/mL |
| Sodium phosphate dibasic heptahydrate | 0.48 mg/mL |
| Potassium phosphate monobasic | 0.06 mg/mL |
| Phenol | 2.5 mg/mL |
| Water | q.s. |

Composition 1b (VITER Composition):

| Component | Concentration |
|---|---|
| Koch's Turberculin (inactivated *Mycobacterium bovis* lysate). | 0.0036 ng/mL |
| PPD | 0.0036 μg/mL |
| Inactivated *Staphylococcus* lysate (*Staphylococcus aureus* and *Staphylococcus epidermidis* in equal parts). | 6.31 μg/mL |
| Inactivated *Steptococcus* lysate (*Streptococcus pyogenes*, *Streptococcus pneumoniae* and *Enterococcus faecalis* in equal parts). | 6.31 μg/ml |
| Streptokinase derived from inactivated beta-hemolytic *Streptococcus* lysate purification. | 0.404 μg/mL |
| Dornase derived from inactivated beta-hemolytic *Streptococcus* lysate purification. | 0.101 μg/mL |
| Oidiomycin (antigenic extract of *Candida albicans* | 6.31 μg/mL |
| Trichophytin (antigenic extract of *Tricophyton* sp | 6.31 μg/mL |
| Inactivated enteropathogenic *Escherichia coli* lysate (EPEC) | 6.31 μg/mL |
| Inactivated *Salmonella* lysate (*Salmonella bongori*, *Salmonella enterica* and *Salmonella subterranea* in equal parts). | 6.31 μg/mL |
| Attenuated yellow fever virus strain 17 D204 | 20 μg/mL |
| Sodium Chloride | 7.5 mg/mL |

-continued

| Component | Concentration |
|---|---|
| Sodium phosphate dibasic heptahydrate | 0.48 mg/mL |
| Potassium phosphate monobasic | 0.06 mg/mL |
| Phenol | 2.5 mg/mL |
| Water | q.s. |

Composition 2:

| Component | Concentration |
|---|---|
| Koch's Turberculin (inactivated *Mycobacterium bovis* lysate). | 0.004 ng/mL |
| PPD | 0.004 g/mL |
| Inactivated *Staphylococcus aureus* lysate, inactivated *Staphylococcus epidermidis* lysate in equal parts. | 6.94 µg/mL |
| Streptokinase derived from inactivated beta-hemolytic *Streptococcus* lysate purification. | 0.444 µg/mL |
| Dornase derived from inactivated beta-hemolytic *Streptococcus* lysate purification. | 0.111 µg/mL |
| Inactivated *Candida albicans* lysate, inactivated *Candida parapsilosis* lysate, inactivated *Candida glabrata* in equal parts. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Sodium Chloride | 7.5 mg/mL |
| Sodium phosphate dibasic heptahydrate | 0.48 mg/mL |
| Potassium phosphate monobasic | 0.06 mg/mL |
| Phenol | 2.5 mg/mL |
| Water | q.s. |

Composition 3:

| Component | Concentration |
|---|---|
| PPD | 0.004 g/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Staphylococcus aureus* lysate, inactivated *Staphylococcus epidermidis* lysate in equal parts. | 6.94 µg/mL |
| Inactivated *Candida albicans* lysate, inactivated *Candida parapsilosis* lysate, inactivated *Candida glabrata* lysate in equal parts. | 6.94 µg/mL |
| Sodium Chloride | 7.5 mg/mL |
| Sodium phosphate dibasic heptahydrate | 0.48 mg/mL |
| Potassium phosphate monobasic | 0.06 mg/mL |
| Phenol | 2.5 mg/mL |
| Water | q.s. |

Composition 4:

| Component | Concentration |
|---|---|
| Inactivated BCG lysate | 50 mg/mL |
| Inactivated *Staphylococcus aureus* lysate, inactivated *Staphylococcus epidermidis* lysate in equal parts. | 6.94 µg/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 µg/mL |
| Inactivated *Candida albicans* lysate, inactivated *Candida parapsilosis* lysate, inactivated *Candida glabrata* in equal parts. | 6.94 µg/mL |
| Sodium Chloride | 7.5 mg/mL |
| Sodium phosphate dibasic heptahydrate | 0.48 mg/mL |
| Potassium phosphate monobasic | 0.06 mg/mL |
| Phenol | 2.5 mg/mL |
| Water | q.s. |

Composition 5:

| Component | Concentration |
|---|---|
| PPD | 0.004 g/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Apergillus fumigatus*, *Apergillus flavus*, and *Apergillus terreus* lysate in equal parts. | 6.94 µg/mL |
| Inactivated dermatophytes lysate (*Epidermophytonfloccosum*, *Microsporum cannis*, *Trichophyton mentagrophytes* of the interdigitale variety in equal parts). | 6.94 µg/mL |
| Sodium Chloride | 7.5 mg/mL |
| Sodium phosphate dibasic heptahydrate | 0.48 mg/mL |
| Potassium phosphate monobasic | 0.06 mg/mL |
| Phenol | 2.5 mg/mL |
| Water | q.s. |

Composition 6:

| Component | Concentration |
|---|---|
| Koch's Turberculin (inactivated *Mycobacterium bovis* lysate). | 0.004 ng/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Neisseria meningitides* lysate. | 6.94 µg/mL |
| Inactivated *Apergillus fumigatus*, *Apergillus flavus*, and *Apergillus terreus* lysate in equal parts. | 6.94 µg/mL |
| Sodium Chloride | 7.5 mg/mL |
| Sodium phosphate dibasic heptahydrate | 0.48 mg/mL |
| Potassium phosphate monobasic | 0.06 mg/mL |
| Phenol | 2.5 mg/mL |
| Water | q.s. |

Composition 7:

| Component | Concentration |
| --- | --- |
| Koch's Turberculin (inactivated *Mycobacterium bovis* lysate). | 0.004 ng/mL |
| Inactivated BCG lysate | 50 mg/mL |
| Inactivated *Staphylococcus aureus* lysate, inactivated *Staphylococcus epidermidis* lysate in equal parts. | 6.94 µg/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Candida albincans* lysate, inactivated *Candida parapsilosis* lysate, inactivated *Candida glabrata* in equal parts. | 6.94 µg/mL |
| Inactivated *Streptococcus equinus*, *Streptococcus bovis* and *Streptococcus viridans* lysate in equal parts. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Salmonella typhi*, *Salmonella paratyphi* and *Salmonella enterica* lysate in equal parts. | 6.94 µg/mL |
| Inactivated lysate of antigens of the measles virus ("Schwarz strain"). | 10,000 TDCI50/mL |
| Glycerol | 500 mg/mL |
| Phenol | 2.5 mg/mL |
| Water | q.s. |

Composition 8:

| Component | Concentration |
| --- | --- |
| Koch's Turberculin (inactivated *Mycobacterium bovis* lysate). | 0.004 ng/mL |
| PPD | 0.004 g/mL |
| Inactivated *Staphylococcus aureus* lysate, inactivated *Staphylococcus epidermidis* lysate in equal parts. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Streptokinase derived from inactivated beta-hemolytic *Streptococcus* lysate purification. | 0.444 µg/mL |
| Dornase derived from inactivated beta-hemolytic *Streptococcus* lysate purification. | 0.111 µg/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Helicobacter pylori* lysate. | 6.94 µg/mL |
| Tetanus toxoid | 50 units of Lf/mL |
| Inactivated *Candida albincans* lysate, inactivated *Candida parapsilosis* lysate, inactivated *Candida glabrata* in equal parts. | 6.94 µg/mL |
| Sodium Chloride | 7.5 mg/mL |
| Sodium phosphate dibasic heptahydrate | 0.48 mg/mL |
| Potassium phosphate monobasic | 0.06 mg/mL |
| Phenol | 2.5 mg/mL |
| Water | q.s. |

Composition 9:

| Component | Concentration |
| --- | --- |
| Inactivated *BCG* lysate | 50 mg/mL |
| Inactivated *Mycobacterium tuberculosis* lysate | 0.004 ng/mL |
| Inactivated *Staphylococcus aureus* lysate, inactivated *Staphylococcus epidermidis* lysate in equal parts. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Haemophilus influenza* lysate. | 6.94 µg/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 µg/mL |
| Inactivated *Salmonella typhi*, *Salmonella paratyphi* and *Salmonella enterica* lysate in equal parts. | 6.94 µg/mL |
| Inactivated *Proteus mirabilis*, *Proteus vulgaris*, and *Proteus penerii* lysate in equal parts. | 6.94 µg/mL |
| Inactivated lysate of antigens of the measles virus ("Schwarz strain"). | 10,000 TDCI50/mL |

| Component | Concentration |
|---|---|
| Inactivated *Candida albincans* lysate, inactivated *Candida parapsilosis* lysate, inactivated *Candida glabrata* in equal parts. | 6.94 μg/mL |
| Glycerol | 500 mg/mL |
| Phenol | 2.5 mg/mL |
| Water | q.s. |

Composition 10:

| Component | Concentration |
|---|---|
| Inactivated *Mycobacterium africanum* lysate. | 0.004 ng/mL |
| Koch's Turberculin (inactivated *Mycobacterium bovis* lysate). | 0.004 ng/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 μg/mL |
| Inactivated *Staphylococcus aureus* lysate, inactivated *Staphylococcus epidermidis* lysate in equal parts. | 6.94 μg/mL |
| Inactivated *Epidermophyton floccosum*, *Microsporum cannis*, *Trichophyton mentagrophytes* of the interdigitale variety lysate in equal parts). | 6.94 μg/mL |
| Inactivated *Streptococcus pyogenes* lysate, inactivated *Streptococcus pneumonie* lysate, *Enterococcus faecalis* lysate in equal parts. | 6.94 μg/mL |
| Inactivated *Acinetobacter baumannii* lysate. | 6.94 μg/mL |
| Inactivated *Helicobacter pylori* lysate. | 6.94 μg/mL |
| Inactivated lysate of antigens of the mumps virus (Urabe AM9 strain) | 10,000 TDCI50/mL |
| Inactivated Polio virus lysate | 40 UD of type I antigens; 1.8 UD of type 2 antigens; 32 UD of type 3 antigens |
| Glycerol | 500 mg/mL |
| Phenol | 2.5 mg/mL |
| Water | q.s. |

Composition 11:

| Component | Concentration |
|---|---|
| Inactivated *Mycobacterium leprae* lysate | 0.004 ng/mL |
| Koch's Turberculin (inactivated *Mycobacterium bovis* lysate). | 0.004 ng/mL |
| Inactivated *Staphylococcus aureus* lysate, inactivated *Staphylococcus epidermidis* lysate in equal parts. | 6.94 μg/mL |
| Inactivated *Candida albincans* lysate, inactivated *Candida parapsilosis* lysate, inactivated *Candida glabrata* in equal parts. | 6.94 μg/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 μg/mL |
| Inactivated *Streptococcus equinus*, *Streptococcus bovis*, and *Streptococcus* of the *viridans* group lysate in equal parts. | 6.94 μg/mL |
| Inactivated *Haemophilus influenza* lysate. | 6.94 μg/mL |
| Inactivated *Proteus mirabilis*, *Proteus vulgaris*, and *Proteus penerii* lysate in equal parts. | 6.94 μg/mL |
| Antigens of the rubella virus (Wistar RA 27/3M strain) | 10,000 TDCI50/mL |
| Inactivate antigen of the Varicella zoster virus lysate | 149 231 PFU/mL |
| Glycerol | 500 mg/mL |
| Phenol | 2.5 mg/mL |
| Water | q.s. |

Composition 12:

| Component | Concentration |
|---|---|
| Inactivated *Mycobacterium avium* lysate | 0.004 ng/mL |
| Inactivated *Mycobacterium kansasii* lysate | 0.004 ng/mL |
| Inactivated *Apergillus fumigatus*, *Apergillus flavus*, and *Apergillus terreus* lysate in equal parts. | 6.94 μg/mL |

| Component | Concentration |
|---|---|
| Inactivated *Neisseria gonorrhoeae* lysate. | 6.94 µg/mL |
| Inactivated *Streptococcus equinus*, *Streptococcus bovis*, and *Streptococcus* of the *viridans* group lysate in equal parts. | 6.94 µg/mL |
| Inactivated *Epidermophyton floccosum*, *Microsporum cannis*, *Trichophyton mentagrophytes* of the interdigitale variety lysate in equal parts). | 6.94 µg/mL |
| Inactivated *Chlamydia trachomatis*, *Chlamydia psittaci*, and *Chamydia pneumoniae* lysate in equal parts. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Antigens of the rubella virus (Wistar RA 27/3M strain) | 10,000 TDCI50/mL |
| Inactivated antigen of the Vaccinia (smallpox) virus lysate | 1 to 10 × 10$^9$ PFU/mL |
| Glycerol | 500 mg/mL |
| Phenol | 2.5 mg/mL |
| Water | q.s. |

Composition 13:

| Component | Concentration |
|---|---|
| Inactivated *Mycobacterium tuberculosis* lysate | 0.004 ng/mL |
| Inactivated *Mycobacterium avium* lysate | 0.004 ng/mL |
| Inactivated *Neisseria meningitides* lysate | 6.94 µg/mL |
| Diphtheria toxoid | 67 units of Lf/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 µg/mL |
| Inactivated *Candida albicans* lysate, inactivated *Candida parapsilosis* lysate, inactivated *Candida glabrata* in equal parts. | 6.94 µg/mL |
| Inactivated *Helicobacter pylori* lysate. | 6.94 µg/mL |
| Inactivated *Serratia marcencense Serratia liquefaciens* lysate | 6.94 µg/mL |
| Inactivated antigen of HSV-I and HSV-II lysate | 149 231 PFU/mL |
| Inactivated antigen of the measles virus ("Schwarz strain") lysate | 10,000 TDCI50/mL |
| Glycerol | 500 mg/mL |
| Phenol | 2.5 mg/mL |
| Water | q.s. |

Composition 14:

| Component | Concentration |
|---|---|
| Inactivated *Mycobacterium africanum* lysate | 0.004 ng/mL |
| Inactivated *Mycobacterium tuberculosis* lysate | 0.004 ng/mL |
| Inactivated *Neisseria gonorrhoeae* lysate | 6.94 mg/mL |
| Inactivated *Apergillus fumigatus*, *Apergillus flavus*, and *Apergillus terreus* lysate in equal parts. | 6.94 µg/mL |
| Inactivated *Neisseria meningitides* lysate | 6.94 µg/mL |
| Diphtheria toxoid | 67 units of Lf/mL |
| Inactivated *Epidermophyton floccosum*, *Microsporum cannis*, *Trichophyton mentagrophytes* of the interdigitale variety lysate in equal parts). | 6.94 µg/mL |
| Inactivated *Shigella flexneri* and *Shigella sonnei* lysate in equal parts | 6.94 µg/mL |
| Inactivated surface antigen of the hepatitis B (HBs AG) virus lysate | 200 µg/mL |
| Inactivated antigen of the measles virus ("Schwarz strain") lysate | 10,000 TDCI50/mL |
| Glycerol | 500 mg/mL |
| Phenol | 2.5 mg/mL |
| Water | q.s. |

Composition 15:

| Component | Concentration |
|---|---|
| PPD | 0.004 ng/mL |
| Inactivated BCG lysate | 50 mg/mL |
| Inactivated *Streptococcus equinus*, *Streptococcus bovis*, and *Streptococcus* of the *viridans* group lysate in equal parts. | 6.94 µg/mL |

| Component | Concentration |
| --- | --- |
| Inactivated *Staphylococcus aureus* lysate, inactivated *Staphylococcus epidermidis* lysate in equal parts. | 6.94 μg/mL |
| Tetanus toxoid | 50 units of Lf/mL |
| Diphtheria toxoid | 67 units of Lf/mL |
| Inactivated *Acinetobacter baumannii* lysate. | 6.94 μg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 μg/mL |
| Inactivated *Apergillus fumigatus*, *Apergillus flavus*, and *Apergillus terreus* lysate in equal parts. | 6.94 μg/mL |
| Inactivated lysate of antigens of the mumps virus (Urabe AM9 strain) | 10,000 TDCI50/mL |
| Glycerol | 500 mg/mL |
| Phenol | 2.5 mg/mL |
| Water | q.s. |

Composition 16:

| Component | Concentration |
| --- | --- |
| Koch's Turberculin (inactivated *Mycobacterium bovis* lysate). | 0.004 ng/mL |
| Inactivated *Mycobacterium tuberculosis* lysate | 0.004 ng/mL |
| Inactivated *Salmonella typhi*, *Salmonella paratyphi* and *Salmonella enterica* lysate in equal parts. | 6.94 μg/mL |
| Inactivated *Streptococcus pyogenes* lysate, inactivated *Streptococcus pneumonie* lysate, *Enterococcus faecalis* lysate in equal parts. | 6.94 μg/mL |
| Inactivated *Epidermophyton floccosum*, *Microsporum cannis*, *Trichophyton mentagrophytes* of the interdigitale variety lysate in equal parts). | 6.94 μg/mL |
| *Bordetella pertussis* toxoid | 75 μg/mL |
| Inactivated *Haemophilus influenza* lysate. | 6.94 μg/mL |
| Tetanus toxoid | 50 units of Lf/mL |
| Inactivated Polio virus lysate | 40 UD of type I antigens; 1.8 UD of type 2 antigens; 32 UD of type 3 antigens |
| Inactivated antigen of the Vaccinia (smallpox) virus lysate | 1 to 10 × $10^9$ PFU/mL |
| Glycerol | 500 mg/mL |
| Phenol | 2.5 mg/mL |
| Water | q.s. |

Composition 17:

| Component | Concentration |
| --- | --- |
| Koch's Turberculin (inactivated *Mycobacterium bovis* lysate). | 0.004 ng/mL |
| Inactivated BCG lysate | 50 mg/mL |
| PPD | 0.004 ng/mL |
| Inactivated *Staphylococcus aureus* lysate, inactivated *Staphylococcus epidermidis* lysate in equal parts. | 6.94 μg/mL |
| Inactivated *Streptococcus pyogenes* lysate, inactivated *Streptococcus pneumonie* lysate, *Enterococcus faecalis* lysate in equal parts. | 6.94 μg/mL |
| Inactivated *Klebsiella oxytoca* and *Klebsiella pneumonia* lysate in equal parts | 6.94 μg/mL |
| Inactivated *Epidermophyton floccosum*, *Microsporum cannis*, *Trichophyton mentagrophytes* of the interdigitale variety lysate in equal parts). | 6.94 μg/mL |
| Inactivated *Streptococcus equinus*, *Streptococcus bovis*, and *Streptococcus* of the *viridans* group lysate in equal parts. | 6.94 μg/mL |
| Diphtheria toxoid | 67 units of Lf/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 μg/mL |
| Inactivated *Salmonella typhi*, *Salmonella paratyphi* and *Salmonella enterica* lysate in equal parts. | 6.94 μg/mL |
| *Bordetella pertussis* toxoid | 75 μg/mL |
| Inactivated *Apergillus fumigatus*, *Apergillus flavus*, and *Apergillus terreus* lysate in equal parts. | 6.94 μg/mL |

-continued

| Component | Concentration |
|---|---|
| Inactivated lysate of antigens of the measles virus ("Schwarz strain"). | 10,000 TDCI50/mL |
| Inactivated *Candida albincans* lysate, inactivated *Candida parapsilosis* lysate, inactivated *Candida glabrata* in equal parts. | 6.94 µg/mL |
| Glycerol | 500 mg/mL |
| Phenol | 2.5 mg/mL |
| Water | q.s. |

Composition 18:

| Component | Concentration |
|---|---|
| PPD | 0.004 ng/mL |
| Inactivated *Mycobacterium tuberculosis* lysate | 0.004 ng/mL |
| Koch's Turberculin (inactivated *Mycobacterium bovis* lysate). | 0.004 ng/mL |
| Inactivated *Staphylococcus aureus* lysate, inactivated *Staphylococcus epidermidis* lysate in equal parts. | 6.94 µg/mL |
| Inactivated *Salmonella typhi*, *Salmonella paratyphi* and *Salmonella enterica* lysate in equal parts. | 6.94 µg/mL |
| Inactivated *Streptococcus pyogenes* lysate, inactivated *Streptococcus pneumonie* lysate, *Enterococcus faecalis* lysate in equal parts. | 6.94 µg/mL |
| Streptokinase derived from inactivated beta-hemolytic *Streptococcus* lysate purification. | 0.444 µg/mL |
| Dornase derived from inactivated beta-hemolytic *Streptococcus* lysate purification. | 0.111 µg/mL |
| Inactivated *Klebsiella oxytoca* and *Klebsiella pneumonia* lysate in equal parts | 6.94 µg/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 µg/mL |
| Inactivated *Helicobacter pylori* lysate. | 6.94 µg/mL |
| Tetanus toxoid | 50 units of Lf/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Candida albicans* lysate, inactivated *Candida parapsilosis* lysate, inactivated *Candida glabrata* lysate in equal parts. | 6.94 µg/mL |
| Inactivated *Apergillus fumigatus*, *Apergillus flavus*, and *Apergillus terreus* lysate in equal parts. | 6.94 µg/mL |
| Inactivated YF-17D lysate | 3,000,000 PFU/mL |
| Glycerol | 500 mg/mL |
| Phenol | 2.5 mg/mL |
| Water | q.s. |

Composition 19:

| Component | Concentration |
|---|---|
| Inactivated BCG lysate | 50 mg/mL |
| Inactivated *Mycobacterium tuberculosis* lysate | 0.004 ng/mL |
| Koch's Turberculin (inactivated *Mycobacterium bovis* lysate). | 0.004 ng/mL |
| Inactivated *Staphylococcus aureus* lysate, inactivated *Staphylococcus epidermidis* lysate in equal parts. | 6.94 µg/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Serratia marcencens* e *Serratia liquefaciens* lysate | 6.94 µg/mL |
| Inactivated *Haemophilus influenza* lysate. | 6.94 µg/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 µg/mL |
| Inactivated *Klebsiella oxytoca* and *Klebsiella pneumonia* lysate in equal parts | 6.94 µg/mL |
| Inactivated *Epidermophyton floccosum*, *Microsporum cannis*, *Trichophyton* mentagrophytes of the interdigitale variety lysate in equal parts). | 6.94 µg/mL |
| Inactivated *Proteus mirabilis*, *Proteus vulgaris*, and *Proteus penerii* lysate in equal parts. | 6.94 µg/mL |
| Inactivated *Salmonella typhi*, *Salmonella paratyphi* and *Salmonella enterica* lysate in equal parts. | 6.94 µg/mL |
| Inactivated lysate of antigens of the measles virus ("Schwarz strain"). | 10,000 TDCI50/mL |

-continued

| Component | Concentration |
| --- | --- |
| Inactivated *Candida albicans* lysate, inactivated *Candida parapsilosis* lysate, inactivated *Candida glabrata* lysate in equal parts. | 6.94 µg/mL |
| Inactivated antigen of the Vaccinia (smallpox) virus lysate | 1 to 10 × $10^9$ PFU/mL |
| Glycerol | 500 mg/mL |
| Phenol | 2.5 mg/mL |
| Water | q.s. |

Composition 20:

| Component | Concentration |
| --- | --- |
| Inactivated *Mycobacterium africanum* lysate | 0.004 ng/mL |
| Koch's Turberculin (inactivated *Mycobacterium bovis* lysate). | 0.004 ng/mL |
| Inactivated BCG lysate | 50 mg/mL |
| Inactivated *Apergillus fumigatus*, *Apergillus flavus*, and *Apergillus terreus* lysate in equal parts. | 6.94 µg/mL |
| Inactivated *Staphylococcus aureus* lysate, inactivated *Staphylococcus epidermidis* lysate in equal parts. | 6.94 µg/mL |
| Inactivated *Neisseria meningitides* lysate | 6.94 µg/mL |
| Inactivated *Streptococcus pyogenes* lysate, inactivated *Streptococcus pneumonie* lysate, *Enterococcus faecalis* lysate in equal parts. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Salmonella typhi*, *Salmonella paratyphi* and *Salmonella enterica* lysate in equal parts. | 6.94 µg/mL |
| Inactivated *Acinetobacter baumannii* lysate. | 6.94 µg/mL |
| Inactivated *Helicobacter pylori* lysate. | 6.94 µg/mL |
| Inactivated *Haemophilus influenza* lysate. | 6.94 µg/mL |
| Inactivated lysate of antigens of the mumps virus (Urabe AM9 strain) | 50,000 TDCI50/mL |
| Inactivated Polio virus lysate | 40 UD of type I antigens; 1.8 UD of type 2 antigens; 32 UD of type 3 antigens |
| Inactivated *Candida albicans* lysate, inactivated *Candida parapsilosis* lysate, inactivated *Candida glabrata* lysate in equal parts. | 6.94 µg/mL |
| Glycerol | 500 mg/mL |
| Phenol | 2.5 mg/mL |
| Water | q.s. |

Composition 21:

| Component | Concentration |
| --- | --- |
| Inactivated *Mycobacterium leprae* lysate | 0.004 ng/mL |
| Koch's Turberculin (inactivated *Mycobacterium bovis* lysate). | 0.004 ng/mL |
| Inactivated *Mycobacterium tuberculosis* lysate | 0.004 ng/mL |
| Inactivated *Staphylococcus aureus*lysate, inactivated *Staphylococcus epidermidis* lysate in equal parts. | 6.94 µg/mL |
| Inactivated *Epidermophyton floccosum*, *Microsporum cannis*, *Trichophyton* mentagrophytes of the interdigitale variety lysate in equal parts). | 6.94 µg/mL |
| Diphtheria toxoid | 67 units of Lf/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 µg/mL |
| Tetanus toxoid | 50 units of Lf/mL |
| Inactivated *Neisseria meningitides* lysate | 6.94 µg/mL |
| Inactivated *Haemophilus influenza* lysate. | 6.94 µg/mL |
| Inactivated *Proteus mirabilis*, *Proteus vulgaris*, and *Proteus penerii* lysate in equal parts. | 6.94 µg/mL |
| Inactivated *Serratia marcencens* e *Serratia liquefaciens* lysate | 6.94 µg/mL |
| Antigens of the rubella virus (Wistar RA 27/3M strain) | 10,000 TDCI50/mL |
| Inactivate antigen of the Varicella zoster virus lysate | 149 231 PFU/mL |
| Inactivated *Apergillus fumigatus*, *Apergillus flavus*, and *Apergillus terreus* lysate in equal parts. | 6.94 µg/mL |

| Component | Concentration |
| --- | --- |
| Glycerol | 500 mg/mL |
| Phenol | 2.5 mg/mL |
| Water | q.s. |

Composition 22:

| Component | Concentration |
| --- | --- |
| Inactivated *Mycobacterium avium* lysate | 0.004 ng/mL |
| Inactivated *Mycobacterium kansasii* lysate | 0.004 ng/mL |
| Koch's Turberculin (inactivated *Mycobacterium bovis* lysate). | 0.004 ng/mL |
| Inactivated *Apergillus fumigatus*, *Apergillus flavus*, and *Apergillus terreus* lysate in equal parts. | 6.94 μg/mL |
| Inactivated *Neisseria gonorrhoeae* lysate | 6.94 mg/mL |
| Tetanus toxoid | 50 units of Lf/mL |
| Inactivated *Streptococcus equinus*, *Streptococcus bovis*, and *Streptococcus* of the viridans group lysate in equal parts. | 6.94 μg/mL |
| Inactivated *Candida albicans* lysate, inactivated *Candida parapsilosis* lysate, inactivated *Candida glabrata* lysate in equal parts. | 6.94 μg/mL |
| Inactivated *Salmonella typhi*, *Salmonella paratyphi* and *Salmonella enterica* lysate in equal parts. | 6.94 μg/mL |
| Inactivated *Chlamydia trachomatis*, *Chlamydia psittaci*, and *Chamydia pneumoniae* lysate in equal parts. | 6.94 μg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 μg/mL |
| Inactivated *Klebsiella oxytoca* and *Klebsiella pneumonia* lysate in equal parts | 6.94 μg/mL |
| Antigens of the rubella virus (Wistar RA 27/3M strain) | 10,000 TDCI50/mL |
| Inactivated antigen of the Vaccinia (smallpox) virus lysate | 1 to $10 \times 10^9$ PFU/mL |
| Inactivated YF-17D lysate | 3,000,000 PFU/mL |
| Glycerol | 500 mg/mL |
| Phenol | 2.5 mg/mL |
| Water | q.s. |

Composition 23:

| Component | Concentration |
| --- | --- |
| Inactivated *Mycobacterium tuberculosis* lysate | 0.004 ng/mL |
| Inactivated *Mycobacterium avium* lysate | 0.004 ng/mL |
| Koch's Turberculin (inactivated *Mycobacterium bovis* lysate). | 0.004 ng/mL |
| Inactivated *Neisseria meningitides* lysate | 6.94 μg/mL |
| Diphtheria toxoid | 67 units of Lf/mL |
| Tetanus toxoid | 50 units of Lf/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 μg/mL |
| Inactivated *Candida albicans* lysate, inactivated *Candida parapsilosis* lysate, inactivated *Candida glabrata* lysate in equal parts. | 6.94 μg/mL |
| Inactivated *Epidermophyton floccosum*, *Microsporum cannis*, *Trichophyton* mentagrophytes of the interdigitale variety lysate in equal parts). | 6.94 μg/mL |
| Inactivated *Helicobacter pylori* lysate. | 6.94 μg/mL |
| Inactivated *Serratia marcencens* e *Serratia liquefaciens* lysate | 6.94 μg/mL |
| Inactivated *Salmonella typhi*, *Salmonella paratyphi* and *Salmonella enterica* lysate in equal parts. | 6.94 μg/mL |
| Inactivated antigen of HSV-I and HSV-II lysate | 149 231 PFU/mL |
| Inactivated lysate of antigens of the measles virus ("Schwarz strain"). | 10,000 TDCI50/mL |
| Inactivated *Apergillus fumigatus*, *Apergillus flavus*, and *Apergillus terreus* lysate in equal parts. | 6.94 μg/mL |
| Glycerol | 500 mg/mL |
| Phenol | 2.5 mg/mL |
| Water | q.s. |

Composition 24:

| Component | Concentration |
|---|---|
| Inactivated *Mycobacterium africanum* lysate | 0.004 ng/mL |
| Inactivated *Mycobacterium tuberculosis* lysate | 0.004 ng/mL |
| PPD | 0.004 ng/mL |
| Inactivated *Neisseria gonorrhoeae* lysate | 6.94 mg/mL |
| Inactivated *Candida albicans* lysate, inactivated *Candida parapsilosis* lysate, inactivated *Candida glabrata* lysate in equal parts. | 6.94 µg/mL |
| Inactivated *Salmonella typhi, Salmonella paratyphi* and *Salmonella enterica* lysate in equal parts. | 6.94 µg/mL |
| Inactivated *Neisseria meningitides* lysate | 6.94 µg/mL |
| Diphtheria toxoid | 67 units of Lf/mL |
| Inactivated *Streptococcus equinus, Streptococcus bovis*, and *Streptococcus* of the viridans group lysate in equal parts. | 6.94 µg/mL |
| Tetanus toxoid | 50 units of Lf/mL |
| Inactivated *Shigella flexneri* and *Shigella sonnei* lysate in equal parts | 6.94 µg/mL |
| Inactivated *Proteus mirabilis, Proteus vulgaris*, and *Proteus penerii* lysate in equal parts. | 6.94 µg/mL |
| Inactivated surface antigen of the hepatitis B (HBs AG) virus lysate | 200 µg/mL |
| Inactivated lysate of antigens of the measles virus ("Schwarz strain"). | 10,000 TDCI50/mL |
| Inactivated YF-17D lysate | 3,000,000 PFU/mL |
| Glycerol | 500 mg/mL |
| Phenol | 2.5 mg/mL |
| Water | q.s. |

Composition 25:

| Component | Concentration |
|---|---|
| PPD | 0.004 ng/mL |
| Inactivated BCG lysate | 50 mg/mL |
| Koch's Turberculin (inactivated *Mycobacterium bovis* lysate). | 0.004 ng/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Staphylococcus aureus* lysate, inactivated *Staphylococcus epidermidis* lysate in equal parts. | 6.94 µg/mL |
| Diphtheria toxoid | 67 units of Lf/mL |
| Tetanus toxoid | 50 units of Lf/mL |
| Inactivated *Salmonella typhi, Salmonella paratyphi* and *Salmonella enterica* lysate in equal parts. | 6.94 µg/mL |
| Inactivated *Epidermophyton floccosum, Microsporum cannis, Trichophyton mentagrophytes* of the interdigitale variety lysate in equal parts. | 6.94 µg/mL |
| Inactivated *Acinetobacter baumannii* lysate. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Candida albicans* lysate, inactivated *Candida parapsilosis* lysate, inactivated *Candida glabrata* lysate in equal parts. | 6.94 µg/mL |
| Inactivated *Apergillus fumigatus, Apergillus flavus*, and *Apergillus terreus* lysate in equal parts. | 6.94 µg/mL |
| Inactivated lysate of antigens of the mumps virus (Urabe AM19 strain) | 50,000 TDCI50/mL |
| Inactivated antigen of the Vaccinia (smallpox) virus lysate | 1 to 10 × $10^9$ PFU/mL |
| Glycerol | 500 mg/mL |
| Phenol | 2.5 mg/mL |
| Water | q.s. |

Composition 26:

| Component | Concentration |
|---|---|
| Koch's Turberculin (inactivated *Mycobacterium bovis* lysate). | 0.004 ng/mL |
| Inactivated *Mycobacterium tuberculosis* lysate | 0.004 ng/mL |
| Inactivated BCG lysate | 50 mg/mL |
| Inactivated *Apergillus fumigatus, Apergillus flavus*, and *Apergillus terreus* lysate in equal parts. | 6.94 µg/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Chlamydia trachomatis, Chlamydia psittaci*, and *Chamydia pneumoniae* lysate in equal parts. | 6.94 µg/mL |
| *Bordetella pertussis* toxoid | 75 µg/mL |
| Inactivated *Haemophilus influenza* lysate. | 6.94 µg/mL |

| Component | Concentration |
| --- | --- |
| Inactivated *Neisseria gonorrhoeae* lysate | 6.94 mg/mL |
| Tetanus toxoid | 50 units of Lf/mL |
| Inactivated *Candida albicans* lysate, inactivated *Candida parapsilosis* lysate, inactivated *Candida glabrata* lysate in equal parts. | 6.94 μg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 μg/mL |
| Inactivated Polio virus lysate | 40 UD of type I antigens; 1.8 UD of type 2 antigens; 32 UD of type 3 antigens |
| Inactivated antigen of the Vaccinia (smallpox) virus lysate | 1 to 10 × $10^9$ PFU/mL |
| Inactivated YF-17D lysate | 3,000,000 PFU/mL |

Composition 27:

| Component | Concentration |
| --- | --- |
| Inactivated YF-17D lysate | 3,000,000 PFU/mL |
| Koch's Turberculin (inactivated *Mycobacterium bovis* lysate). | 0.004 ng/mL |
| Inactivated BCG lysate | 50 mg/mL |
| PPD | 0.004 ng/mL |
| Inactivated *Mycobacterium tuberculosis* lysate | 0.004 ng/mL |
| Inactivated *Staphylococcus aureus* lysate, inactivated *Staphylococcus epidermidis* lysate in equal parts. | 6.94 μg/mL |
| Inactivated *Streptococcus pyogenes* lysate, inactivated *Streptococcus pneumonie* lysate, *Enterococcus faecalis* lysate in equal parts. | 6.94 μg/mL |
| Inactivated *Klebsiella oxytoca* and *Klebsiella pneumonia* lysate in equal parts | 6.94 μg/mL |
| Inactivated *Neisseria meningitides* lysate | 6.94 μg/mL |
| Inactivated *Candida albicans* lysate, inactivated *Candida parapsilosis* lysate, inactivated *Candida glabrata* lysate in equal parts. | 6.94 μg/mL |
| Inactivated *Streptococcus equinus*, *Streptococcus bovis*, and *Streptococcus* of the viridans group lysate in equal parts. | 6.94 μg/mL |
| Inactivated *Epidermophyton floccosum*, *Microsporum cannis*, *Trichophyton* mentagrophytes of the interdigitale variety lysate in equal parts). | 6.94 μg/mL |
| Inactivated *Shigella flexneri* and *Shigella sonnei* lysate in equal parts | 6.94 μg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 μg/mL |
| Inactivated *Salmonella typhi*, *Salmonella paratyphi* and *Salmonella enterica* lysate in equal parts. | 6.94 μg/mL |
| *Bordetella pertussis* toxoid | 75 μg/mL |
| Inactivated antigen of the Vaccinia (smallpox) virus lysate | 1 to 10 × $10^9$ PFU/mL |
| Inactivated *Apergillus fumigatus*, *Apergillus flavus*, and *Apergillus terreus* lysate in equal parts. | 6.94 μg/mL |
| Inactivated lysate of antigens of the measles virus ("Schwarz strain"). | 10,000 TDCI50/mL |
| Glycerol | 500 mg/mL |
| Phenol | 2.5 mg/mL |
| Water | q.s. |

Composition 28:

| Component | Concentration |
| --- | --- |
| Inactivated *Mycobacterium tuberculosis* lysate | 0.004 ng/mL |
| Koch's Turberculin (inactivated *Mycobacterium bovis* lysate). | 0.004 ng/mL |
| Inactivated *Mycobacterium avium* lysate | 0.004 ng/mL |
| Inactivated *Staphylococcus aureus* lysate, inactivated *Staphylococcus epidermidis* lysate in equal parts. | 6.94 μg/mL |
| Inactivated *Streptococcus pyogenes* lysate, inactivated *Streptococcus pneumonie* lysate, *Enterococcus faecalis* lysate in equal parts. | 6.94 μg/mL |
| Inactivated *Epidermophyton floccosum*, *Microsporum cannis*, *Trichophyton mentagrophytes* of the interdigitale variety lysate in equal parts). | 6.94 μg/mL |
| Inactivated *Neisseria meningitides* lysate | 6.94 μg/mL |

| Component | Concentration |
| --- | --- |
| Streptokinase derived from inactivated beta-hemolytic *Streptococcus* lysate purification. | 0.444 μg/mL |
| Dornase derived from inactivated beta-hemolytic *Streptococcus* lysate purification. | 0.111 μg/mL |
| Inactivated *Salmonella typhi*, *Salmonella paratyphi* and *Salmonella enterica* lysate in equal parts. | 6.94 μg/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 μg/mL |
| Inactivated *Enterobacter aerogenes*, *Enterobacter cloacae*, and *Enterobacter agglomerans* group lysate. | 6.94 μg/mL |
| Inactivated *Helicobacter pylori* lysate. | 6.94 μg/mL |
| Tetanus toxoid | 50 units of Lf/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 μg/mL |
| Inactivated antigen of the Vaccinia (smallpox) virus lysate | 1 to $10 \times 10^9$ PFU/mL |
| Inactivated *Candida albicans* lysate, inactivated *Candida parapsilosis* lysate, inactivated *Candida glabrata* lysate in equal parts. | 6.94 μg/mL |
| Inactivated *Apergillus fumigatus*, *Apergillus flavus*, and *Apergillus terreus* lysate in equal parts. | 6.94 μg/mL |
| Inactivated YF-17D lysate | 3,000,000 PFU/mL |
| Glycerol | 500 mg/mL |
| Phenol | 2.5 mg/mL |
| Water | q.s. |

Composition 29:

| Component | Concentration |
| --- | --- |
| Inactivated lysate of antigens of the mumps virus (Urabe AM9 strain) | 50,000 TDCI50/mL |
| Inactivated BCG lysate | 50 mg/mL |
| Inactivated *Mycobacterium tuberculosis* lysate | 0.004 ng/mL |
| Koch's Turberculin (inactivated *Mycobacterium bovis* lysate). | 0.004 ng/mL |
| Inactivated *Mycobacterium leprae* lysate | 0.004 ng/mL |
| Inactivated *Staphylococcus aureus* lysate, inactivated *Staphylococcus epidermidis* lysate in equal parts. | 6.94 μg/mL |
| Inactivated *Streptococcus equinus*, *Streptococcus bovis*, and *Streptococcus* of the viridans group lysate in equal parts. | 6.94 μg/mL |
| Inactivated *Serratia marcencens* and *Serratia liquefaciens* lysate | 6.94 μg/mL |
| Inactivated *Epidermophyton floccosum*, *Microsporum cannis*, *Trichophyton mentagrophytes* of the interdigitale variety lysate in equal parts). | 6.94 μg/mL |
| Inactivated *Haemophilus influenza* lysate. | 6.94 μg/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 μg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 μg/mL |
| Tetanus toxoid | 50 units of Lf/mL |
| Inactivated *Proteus mirabilis*, *Proteus vulgaris*, and *Proteus penerii* lysate in equal parts. | 6.94 μg/mL |
| Inactivated *Salmonella typhi*, *Salmonella paratyphi* and *Salmonella enterica* lysate in equal parts. | 6.94 μg/mL |
| Inactivated *Apergillus fumigatus*, *Apergillus flavus*, and *Apergillus terreus* lysate in equal parts. | 6.94 μg/mL |
| Inactivated lysate of antigens of the measles virus ("Schwarz strain"). | 10,000 TDCI50/mL |
| Inactivated *Candida albicans* lysate, inactivated *Candida parapsilosis* lysate, inactivated *Candida glabrata* lysate in equal parts. | 6.94 μg/mL |
| Inactivated antigen of the Vaccinia (smallpox) virus lysate | 1 to $10 \times 10^9$ PFU/mL |
| Glycerol | 500 mg/mL |
| Phenol | 2.5 mg/mL |
| Water | q.s. |

Composition 30:

| Component | Concentration |
| --- | --- |
| Inactivated *Apergillus fumigatus*, *Apergillus flavus*, and *Apergillus terreus* lysate in equal parts. | 6.94 µg/mL |
| Inactivated *Mycobacterium africanum* lysate | 0.004 ng/mL |
| Koch's Turberculin (inactivated *Mycobacterium bovis* lysate). | 0.004 ng/mL |
| Inactivated BCG lysate | 50 mg/mL |
| Inactivated *Mycobacterium tuberculosis* lysate | 0.004 ng/mL |
| Inactivated *Streptococcus equinus*, *Streptococcus bovis*, and *Streptococcus* of the viridans group lysate in equal parts. | 6.94 µg/mL |
| Inactivated *Staphylococcus aureus* lysate, inactivated *Staphylococcus epidermidis* lysate in equal parts. | 6.94 µg/mL |
| Inactivated *Neisseria meningitides* lysate | 6.94 µg/mL |
| Diphtheria toxoid | 67 units of Lf/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Epidermophyton floccosum*, *Microsporum cannis*, *Trichophyton mentagrophytes* of the interdigitale variety lysate in equal parts). | 6.94 µg/mL |
| Inactivated *Salmonella typhi*, *Salmonella paratyphi* and *Salmonella enterica* lysate in equal parts. | 6.94 µg/mL |
| Inactivated *Acinetobacter baumannii* lysate. | 6.94 µg/mL |
| Inactivated *Helicobacter pylori* lysate. | 6.94 µg/mL |
| Inactivated *Haemophilus influenza* lysate. | 6.94 µg/mL |
| Inactivated YF-17D lysate | 3,000,000 PFU/mL |
| Inactivated lysate of antigens of the mumps virus (Urabe AM9 strain) | 50,000 TDCI50/mL |
| Inactivated Polio virus lysate | 40 UD of type I antigens; 1.8 UD of type 2 antigens; 32 UD of type 3 antigens |
| Inactivated *Candida albicans* lysate, inactivated *Candida parapsilosis* lysate, inactivated *Candida glabrata* lysate in equal parts. | 6.94 µg/mL |
| Glycerol | 500 mg/mL |
| Phenol | 2.5 mg/mL |
| Water | q.s. |

Composition 31:

| Component | Concentration |
| --- | --- |
| Inactivated *Salmonella typhi*, *Salmonella paratyphi* and *Salmonella enterica* lysate in equal parts. | 6.94 µg/mL |
| Inactivated *Mycobacterium leprae* lysate | 0.004 ng/mL |
| Koch's Turberculin (inactivated *Mycobacterium bovis* lysate). | 0.004 ng/mL |
| Inactivated *Mycobacterium tuberculosis* lysate | 0.004 ng/mL |
| PPD | 0.004 ng/mL |
| Inactivated *Staphylococcus aureus* lysate, inactivated *Staphylococcus epidermidis* lysate in equal parts. | 6.94 µg/mL |
| Inactivated *Streptococcus pyogenes* lysate, inactivated *Streptococcus pneumonie* lysate, *Enterococcus faecalis* lysate in equal parts. | 6.94 µg/mL |
| Diphtheria toxoid | 67 units of Lf/mL |
| Inactivated *Neisseria gonorrhoeae* lysate | 6.94 mg/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 µg/mL |
| Inactivated *Epidermophyton floccosum*, *Microsporum cannis*, *Trichophyton mentagrophytes* of the interdigitale variety lysate in equal parts). | 6.94 µg/mL |
| Inactivated *Neisseria meningitides* lysate | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Haemophilus influenza* lysate. | 6.94 µg/mL |
| Inactivated *Proteus mirabilis*, *Proteus vulgaris*, and *Proteus penerii* lysate in equal parts. | 6.94 µg/mL |
| Inactivated *Serratia marcencens* e *Serratia liquefaciens* lysate | 6.94 µg/mL |
| Inactivated *Candida albicans* lysate, inactivated *Candida parapsilosis* lysate, inactivated *Candida glabrata* lysate in equal parts. | 6.94 µg/mL |
| Antigens of the rubella virus (Wistar RA 27/3M strain) | 10,000 TDCI50/mL |
| Inactivate antigen of the Varicella zoster virus lysate | 149231 PFU/mL |

| Component | Concentration |
| --- | --- |
| Inactivated *Apergillus fumigatus*, *Apergillus flavus*, and *Apergillus terreus* lysate in equal parts. | 6.94 µg/mL |
| Glycerol | 500 mg/mL |
| Phenol | 2.5 mg/mL |
| Water | q.s. |

Composition 32:

| Component | Concentration |
| --- | --- |
| Inactivated *Candida albicans* lysate, inactivated *Candida parapsilosis* lysate, inactivated *Candida glabrata* lysate in equal parts. | 6.94 µg/mL |
| Inactivated *Mycobacterium avium* lysate | 0.004 ng/mL |
| Inactivated *Mycobacterium kansasii* lysate | 0.004 ng/mL |
| Koch's Turberculin (inactivated *Mycobacterium bovis* lysate). | 0.004 ng/mL |
| Inactivated BCG lysate | 50 mg/mL |
| Inactivated *Apergillus fumigatus*, *Apergillus flavus*, and *Apergillus terreus* lysate in equal parts. | 6.94 µg/mL |
| Inactivated *Neisseria gonorrhoeae* lysate | 6.94 mg/mL |
| Tetanus toxoid | 50 units of Lf/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Streptococcus equinus*, *Streptococcus bovis*, and *Streptococcus* of the viridans group lysate in equal parts. | 6.94 µg/mL |
| Inactivated *Epidermophyton floccosum*, *Microsporum cannis*, *Trichophyton mentagrophytes* of the interdigitale variety lysate in equal parts). | 6.94 µg/mL |
| Inactivated *Salmonella typhi*, *Salmonella paratyphi* and *Salmonella enterica* lysate in equal parts. | 6.94 µg/mL |
| Inactivated *Helicobacter pylori* lysate. | 6.94 µg/mL |
| Inactivated *Chlamydia trachomatis*, *Chlamydia psittaci*, and *Chamydia pneumoniae* lysate in equal parts. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Klebsiella oxytoca* and *Klebsiella pneumonia* lysate in equal parts | 6.94 µg/mL |
| Antigens of the rubella virus (Wistar RA 27/3M strain) | 10,000 TDCI50/mL |
| Inactivated antigen of the Vaccinia (smallpox) virus lysate | 1 to 10 × 10$^9$ PFU/mL |
| Inactivated YF-17D lysate | 3,000,000 PFU/mL |
| Glycerol | 500 mg/mL |
| Phenol | 2.5 mg/mL |
| Water | q.s. |

Composition 33:

| Component | Concentration |
| --- | --- |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Mycobacterium leprae* lysate | 0.004 ng/mL |
| Inactivated *Mycobacterium avium* lysate | 0.004 ng/mL |
| Koch's Turberculin (inactivated *Mycobacterium bovis* lysate). | 0.004 ng/mL |
| Inactivated *Mycobacterium tuberculosis* lysate | 0.004 ng/mL |
| Inactivated *Neisseria meningitides* lysate | 6.94 µg/mL |
| Diphtheria toxoid | 67 units of Lf/mL |
| Tetanus toxoid | 50 units of Lf/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Apergillus fumigatus*, *Apergillus flavus*, and *Apergillus terreus* lysate in equal parts. | 6.94 µg/mL |
| Inactivated *Candida albicans* lysate, inactivated *Candida parapsilosis* lysate, inactivated *Candida glabrata* lysate in equal parts. | 6.94 µg/mL |
| Inactivated *Shigella flexneri* and *Shigella sonnei* lysate in equal parts | 6.94 µg/mL |
| Inactivated *Helicobacter pylori* lysate. | 6.94 µg/mL |
| Inactivated *Serratia marcencens* e *Serratia liquefaciens* lysate | 6.94 µg/mL |
| Inactivated *Salmonella typhi*, *Salmonella paratyphi* and *Salmonella enterica* lysate in equal parts. | 6.94 µg/mL |

-continued

| Component | Concentration |
|---|---|
| Inactivated antigen of the Vaccinia (smallpox) virus lysate | 1 to 10 × 10⁹ PFU/mL |
| Inactivated antigen of HSV-I and HSV-II lysate | 149231 PFU/mL |
| Inactivated lysate of antigens of the measles virus ("Schwarz strain"). | 10,000 TDCI50/mL |
| Glycerol | 500 mg/mL |
| Phenol | 2.5 mg/mL |
| Water | q.s. |

Composition 34:

| Component | Concentration |
|---|---|
| Inactivated *Candida albicans* lysate, inactivated *Candida parapsilosis* lysate, inactivated *Candida glabrata* lysate in equal parts. | 6.94 µg/mL |
| Inactivated *Mycobacterium africanum* lysate | 0.004 ng/mL |
| Inactivated *Mycobacterium tuberculosis* lysate | 0.004 ng/mL |
| PPD | 0.004 ng/mL |
| Inactivated BCG lysate | 50 mg/mL |
| Tetanus toxoid | 50 units of Lf/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Salmonella typhi*, *Salmonella paratyphi* and *Salmonella enterica* lysate in equal parts. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Neisseria meningitides* lysate | 6.94 µg/mL |
| Diphtheria toxoid | 67 units of Lf/mL |
| Inactivated *Streptococcus equinus*, *Streptococcus bovis*, and *Streptococcus* of the viridans group lysate in equal parts. | 6.94 µg/mL |
| Inactivated *Apergillus fumigatus*, *Apergillus flavus*, and *Apergillus terreus* lysate in equal parts. | 6.94 µg/mL |
| Inactivated *Shigella flexneri* and *Shigella sonnei* lysate in equal parts | 6.94 µg/mL |
| Inactivated *Proteus mirabilis*, *Proteus vulgaris*, and *Proteus penerii* lysate in equal parts. | 6.94 µg/mL |
| Inactivated surface antigen of the hepatitis B (HBs AG) virus lysate | 200 µg/mL |
| Inactivated lysate of antigens of the measles virus ("Schwarz strain"). | 110,000 TDCI50/mL |
| Inactivated YF-17D lysate | 3,000,000 PFU/mL |
| Glycerol | 500 mg/mL |
| Phenol | 2.5 mg/mL |
| Water | q.s. |

Composition 35:

| Component | Concentration |
|---|---|
| Inactivated *Candida albicans* lysate, inactivated *Candida parapsilosis* lysate, inactivated *Candida glabrata* lysate in equal parts. | 6.94 µg/mL |
| PPD | 0.004 ng/mL |
| Inactivated BCG lysate | 50 mg/mL |
| Koch's Turberculin (inactivated *Mycobacterium bovis* lysate). | 0.004 ng/mL |
| Inactivated *Mycobacterium tuberculosis* lysate | 0.004 ng/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Staphylococcus aureus* lysate, inactivated *Staphylococcus epidermidis* lysate in equal parts. | 6.94 µg/mL |
| Inactivated *Epidermophyton floccosum*, *Microsporum cannis*, *Trichophyton mentagrophytes* of the interdigitale variety lysate in equal parts). | 6.94 µg/mL |
| Inactivated *Neisseria meningitides* lysate | 6.94 µg/mL |
| Tetanus toxoid | 50 units of Lf/mL |
| Diphtheria toxoid | 67 units of Lf/mL |
| Inactivated *Streptococcus equinus*, *Streptococcus bovis*, and *Streptococcus* of the viridans group lysate in equal parts. | 6.94 µg/mL |
| Inactivated *Serratia marcencens* e *Serratia liquefaciens* lysate | 6.94 µg/mL |
| Inactivated *Acinetobacter baumannii* lysate. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |

-continued

| Component | Concentration |
|---|---|
| Inactivated *Salmonella typhi*, *Salmonella paratyphi* and *Salmonella enterica* lysate in equal parts. | 6.94 µg/mL |
| Inactivated YF-17D lysate | 3,000,000 PFU/mL |
| Inactivated *Apergillus fumigatus*, *Apergillus flavus*, and *Apergillus terreus* lysate in equal parts. | 6.94 µg/mL |
| Inactivated lysate of antigens of the mumps virus (Urabe AM9 strain) | 50,000 TDCI50/mL |
| Inactivated antigen of the Vaccinia (smallpox) virus lysate | 1 to $10 \times 10^9$ PFU/mL |
| Glycerol | 500 mg/mL |
| Phenol | 2.5 mg/mL |
| Water | q.s. |

Composition 36:

| Component | Concentration |
|---|---|
| Inactivated *Apergillus fumigatus*, *Apergillus flavus*, and *Apergillus terreus* lysate in equal parts. | 6.94 µg/mL |
| Koch's Turberculin (inactivated *Mycobacterium bovis* lysate). | 0.004 ng/mL |
| Inactivated *Mycobacterium tuberculosis* lysate | 0.004 ng/mL |
| Inactivated BCG lysate | 50 mg/mL |
| PPD (purified protein derivative) | 0.004 ng/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Chlamydia trachomatis*, *Chlamydia psittaci*, and *Chamydia pneumoniae* lysate in equal parts. | 6.94 µg/mL |
| Inactivated *Epidermophyton floccosum*, *Microsporum cannis*, *Trichophyton mentagrophytes* of the interdigitale variety lysate in equal parts). | 6.94 µg/mL |
| *Bordetella pertussis* toxoid | 75 µg/mL |
| Inactivated *Haemophilus influenza* lysate. | 6.94 µg/mL |
| Streptokinase derived from inactivated beta-hemolytic *Streptococcus* lysate purification. | 0.444 µg/mL |
| Dornase derived from inactivated beta-hemolytic *Streptococcus* lysate purification. | 0.111 µg/mL |
| Inactivated *Salmonella typhi*, *Salmonella paratyphi* and *Salmonella enterica* lysate in equal parts. | 6.94 µg/mL |
| Tetanus toxoid | 50 units of Lf/mL |
| Inactivated surface antigen of the hepatitis B (HBs AG) virus lysate | 200 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Candida albicans* lysate, inactivated *Candida parapsilosis* lysate, inactivated *Candida glabrata* lysate in equal parts. | 6.94 µg/mL |
| Inactivated Polio virus lysate | 40 UD of type I antigens; 1.8 UD of type 2 antigens; 32 UD of type 3 antigens |
| Inactivated antigen of the Vaccinia (smallpox) virus lysate | 1 to $10 \times 10^9$ PFU/mL |
| Inactivated YF-17D lysate | 3,000,000 PFU/mL |
| Glycerol | 500 mg/mL |
| Phenol | 2.5 mg/mL |
| Water | q.s. |

When there are parasitic diseases, associated or to be fought, the formulations will preferentially contain antigenic agens of parasitic origin. In this case, according to the concept described in the present invention, the formulations should comprise antigenic agents originating from the most prevalent parasites for which the individuals have more memory cells, according to the geographic distribution and the local and regional human development (developed or non-developed countries). Such parameters are determinant for the occurrence of these parasites and the existence of corresponding memory cells in the immune system of the population of a given region.

Composition 37: Association of Composition 2 with:

| Component | Concentration |
|---|---|
| Inactivated *Toxoplasma gondii* lysate | 400 µg/mL |

Composition 38: Association of Composition 3 with:

| Component | Concentration |
|---|---|
| Inactivated *Giardi lamblia* lysate | 400 µg/mL |

Composition 39: Association of Composition 4 with:

| Component | Concentration |
|---|---|
| Inactivated *Entamoeba histolytica* lysate | 400 µg/mL |

Composition 40: Association of Composition 5 with:

| Component | Concentration |
|---|---|
| Inactivated *Ascaris lumbricoides* lysate | 400 µg/mL |

Composition 41: Association of Composition 6 with:

| Component | Concentration |
|---|---|
| Inactivated *Enterobius vermicularis* lysate | 400 µg/mL |

Composition 42: Association of Composition 7 with:

| Component | Concentration |
|---|---|
| Inactivated *Entamoeba histolytica* lysate | 400 µg/mL |
| Inactivated *Ascaris lumbricoides* lysate | 400 µg/mL |

Composition 43: Association of Composition 8 with:

| Component | Concentration |
|---|---|
| Inactivated *Giardi lamblia* lysate | 400 µg/mL |
| Inactivated *Enterobius vermicularis* lysate | 400 µg/mL |

Composition 44: Association of Composition 9 with:

| Component | Concentration |
|---|---|
| Inactivated *Strongyloides stercoralis* lysate | 400 µg/mL |
| Inactivated *Entamoeba histolytica* lysate | 400 µg/mL |

Composition 45: Association of Composition 10 with:

| Component | Concentration |
|---|---|
| Inactivated *Giardia lamblia* lysate | 400 µg/mL |
| Inactivated *Ascaris lumbricoides* lysate | 400 µg/mL |

Composition 46: Association of Composition 11 with:

| Component | Concentration |
|---|---|
| Inactivated *Toxoplasma gondii* lysate | 400 µg/mL |
| Inactivated *Entamoeba histolytica* lysate | 400 µg/mL |

Composition 47: Association of Composition 12 with

| Component | Concentration |
|---|---|
| Inactivated *Strongyloides stercoralis* lysate | 400 µg/mL |
| Inactivated *Cryptosporidium* spp. lysate | 400 µg/mL |

Composition 48: Association of Composition 13 with:

| Component | Concentration |
|---|---|
| Inactivated *Ascaris lumbricoides* lysate | 400 µg/mL |
| Inactivated *Toxoplasma gondii* lysate | 400 µg/mL |

Composition 49: Association of Composition 14 with:

| Component | Concentration |
|---|---|
| Inactivated *Entamoeba histolytica* lysate | 400 µg/mL |
| Inactivated *Giardia lamblia* lysate | 400 µg/mL |

Composition 50: Association of Composition 15 with:

| Component | Concentration |
|---|---|
| Inactivated *Strongyloides stercoralis* lysate | 400 µg/mL |
| Inactivated *Enterobius vermicularis* lysate | 400 µg/mL |

Composition 51: Association of Composition 16 with:

| Component | Concentration |
|---|---|
| Inactivated *Trichomonas vaginalis* lysate | 400 µg/mL |
| Inactivated *Ascaris lumbricoides* lysate | 400 µg/mL |

Composition 52: Association of Composition 17 with:

| Component | Concentration |
|---|---|
| Inactivated *Entamoeba histolytica* lysate | 400 µg/mL |
| Inactivated *Ascaris lumbricoides* lysate | 400 µg/mL |
| Inactivated *Enterobius vermicularis* lysate | 400 µg/mL |

Composition 53: Association of Composition 18 with:

| Component | Concentration |
|---|---|
| Inactivated *Giardia lamblia* lysate | 400 µg/mL |
| Inactivated *Enterobius vermicularis* lysate | 400 µg/mL |
| Inactivated *Toxoplasma gondii* lysate | 400 µg/mL |

Composition 54: Association of Composition 19 with:

| Component | Concentration |
|---|---|
| Inactivated *Strongyloides stercoralis* lysate | 400 µg/mL |
| Inactivated *Entamoeba histolytica* lysate | 400 µg/mL |
| Inactivated *Giardia lamblia* lysate | 400 µg/mL |

Composition 55: Association of Composition 20 with:

| Component | Concentration |
|---|---|
| Inactivated *Giardia lamblia* lysate | 400 µg/mL |
| Inactivated *Ascaris lumbricoides* lysate | 400 µg/mL |
| Inactivated *Strongyloides stercoralis* lysate | 400 µg/mL |

Composition 56: Association of Composition 21 with:

| Component | Concentration |
|---|---|
| Inactivated *Toxoplasma gondii* lysate | 400 µg/mL |
| Inactivated *Entamoeba histolytica* lysate | 400 µg/mL |
| Inactivated *Giardia lamblia* lysate | 400 µg/mL |

Composition 57: Association of Composition 22 with:

| Component | Concentration |
|---|---|
| Inactivated *Strongyloides stercoralis* lysate | 400 µg/mL |
| Inactivated *Cryptosporidium* spp. lysate | 400 µg/mL |
| Inactivated *Entamoeba histolytica* lysate | 400 µg/mL |

Composition 58: Association of Composition 23 with:

| Component | Concentration |
|---|---|
| Inactivated *Ascaris lumbricoides* lysate | 400 µg/mL |
| Inactivated *Toxoplasma gondii* lysate | 400 µg/mL |
| Inactivated *Enterobius vermicularis* lysate | 400 µg/mL |

Composition 59: Association of Composition 24 with:

| Component | Concentration |
|---|---|
| Inactivated *Entamoeba histolytica* lysate | 400 µg/mL |
| Inactivated *Giardia lamblia* lysate | 400 µg/mL |
| Inactivated *Ascaris lumbricoides* lysate | 400 µg/mL |

Composition 60: Association of Composition 25 with:

| Component | Concentration |
|---|---|
| Inactivated *Strongyloides stercoralis* lysate | 400 µg/mL |
| Inactivated *Enterobius vermicularis* lysate | 400 µg/mL |
| Inactivated *Entamoeba histolytica* lysate | 400 µg/mL |

Composition 61: Association of Composition 26 with:

| Component | Concentration |
|---|---|
| Inactivated *Trichomonas vaginalis* lysate | 400 µg/mL |
| Inactivated *Ascaris lumbricoides* lysate | 400 µg/mL |
| Inactivated *Giardia lamblia* lysate | 400 µg/mL |

Composition 62: Association of Composition 27 with:

| Component | Concentration |
|---|---|
| Inactivated *Entamoeba histolytica* lysate | 400 µg/mL |
| Inactivated *Ascaris lumbricoides* lysate | 400 µg/mL |
| Inactivated *Enterobius vermicularis* lysate | 400 µg/mL |
| Inactivated *Cryptosporidium* spp. lysate | 400 µg/mL |

Composition 63: Association of Composition 28 with:

| Component | Concentration |
|---|---|
| Inactivated *Giardia lamblia* lysate | 400 µg/mL |
| Inactivated *Enterobius vermicularis* lysate | 400 µg/mL |
| Inactivated *Toxoplasma gondii* lysate | 400 µg/mL |
| Inactivated *Ascaris lumbricoides* lysate | 400 µg/mL |

Composition 64: Association of Composition 29 with:

| Component | Concentration |
|---|---|
| Inactivated *Strongyloides stercoralis* lysate | 400 µg/mL |
| Inactivated *Entamoeba histolytica* lysate | 400 µg/mL |
| Inactivated *Giardia lamblia* lysate | 400 µg/mL |
| Inactivated *Enterobius vermicularis* lysate | 400 µg/mL |

Composition 65: Association of Composition 30 with:

| Component | Concentration |
|---|---|
| Inactivated *Giardia lamblia* lysate | 400 µg/mL |
| Inactivated *Ascaris lumbricoides* lysate | 400 µg/mL |
| Inactivated *Strongyloides stercoralis* lysate | 400 µg/mL |
| Inactivated *Entamoeba histolytica* lysate | 400 µg/mL |

Composition 66: Association of Composition 31 with:

| Component | Concentration |
|---|---|
| Inactivated *Toxoplasma gondii* lysate | 400 µg/mL |
| Inactivated *Entamoeba histolytica* lysate | 400 µg/mL |
| Inactivated *Giardia lamblia* lysate | 400 µg/mL |
| Inactivated *Enterobius vermicularis* lysate | 400 µg/mL |

Composition 67: Association of Composition 32 with:

| Component | Concentration |
|---|---|
| Inactivated *Strongyloides stercoralis* lysate | 400 µg/mL |
| Inactivated *Cryptosporidium* spp. lysate | 400 µg/mL |
| Inactivated *Entamoeba histolytica* lysate | 400 µg/mL |
| Inactivated *Ascaris lumbricoides* lysate | 400 µg/mL |

Composition 68: Association of Composition 33 with:

| Component | Concentration |
|---|---|
| Inactivated *Ascaris lumbricoides* lysate | 400 µg/mL |
| Inactivated *Toxoplasma gondii* lysate | 400 µg/mL |
| Inactivated *Enterobius vermicularis* lysate | 400 µg/mL |
| Inactivated *Cryptosporidium* spp. lysate | 400 µg/mL |

Composition 69: Association of Composition 34 with:

| Component | Concentration |
|---|---|
| Inactivated *Entamoeba histolytica* lysate | 400 µg/mL |
| Inactivated *Giardia lamblia* lysate | 400 µg/mL |
| Inactivated *Ascaris lumbricoides* lysate | 400 µg/mL |
| Inactivated *Trichomonas vaginalis* lysate | 400 µg/mL |

Composition 70: Association of Composition 35 with:

| Component | Concentration |
|---|---|
| Inactivated *Strongyloides stercoralis* lysate | 400 µg/mL |
| Inactivated *Enterobius vermicularis* lysate | 400 µg/mL |
| Inactivated *Entamoeba histolytica* lysate | 400 µg/mL |
| Inactivated *Cryptosporidium* spp. lysate | 400 µg/mL |

Composition 71: Association of Composition 36 with:

| Component | Concentration |
|---|---|
| Inactivated *Trichomonas vaginalis* lysate | 400 µg/mL |
| Inactivated *Ascaris lumbricoides* lysate | 400 µg/mL |
| Inactivated *Giardia lamblia* lysate | 400 µg/mL |

Example 2: Treating Septicemia

Patient Data
Patient J-P, 58 years old, male.
Principal Diagnosis
Septicemia.
Secondary Diagnoses
Polytrauma with:
  Complex infected wounds with major loss of tissue of approximately 40 cm.
  extensive infected tissue necrosis with indication for amputation of the left lower limb.
infected grade IIIB open fracture with osteomyelitis of the left femur with lateral exposure.
  open wounds, infected cut-contusion without possibility of suture on the left arm, back of the left foot and on the right lateral malleolus region.
Identification and Summary of the Clinical History
  On Jan. 12, 2011 the patient was admitted to the Intensive Care Unit of the Octavian Constantine Hospital das Clinicas of Teresopolis, victim of a landslide with a grade III b open fracture of the left femur with the exposure of the lateral cut and medial cut-contusion with an extension of 40 cm in depth that communicated with the exposure of the side. Lacerations, contusion on the left arm, back of the left foot and right lateral malleolus region. Evolved to a sepsis scenario in 24 hours, with microbiological identification of *Pseudomonas aeruginosa*.
Conventional Proposed and Realized Treatment
  External fixation of the femur in the emergency room, administration of clindamycin, vancomycin and cefepime, associated to a daily surgical debridement.
Results of the Performed Conventional Treatment
  Initially, it improved the septic scenario, followed by the evolution of the infection of the left lower limb with extensive areas of muscle necrosis with a high risk of amputation. 15 days after the admission the sepsis got worse, with febrile episodes of 39° C., profound anemia (receiving transfusions) and exchange of the antimicrobial medication to Tazocim. The patient was transferred with an aerial mobile ICU to Sao Paulo under medical supervision.
  The completion of conventional treatment showed a relapse in sepsis and increased necrosis of the left leg with an indication for amputation.
Proposed DECA Treatment Associated with Conventional Surgical Treatment
  The patient was admitted to the ICU of Hospital Alemão Oswaldo Cruz for debridement and application of treatment with DECA which took the following form:

Application of 1.8 cc of the DECA composition divided into 2 applications of 0.9 cc per composition along the 10 main lymphatic territories.
3-4 cm distance margin between applications to facilitate the reading of the evolution of the treatment at an interval of 4±1 days. These applications were made together with the surgical debridement (on average 1 to 2 times per week).
Administration of 36 extra perilesional compositions of 1.8 cc of each DECA in two applications of 0.9 cc per set, skirting the following open injuries without possibility of suture: the left inguinal region, the lateral side of the left thigh, the anterior left thigh and medial aspect of the left thigh, instep region and left lateral malleolus of the right leg.
Application of recombinant human interleukin-2 at low doses, at a receptor saturation level with a concentration of 1 to 2 million units per $m^2$ of the patient's body surface located in the region of the extra DECA applications. 3 million daily units were subcutaneously injected in the left thigh or inguinal region for the patient.
In the exposed regions 15 compositions DECA were applied, 1.8 cc each, for infiltration of exposed raw areas.
This extensive immunotherapy was always applied in the operating days of cleansing and surgical debridement under general anesthesia.
Thus, the first phase of immunotherapy began on 29 Jan. 2011 and ended on 19 Mar. 2011 totalling a total of nine DECA applications in periods ranging from one to two times per week, once the cleaning and debridement schedule was being followed, in the operating room (due to the severity of the pain and risk of infection by the broad extensive exposure of internal tissues in the raw areas).
Results of the Treatment with DECA Associated with Surgical Debridement and Antibiotic Therapy
  Initial assessment of the patient's injuries in the operating room on 29 Jan. 2011 showed all wounds bleeding with many clots, with extensive areas of necrosis and foul-smelling pus. After surgical cleaning, tissue continued to perform poorly with a winy general appearance without any appearance of healthy granulation tissue (FIG. 1—A1, A3 and A4). As described, the DECA immunotherapy was applied to these areas. It is interesting to note that on this occasion cultures of internal secretions and tissue fragments were performed.
  After 24 hours the first assessment of the surgical treatment associated with DECA immunotherapy was made and it demonstrated that: red lesions, with the appearance of healthy granulation tissue, with few necrotic areas with sparse secretion without foul odor and no active bleeding. The lesions were cleaned and the DECA immunotherapy was applied as noted above. On this occasion the antibiotic therapy was changed to Tazocim Meronem, Cubicin and Rifampicin pending culture results.
  On 1 Feb. 2011 the result of the cultures from the injury area, peripheral blood and central catheter showed:
  in the wound of the left thigh isolation of multidrug-resistant *Pseudomonas aeruginosa*, multiresistant *Acinetobacter baunnamii* sensitive only to polymyxin B and multiresistant *Proteus mirabiles*.
  in the peripheral blood and in the central catheter the isolation of multidrug-resistant *Acinetobacter* baunnamii sensitive only to polymyxin B.

Conclusion:

These results demonstrated that the poor prognosis of injuries in the left leg led to a new sepsis episode with *Acinetobacter baunnamii* and because of its multidrug resistance and sensitivity only to polymyxin B, did not respond to treatment with intravenous Tazocim. On the other hand, it strongly supports a beneficial effect of the DECA composition in joint surgical treatment in the local and systemic protection against this infection, since there was improvement in systemic infection and injuries before the application of polymyxin B could neutralize this etiologic agent.

That day, Meronem was exchanged for 20,000 IU/kg twice daily of Polymyxin B without changing the other medication.

On 3 Feb. 2011, it was found that the combination antibiotic therapy, debridement and DECA immunotherapy caused the remission of the septic scenario, which allowed the transfer of the patient from the ICU to the ward thereafter (FIGS. 1—B1, B2 and B3).

On 6 Feb. 2011, given the toxicity of Polymyxin B administration and other antimicrobials, the patient presented a picture of acute renal failure with oliguria. As a consequence, on the period between 6 Feb. 2011 and 15 Feb. 2011 (12 days) administration of these antibiotics was suspended, with Limezolida (Zyvox) being introduced for protection against a hospital staphylococcal contamination. On 15 Feb. 2011 the complete remission of renal failure in the patient was confirmed. In this 12-day period, with only the combination therapy of debridement, antibiotic prophylaxis and DECA immunotherapy, the patient showed excellent overall progress of the infectious and injuries being, after this period, able to withdraw the external fixator, have a surgical cleanup, and introduction of an internal rod for fixing the fracture on a surgery performed on 17 Feb. 2011. Thus, in this period, together with orthopedic surgery, there was a significant reduction in raw areas without skin with extensive tissue regeneration and no new infections.

The patient was discharged on 15 Mar. 2011, with complete cure of the infection of all complex injuries and wounds, including osteomyelitis. The patient was discharged without antibiotic therapy.

Conclusion of the Case

The existence of a severe and widespread infection and of a complex wound infected with multidrug-resistant *Acinetobacter baunnamii* sensitive only to polymyxin B which was controlled without specific antibiotic therapy with broad progression to the healing of sepsis, of all exposed lesions, and of osteomyelitis, strongly suggest a decisive role of the DECA immunotherapy, associated with debridement and antibiotics, to cure the clinical scenario, in a relatively short time.

TABLE 1

Result of the association of DECA immunotherapy, antibiotics and surgical debridement for sepsis and severe infection of complex injuries.

| Infected regions | Pre-immunotherapy cultures (29 Jan. 2011) | Result of the association of immunotherapy, antibiotic therapy, and surgical debridement (15 Mar. 2011) |
|---|---|---|
| Injury in the left thigh | Multiresistant *Pseudomonas aeroginosa*, multiresistant *Acinetobacter baumannii* only sensitive to Aztreonam and polymyxin B | No signs of infection |
| Peripheric blood | multiresistent *Acinetobacter baumannii* only sensitive to Aztreonam and polymyxin B | No signs of infection |
| Central catheter | multiresistent *Acinetobacter baumannii* only sensitive to Aztreonam and polymyxin B | No signs of infection |

Example 3: Treating Sepsis Associated with Urinary Infections and Concomitant Oropharynx with Terminal Gastric Carcinoma Patient Information
Patient CMS—Female, 38 Years Old.
Diagnosis Terminal gastric carcinoma with comorbidity of aspirative pneumonia with chemical and infection pneumonia, urinary tract and oropharyngeal infections associated with sepsis on 3 Oct. 2011. The central catheter and tracheal fluid culture was positive for *Pseudomonas aeruginosa* (*Serratia marecescens* was isolated only in tracheal aspirates) while the urine culture had isolation of multiresistant *Klebsiella pneumoniae* sensitive only to IMIPENEM and derivatives. At ICU the sepsis was characterized by hemodynamic changes and crash initially requiring the use of vasoactive drugs and respiratory support to control the episode. The patient also presented platelet blockade with major bleeding associated with an acute anemic condition (hemoglobin 8.6 g/dL) also had hypokalaemic, hyponatremic and lymphopenic (lymphocyte count of 3,000/microliter) condition.

Prior Conventional Treatment

Antibiotic therapy, vasoactive drugs, respiratory support and parenteral nutrition.

Treatment with VITER

The immunotherapy treatment was performed during a single session on 4 Oct. 2011 with the informed consent of the patient. VITER immunotherapy was performed as follows:

Application of 0.2 mL of each one of the VITER formulation (Example 1). Attenuated yellow fever virus strain 17 D204 20 µg/mL near the main 10 lymphatic territories.

Application of a low dose of recombinant human interleukin 2, at a receptor saturation level with a concentration of 1 to 2 million units per meter of body surface.

Result of Immunotherapy Treatment with VITER

On Jul. 10, 2011, anemia and thrombocytopenia were reversed with a platelet count of 178,000/microliter and a platelet aggregation function compatible with normal parameters. We also noted the normalization of serum electrolytes.

Figure 2:
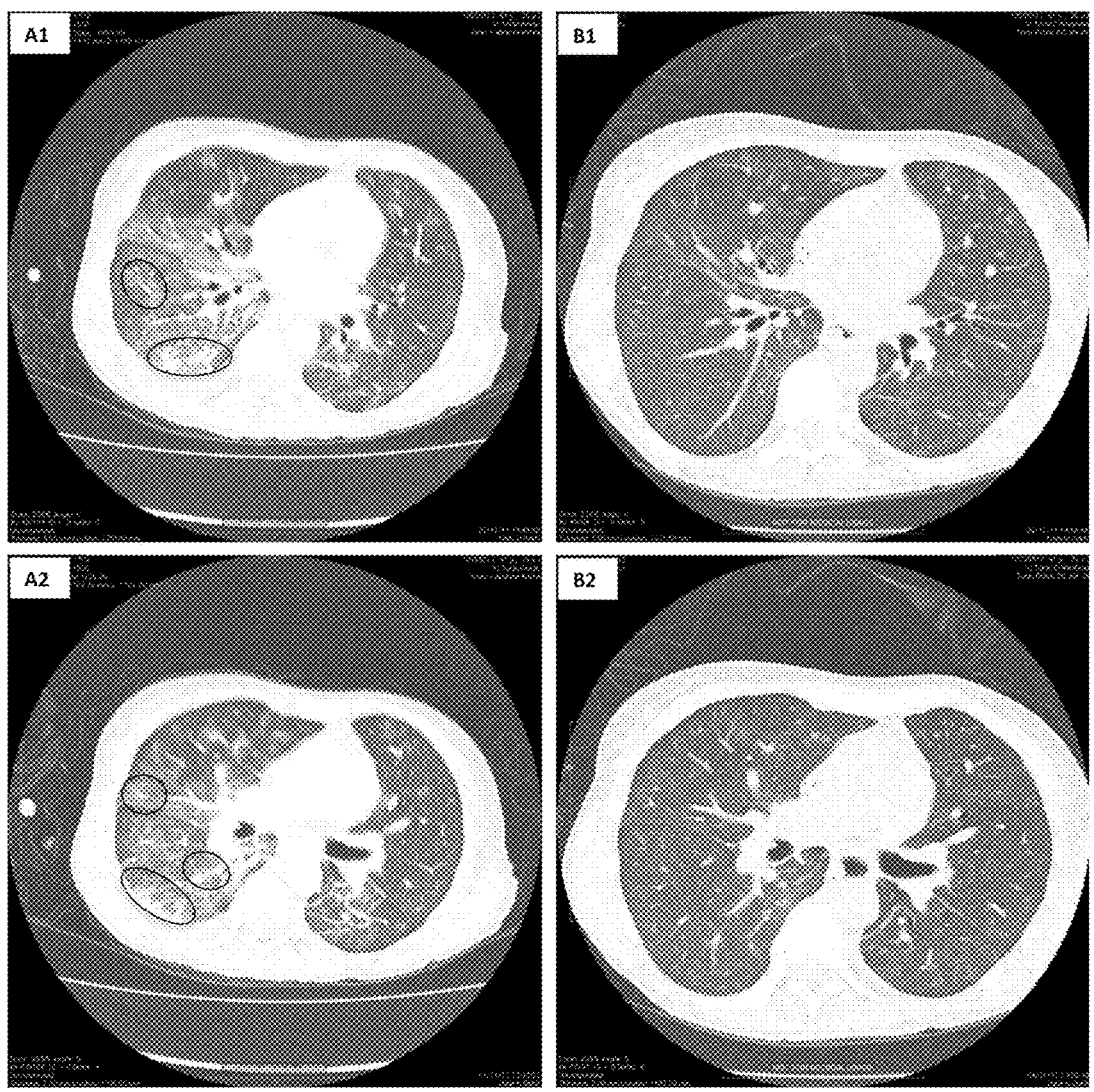
FIG. 2 shows images of Example 3. A Chest CT scan (A1 and A2) of Jan. 11, 2011 before immunotherapy and CT scan (B1 and B2) of Apr. 11, 2011 after immune treatment performed in CMS patient. In A1 and A2 is possible to identify whitish areas (circled) characteristic of infection. In B1 and B2 is clear the disappearance of whitish areas and recovery of the lung parenchyma which the image became darker. These data show a recovery of aspiration pneumonia with the combination of immunotherapy with antimicrobial treatment.

The immunostimulation caused immunocompetence recovery and activation of the effector T loop as the lymphocyte count increased from 3,000/microliter on 3 Oct. 2011 to 9,400/microliter on Jul. 10, 2011. C-reactive protein concentration was reduced to 61 mg/l indicating control the infection. It is necessary to mention that the patient remained unther immunological treatment at "Home care" regimen. On Jan. 11, 2011 was diagnosed an aspiration pneumonia confirmed by chest tomography with amazing recovery before the current state of the art in 03 days of immunotherapy associated with antimicrobial treatment according to CT scan of Apr. 11, 2011 (FIG. 2).

Case Conclusion

Discharge from hospital to home care on Sep. 10, 2011. The evaluated data and the clinical course of the patient indicate that the innovative immunotherapy was responsible for the amazing recovery from the critical sepsis condition the patient was in. The continuity of immunostimulatory treatment also contributes to the improvement of the patient's life quality and an amazing improvement in life expectancy. According to the state of the art this widespread and terminal cancer condition leads to death in about 1 month, while the immunostimulation of the present invention allowed for an unexpected survival of 1 year and a half, enjoying the company of relatives.

Example 4: Treating Infection (Multiresistant Bacteria of SARS in Septic Shock)

Patient Information
Patient AMB—female, 39 years old.
Primary Diagnosis
Severe sepsis and Septic shock
Secondary Diagnosis
Presented as comorbity:
  Severe Acute Respiratory Syndrome (SARS);
  Shock;
  Acute Renal Failure;
  Disseminated Intravascular Coagulation;
  Hepatic failure signs;
Identification and Summary of the Clinical History On 19 Apr. 2007 were hospitalized with diagnosis of community pneumonia, non-produced cough and high fever. After 10 hours of hospital admission, patient got worse requiring tranferece to Intense Care Unit (ICU) with respiratory infection and septic shock characterized by: hipotension, SARS; renal and hepatic failure; Disseminated Intravascular Coagulation; serum lactate increase, hemodynamic and eletrolytes colapse.

Prior Conventional Treatment

On 20 Apr. 2007 were treated with Ceftriaxone and Levofloxacin. However, after clinical complication and ICU admission when became essential: i) start respiratory and hemodynamic support; ii) antimicrobial regimen replace by Meropenem with Vancomicin; iii) association of plasma transfusion 08U and IV active protein C to reverse Disseminated Intravascular Coagulation and make opsonization process possible. Inspite of all efforts patient did not experince any clinical and laboratory improvement.

Proposed IRS with DECA Treatment Associated with Conventional Treatment

The immunotherapy treatment was performed nine sessions starting on Apr. 21, 2011 after informed consent of the patient. DECA immunotherapy was performed as follows:
  Application of 0.2 mL of each one of the 10 antigenic components (1. Koch's Tuberculin ((lysate inactivated *Mycobacterium bovis* 0.0036 ng/mL); 2. PPD (0.0036 µg/mL); 3. Lysate inactivated *Staphylococcus* (*Staphylococcus aureus* and *Staphylococcus epidermidis* in equal parts 6.31 µg/mL); 4 Lysate inactivated *Streptococcus* (*Streptococcus pyogenes*, *Streptococcus pneumonie* and *Enterococcus faecalis* in equal parts 6.31 µg/mL).; 5. Streptokinase derived from lysate inactivated and purified *Streptococcus* beta-hemolytic 0.404 µg/mL); 6. Dornase derived from lysate inactivated and purified *Streptococcus* beta-hemolytic 0.101 µg/mL); 7. Oidiomycin (antigenic extract of *Candida albicans* 6.31 µg/mL); 8. *Trichophytin* (antigenic extract of *Tricophyton* spp 6.31 µg/mL); 9. Lysate inactivated *Escherichia coli* (EPEC 6.31 µg/mL); 10. Lysate inactivated *Salmonella* (*Salmonella bongori*, *Salmonella enterica* and *Salmonella subterranea* in equal parts 6.31 µg/mL).

Result of Immunotherapy with IRS-DECA Associated with Conventional Treatment

Figure 3:
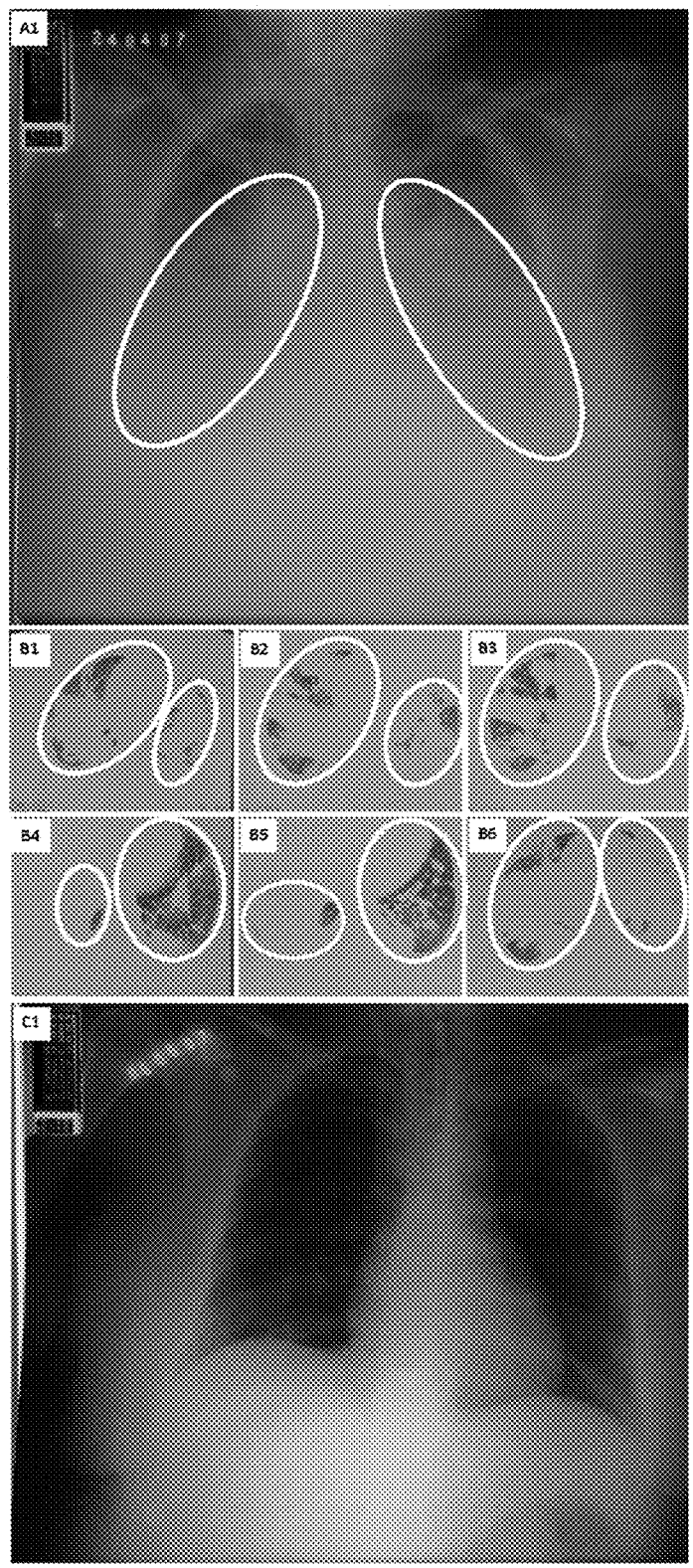
FIG. 3 shows images of Example 4. An X-Ray (A1) of 24 Apr. 2007 (3 days after immunotherapy starts) and CT scan (B1 to B6) of 27 Apr. 2007 it's easily to identify critical SARS condition under septic shock. X-Ray (C1) of 6 May 2007 evidences complete recover after immune treatment performed in AMB patient. In A1 is possible to identify whitish areas (circled) characteristic of infection. In B1-B6 the clinical status is so critical that whitish areas barely allow to identify anatomical contours our parameters (circular). In C1 is clear the disappearance of whitish areas and complete recovery of the lung parenchyma, without sequels, which the image became darker. These data show a recovery of sepsis associated with SARS, CIVD, hepatic and renal failure with the combination of 6 sessions of immunotherapy with antimicrobial treatment in 15 days.

On 26 May 2007 serum eletrolytes and lactate reached normal levels and thrombocytopenia were reversed with a platelet count of 167,000/mm$^3$ and a platelet aggregation function compatible with normal parameters. ON Apr. 27, 2007 SARS still very severe and start to improve. On 29 May 2007 arterial blood gas analysis saturation and pO$_2$ were reversed evidencing hemodynamic recover. The immunostimulation caused immunocompetence recovery and activation of the effector T loop with normalized complement fractions on 28 Apr. 2007, the lymphocyte count decreased from 21.100/mm$^3$ on 20 Apr. 2007 (that got worse to 43.700/mm$^3$ on 22 Apr. 2007) to 11.000/mm$^3$ on 30 Apr. 2007 when CD3, CD4 and CD8 fractions presented proper levels. The respiratory condition improve drastically after Apr. 29, 2007 and respiratory support were removed. Patient was discharged from ICU on 6 May 2007 with complete recover of severe sepsis. On 19 Apr. 2007 was diagnosed an community pneumonia confirmed by chest X-Ray of 24 Apr. 2007 (FIG. 3—A1) and worsened to SARS associated with sepsis as can see on CT scan of 27 Apr. 2007 (FIG. 3—B1 to B6) with amazing recovery before the current state of the art in 15 days of immunotherapy (6 sessions) associated with antimicrobial treatment according to laboratories and X-Ray (FIG. 3—C1) exams of 6 May 2007.

Case Conclusion

Discharge from hospital on 6 May 2007. The evaluated data and the clinical course of the patient indicate that the innovative immunotherapy was responsible for the amazing recovery from the critical severe sepsis and septic shock conditions that the patient was in. The continuity of immunostimulatory treatment also contributes to the complete extinguish the severe infection and an amazing improvement in life expectancy. According to the state of the art this multiresistant bacteria of SARS in septic shock associated with renal and hepatic failure conditions leads to death in hours, while the immunostimulation of the present invention allowed for an unexpected survival with no sequel.

In short, the clinical cases presented hereinabove demonstrate that high complexity illnesses and diseases, with obscure to very poor prognosis, have been addressed more properly, with advantageous and more efficient approaches through the use of the IRS compositions the present invention.

REFERENCES

In order to better understand the above concept and definitions related to the present invention, the following references are incorporated into the present patent application:

1. Pulendran B. The varieties of immunological experience: of pathogens, stress, and dendritic cells. Annual review of immunology. 2015; 33:563-606.
2. Steinman R M. Decisions about dendritic cells: past, present, and future. Annual review of immunology. 2012; 30:1-22.

3. Steinman R M, Banchereau J. Taking dendritic cells into medicine. Nature. 2007; 449(7161):419-26.
4. Martin-Fontecha A, Baumjohann D, Guarda G, Reboldi A, Hons M, Lanzavecchia A, et al. CD40L+ CD4+ memory T cells migrate in a CD62P-dependent fashion into reactive lymph nodes and license dendritic cells for T cell priming. The Journal of experimental medicine. 2008; 205(11):2561-74.
5. Soderberg K A, Payne G W, Sato A, Medzhitov R, Segal S S, Iwasaki A. Innate control of adaptive immunity via remodeling of lymph node feed arteriole. Proceedings of the National Academy of Sciences of the United States of America. 2005; 102(45):16315-20.
6. Narni-Mancinelli E, Campisi L, Bassand D, Cazareth J, Gounon P, Glaichenhaus N, et al. Memory CD8+ T cells mediate antibacterial immunity via CCL3 activation of TNF/ROI+ phagocytes. The Journal of experimental medicine. 2007; 204(9):2075-87.
7. Jeffrey K. Rechallenging immunological memory. Nature medicine. 2007; 13(10):1142.
8. Weisel F J, Zuccarino-Catania G V, Chikina M, Shlomchik M J. A Temporal Switch in the Germinal Center Determines Differential Output of Memory B and Plasma Cells. Immunity. 2016; 44(1):116-30.
9. De Silva N S, Klein U. Dynamics of B cells in germinal centres. Nat Rev Immunol. 2015; 15(3):137-48.
10. Sallusto F, Monticelli S. The many faces of CD4 T cells: roles in immunity and disease. Seminars in immunology. 2013; 25(4):249-51.
11. Sallusto F, Lanzavecchia A. Heterogeneity of CD4+ memory T cells: functional modules for tailored immunity. European journal of immunology. 2009; 39(8):2076-82.
12. Becattini S, Latorre D, Mele F, Foglierini M, De Gregorio C, Cassotta A, et al. T cell immunity. Functional heterogeneity of human memory CD4(+) T cell clones primed by pathogens or vaccines. Science. 2015; 347(6220):400-6.
13. Zhu J, Paul W E. CD4 T cells: fates, functions, and faults. Blood. 2008; 112(5):1557-69.
14. Sallusto F, Zielinski C E, Lanzavecchia A. Human Th17 subsets. European journal of immunology. 2012; 42(9):2215-20.
15. Duhen T, Duhen R, Lanzavecchia A, Sallusto F, Campbell D J. Functionally distinct subsets of human FOXP3+ Treg cells that phenotypically mirror effector Th cells. Blood. 2012; 119(19):4430-40.
16. Crotty S. Follicular helper CD4 T cells (TFH). Annual review of immunology. 2011; 29:621-63.
17. Zielinski C E, Corti D, Mele F, Pinto D, Lanzavecchia A, Sallusto F. Dissecting the human immunologic memory for pathogens. Immunological reviews. 2011; 240(1):40-51.
18. Townsend E C, Murakami M A, Christodoulou A, Christie A L, Koster J, DeSouza T A, et al. The Public Repository of Xenografts Enables Discovery and Randomized Phase II-like Trials in Mice. Cancer Cell. 2016; 29(4):574-86.
19. In this issue. Nature Reviews Immunology. 2016; 16(2):69-.
20. Cerwenka A, Lanier L L. Natural killer cell memory in infection, inflammation and cancer. Nat Rev Immunol. 2016; 16(2):112-23.
21. Leavy O. Immune memory: T-box tuning for TRM cell fate. Nat Rev Immunol. 2016; 16(2):71.
22. Mackay L K, Wynne-Jones E, Freestone D, Pellicci D G, Mielke L A, Newman D M, et al. T-box Transcription Factors Combine with the Cytokines TGF-beta and IL-15 to. Immunity. 2015; 43(6):1101-11 LID—10.016/j.immuni.2015.11.008 [doi] LID—S1074-7613(15)00460-4 [Pii].
23. Bird L. Immune memory: ILC2s drive allergen recall. Nat Rev Immunol. 2016; 16(2):72-3.
24. Halim T Y, Hwang Y Y, Scanlon S T, Zaghouani H, Garbi N, Fallon P G, et al. Group 2 innate lymphoid cells license dendritic cells to potentiate memory TH2 cell responses. Nat Immunol. 2016; 17(1):57-64.
25. Leavy O. Immune memory: Sequential evolution of B cell memory. Nat Rev Immunol. 2016; 16(2):72-3.
26. Kugelberg E. Immune memory: Lingering human T cells. Nat Rev Immunol. 2016; 16(2):73.
27. Oliveira G, Ruggiero E, Stanghellini M T, Cieri N, D'Agostino M, Fronza R, et al. Tracking genetically engineered lymphocytes long-term reveals the dynamics of T. Sci Transl Med. 2015; 7(317):317ra198 LID—10.1126/scitranslmed.aac8265 [doi].
28. Mueller S N, Mackay L K. Tissue-resident memory T cells: local specialists in immune defence. Nat Rev Immunol. 2016; 16(2):79-89.
29. Rosenblum M D, Way S S, Abbas A K. Regulatory T cell memory. Nat Rev Immunol. 2016; 16(2):90-101.
30. Farber D L, Netea M G, Radbruch A, Raj ewsky K, Zinkernagel R M. Immunological memory: lessons from the past and a look to the future. Nat Rev Immunol. 2016; 16(2):124-8.
31. Laidlaw B J, Craft J E, Kaech S M. The multifaceted role of CD4(+) T cells in CD8(+) T cell memory. Nat Rev Immunol. 2016; 16(2):102-11 LID—10.1038/nri.2015.10 [doi].
32. Tubo N J, Fife B T, Pagan A J, Kotov D I, Goldberg M F, Jenkins M K. Most microbe-specific naive CD4(+) T cells produce memory cells during infection. Science. 2016; 351(6272):511-4.
33. Flierl M A, Rittirsch D, Gao H, Hoesel L M, Nadeau B A, Day D E, et al. Adverse functions of IL-17A in experimental sepsis. FASEB journal: official publication of the Federation of American Societies for Experimental Biology. 2008; 22(7):2198-205.
34. Xiao H, Siddiqui J, Remick D G. Mechanisms of mortality in early and late sepsis. Infection and immunity. 2006; 74(9):5227-35.
35. Buras J A, Holzmann B, Sitkovsky M. Animal models of sepsis: setting the stage. Nature reviews Drug discovery. 2005; 4(10):854-65.
36. DiPaolo R J, Shevach E M. CD4+ T-cell development in a mouse expressing a transgenic TCR derived from a Treg. Eur J Immunol. 2009; 39(1):234-40.
37. Weber S U, Schewe J C, Lehmann L E, Muller S, Book M, Klaschik S, et al. Induction of Bim and Bid gene expression during accelerated apoptosis in severe sepsis. Crit Care. 2008; 12(5):R128.
38. Schwulst S J, Muenzer J T, Peck-Palmer O M, Chang K C, Davis C G, McDonough J S, et al. Bim siRNA decreases lymphocyte apoptosis and improves survival in sepsis. Shock. 2008; 30(2):127-34.
39. Martignoni A, Tschop J, Goetzman H S, Choi L G, Reid M D, Johannigman J A, et al. CD4-expressing cells are early mediators of the innate immune system during sepsis. Shock. 2008; 29(5):591-7.
40. Schmoeckel K, Traffehn S, Eger C, Potschke C, Broker B M. Full activation of CD4+ T cells early during sepsis requires specific antigen. Shock. 2015; 43(2):192-200.

41. Latifi S Q, O'Riordan M A, Levine A D. Interleukin-10 controls the onset of irreversible septic shock. Infection and immunity. 2002; 70(8):4441-6.
42. Querec T, Bennouna S Fau—Alkan S, Alkan S Fau—Laouar Y, Laouar Y Fau—Gorden K, Gorden K Fau—Flavell R, Flavell R Fau—Akira S, et al. Yellow fever vaccine YF-17D activates multiple dendritic cell subsets via TLR2. J Exp Med. 2006; 203(2):413-24.
43. Pulendran B, Miller J, Querec T D, Akondy R, Moseley N, Laur 0, et al. Case of yellow fever vaccine—associated viscerotropic disease with prolonged viremia, robust adaptive immune responses, and polymorphisms in CCR5 and RANTES genes. The Journal of infectious diseases. 2008; 198(4):500-7.
44. Nakaya H I, Pulendran B. Vaccinology in the era of high-throughput biology. Philosophical transactions of the Royal Society of London Series B, Biological sciences. 2015; 370(1671).
45. Hagan T, Nakaya H I, Subramaniam S, Pulendran B. Systems vaccinology: Enabling rational vaccine design with systems biological approaches. Vaccine. 2015.
46. Li S, Nakaya H I, Kazmin D A, Oh J Z, Pulendran B. Systems biological approaches to measure and understand vaccine immunity in humans. Seminars in immunology. 2013; 25(3):209-18.
47. Pulendran B, Ahmed R. Immunological mechanisms of vaccination. Nature immunology. 2011; 12(6):509-17.
48. Buonaguro L, Pulendran B. Immunogenomics and systems biology of vaccines. Immunological reviews. 2011; 239(1):197-208.
49. Pulendran B, Li S, Nakaya H I. Systems vaccinology. Immunity. 2010; 33(4):516-29.
50. Ahmed R, Pulendran B. Learning vaccinology from viral infections. The Journal of experimental medicine. 2011; 208(12):2347-9.
51. Edward F. McCarthy M D. THE TOXINS OF WILLIAM B. COLEY AND THE TREATMENT OF BONE AND SOFT-TISSUE SARCOMAS. The Iowa Orthopaedic Journal. 2006; 26.
52. Waldner H. Activation of antigen-presenting cells by microbial products breaks self tolerance and induces autoimmune disease. Journal of Clinical Investigation. 2004; 113(7):990-7.
53. Maryanski J L, Boon T. Immunogenic variants obtained by mutagenesis of mouse mastocytoma P815. IV. Analysis of variant-specific antigens by selection of antigen-loss variants with cytolytic T cell clones. European journal of immunology. 1982; 12(5):406-12.
54. Boon T, Maryanski J. Tumour cell variants with increased immunogenicity obtained by mutagen treatment. Cancer Surv. 1985; 4(1):135-48.
55. Koguchi Y, Thauland T J, Slifka M K, Parker D C. Preformed C D40 ligand exists in secretory lysosomes in effector and memory CD4+ T cells and is quickly expressed on the cell surface in an antigen-specific manner. Blood. 2007; 110(7):2520-7.
56. Narni-Mancinelli E, Soudja S M, Crozat K, Dalod M, Gounon P, Geissmann F, et al. Inflammatory monocytes and neutrophils are licensed to kill during memory responses in vivo. PLoS pathogens. 2011; 7(12): e1002457.
57. Narni-Mancinelli E, Vivier E. Delivering three punches to knockout intracellular bacteria. Cell. 2014; 157(6): 1251-2.
58. Bajenoff M, Narni-Mancinelli E, Brau F, Lauvau G. Visualizing early splenic memory CD8+ T cells reactivation against intracellular bacteria in the mouse. PloS one. 2010; 5(7):e11524.
59. Soudja S M, Ruiz A L, Marie J C, Lauvau G. Inflammatory monocytes activate memory CD8(+) T and innate NK lymphocytes independent of cognate antigen during microbial pathogen invasion. Immunity. 2012; 37(3):549-62.
60. Kohlhapp F J, Kaufman H L. Molecular Pathways: Mechanism of Action for Talimogene Laherparepvec, a New Oncolytic Virus Immunotherapy. Clinical cancer research: an official journal of the American Association for Cancer Research. 2016; 22(5):1048-54.
61. Topalian S L, Wolchok J D, Chan T A, Mellman I, Palucka K, Banchereau J, et al. Immunotherapy: The path to win the war on cancer? Cell. 2015; 161(2):185-6.
62. Kaufman H L. Vaccines for melanoma and renal cell carcinoma. Seminars in oncology. 2012; 39(3):263-75.
63. Glimcher L H, Lindvall O, Aguirre V, Topalian S L, Musunuru K, Fauci A S. Translating research into therapies. Cell. 2012; 148(6):1077-8.
64. Nakaya H I, Wrammert J, Lee E K, Racioppi L, Marie-Kunze S, Haining W N, et al. Systems biology of vaccination for seasonal influenza in humans. Nature immunology. 2011; 12(8):786-95.
65. Sallusto F, Lanzavecchia A, Araki K, Ahmed R. From vaccines to memory and back. Immunity. 2010; 33(4): 451-63.
66. Querec T D, Akondy R S, Lee E K, Cao W, Nakaya H I, Teuwen D, et al. Systems biology approach predicts immunogenicity of the yellow fever vaccine in humans. Nature immunology. 2009; 10(1):116-25.
67. Amanna I J, Carlson N E, Slifka M K. Duration of humoral immunity to common viral and vaccine antigens. The New England journal of medicine. 2007; 357(19): 1903-15.
68. Querec T, Bennouna S, Alkan S, Laouar Y, Gorden K, Flavell R, et al. Yellow fever vaccine YF-17D activates multiple dendritic cell subsets via TLR2, 7, 8, and 9 to stimulate polyvalent immunity. The Journal of experimental medicine. 2006; 203(2):413-24.
69. Pulendran B, Ahmed R. Translating innate immunity into immunological memory: implications for vaccine development. Cell. 2006; 124(4):849-63.
70. Amanna I J, Slifka M K, Crotty S. Immunity and immunological memory following smallpox vaccination. Immunological reviews. 2006; 211:320-37.
71. Arlen P M, Kaufman H L, DiPaola R S. Pox viral vaccine approaches. Seminars in oncology. 2005; 32(6):549-55.
72. Hammarlund E, Lewis M W, Hansen S G, Strelow L I, Nelson J A, Sexton G J, et al. Duration of antiviral immunity after smallpox vaccination. Nature medicine. 2003; 9(9):1131-7.
73. Crotty S, Felgner P, Davies H, Glidewell J, Villarreal L, Ahmed R. Cutting edge: long-term B cell memory in humans after smallpox vaccination. Journal of immunology. 2003; 171(10):4969-73.
74. Cono J, Casey C G, Bell D M, Centers for Disease C, Prevention. Smallpox vaccination and adverse reactions. Guidance for clinicians. MMWR Recomm Rep. 2003; 52(RR-4):1-28.
75. Frey S E, Couch R B, Tacket C O, Treanor J J, Wolff M, Newman F K, et al. Clinical responses to undiluted and diluted smallpox vaccine. The New England journal of medicine. 2002; 346(17):1265-74.

76. Ahmed R, Gray D. Immunological memory and protective immunity: understanding their relation. Science. 1996; 272(5258):54-60.
77. Koplan J P, Marton K I. Smallpox vaccination revisited. Some observations on the biology of vaccinia. The American journal of tropical medicine and hygiene. 1975; 24(4):656-63.
78. Theiler M, Smith H H. The Use of Yellow Fever Virus Modified by in Vitro Cultivation for Human Immunization. The Journal of experimental medicine. 1937; 65(6): 787-800.

What is claimed:

1. A pharmaceutical product comprising one or more antibiotics and one or more immunological response shifter (IRS) immunogenic compositions for modulating the immune system comprising a therapeutically effective amount of three or more synthetic antigenic agents or natural antigenic agents, or fractions and combinations thereof, comprising pathogen-associated molecular patterns (PAMPS) and/or danger associated molecular patterns (DAMPS) selected from at least two groups consisting of: (A) antigenic agents with molecular patterns associated with bacteria, (B) antigenic agents with molecular patterns associated with viruses, (C) antigenic agents with molecular patterns associated with fungi and yeasts, (D) antigenic agents with molecular patterns associated with protozoa, (E) antigenic agents with molecular patterns associated with helminths, and (F) antigenic agents with molecular patterns associated with prions; and one or more physiologically acceptable carriers, excipients, diluents or solvents.

2. The pharmaceutical product of claim 1 wherein the antigenic agents are selected from at least four groups (A), (B), (C), (D), (E) and (F).

3. The pharmaceutical product of claim 1, wherein the antibiotic is a beta-Lactam.

4. The pharmaceutical product of claim 1 wherein the antibiotics are selected from the following classes: Amino Acid Derivatives, Aminoglycosides, Aureolic Acids, Aziridines, Ansamycins, Benzenoids, Benzimidazoles, Carbapenems, Cephalosporins, Coumarin-glycosides, Diphenyl Ether Derivatives, Epipolythiodioxopiperazines, Fatty Acid Derivatives, Glucosamine, Imidazoles, Indol Derivatives, Macrolactams, Macrolides, Nucleosides, Penicillins Peptides, Peptidyl Nucleosides, Phenicoles, Polyenes, Polyethers, Pyridines, Pyrimidines, Quinolones, Fluoroquinolones, Statins, Steroids, Sulfonamides, Taxoides and Tetracyclines.

5. The pharmaceutical product of claim 4 wherein the antibiotics are selected from the following classes: ansamycins, Penicillins, Cephalosporins, Carbapenems and Lipopeptides.

6. The pharmaceutical product of claim 4, wherein the peptides are Glycopeptides or Lipopeptides.

7. The pharmaceutical product of claim 1 comprising from 4 to 20 antigenic agents selected from the group consisting of antigenic agents derived from: dornase, yeast, oidiomycin, purified protein derivative of Koch's *bacillus* (PPD), prions, streptokinases, *Streptococcus* toxoid, diphtheria toxoid, tetanus toxoid, Koch's original tuberculin, *Ascaris lumbricoides* lysates, *Aspergillus* spp., *Candida albicans, Candida glabrata, Candida parapsilosis, Chlamydia* spp., *Cryptosporidium* spp., *Dermatophytes, Entamoeba hystolitica, Enterobius vermicularis, Enterococcus faecalis, Epidermophyton floccosum, Escherichia coli, Giardia lamblia, Haemophilus influenzae, Microsporum canis, Mycobacterium* spp., *Neisseria gonorrhoeae*, Human papillomavirus, Polio virus, *Proteus* spp., *Salmonella* spp., *Serratia* spp., *Shigella* spp., *Staphylococcus* spp., *Streptococcus* spp., *Toxoplasma gondii, Trichomonas vaginalis*, trichophytin, *Trichophyton* spp., yellow fever virus, hepatitis B virus, rubella virus, varicella zoster virus, variola virus, mumps virus, measles virus, herpes virus and vaccinia virus.

8. The pharmaceutical product of claim 7, wherein the *Aspergillus* spp. is *Aspergillus flavus, Aspergillus fumigatus*, or *Aspergillus terreus,* the *Chlamydia* spp. is *Chlamydia pneumoniae, Chlamydia psittaci*, or *Chlamydia trachomatis,* the *Mycobacterium* spp. is *Mycobacterium bovis, Mycobacterium leprae*, or *Mycobacterium tuberculosis,* the *Proteus* spp. is *Proteus mirabilis, Proteus penerii*, or *Proteus vulgaris,* the *Salmonella* spp. is *Salmonella bongori*, or *Salmonella enterica,* the *Serratia* spp. is *Serratia liquefaciens*, or *Serratia* marcencens, the *Shigella* spp. is *Shigella flexneri*, or *Shigella sonnei,* the *Staphylococcus* spp. is *Staphylococcus aureus, Staphylococcus epidermidis*, or *Strongyloides stercoralis,* the *Streptococcus* spp. is *Streptococcus bovis, Streptococcus viridans, Streptococcus equinus, Streptococcus pneumoniae*, or *Streptococcus pyogenes*, and the *Trichophyton* spp. is *Trichophyton rubrum, Trichophyton tonsurans*, or *Trichophyton mentagrophytes.*

9. A method to treat sepsis and multi resistant bacterial infection in a human or an animal comprising administering to the human or animal an effective amount of one or more antibiotics and one or more immunological response shifter (IRS immunogenic compositions comprising a therapeutically effective amount of three or more synthetic antigenic agents or natural antigenic agents, or fractions and combinations thereof, comprising pathogen-associated molecular patterns (PAMPS) and/or danger associated molecular patterns (DAMPS) selected from at least two groups consisting of: (A) antigenic agents with molecular patterns associated with bacteria, (B) antigenic agents with molecular patterns associated with viruses, (C) antigenic agents with molecular patterns associated with fungi and yeasts, (D) antigenic agents with molecular patterns associated with protozoa, (E) antigenic agents with molecular patterns associated with helminthes, and (F) antigenic agents with molecular patterns associated with prions; and one or more physiologically acceptable carriers, excipients, diluents or solvents.

10. A method to modulate an immune system response in a human or an animal who has a bacterial infection comprising administering to the human or animal an effective amount of one or more immunological response shifter (IRS) immunogenic compositions comprising a therapeutically effective amount of three or more synthetic antigenic agents or natural antigenic agents, or fractions and combinations thereof, comprising pathogen-associated molecular patterns (PAMPS) and/or danger associated molecular patterns (DAMPS) selected from at least two groups consisting of: (A) antigenic agents with molecular patterns associated with bacteria, (B) antigenic agents with molecular patterns associated with viruses, (C) antigenic agents with molecular patterns associated with fungi and yeasts, (D) antigenic agents with molecular patterns associated with protozoa, (E) antigenic agents with molecular patterns associated with helminthes, and (F) antigenic agents with molecular patterns associated with prions; and one or more physiologically acceptable carriers, excipients, diluents or solvents.

* * * * *